United States Patent
Yang et al.

(10) Patent No.: US 10,821,110 B2
(45) Date of Patent: *Nov. 3, 2020

(54) COMPOSITE PREPARATION, CONTAINING NOVEL 3-(4-(BENZYLOXY)PHENYL)HEX-4-INOIC ACID DERIVATIVE AND ANOTHER ACTIVE INGREDIENT, FOR PREVENTING OR TREATING METABOLIC DISEASES

(71) Applicant: HYUNDAI PHARM CO., LTD., Chungcheongnam-do (KR)

(72) Inventors: Jin Yang, Gyeonggi-do (KR); Jin Woong Kim, Gyeonggi-do (KR); Han Kyu Lee, Gyeonggi-do (KR); Jae Hyun Kim, Gyeonggi-do (KR); Chang Mo Son, Gyeonggi-do (KR); Kyu Hwan Lee, Gyeonggi-do (KR); Hyung-Ho Choi, Gyeonggi-do (KR); Daehoon Kim, Seoul (KR); Tae-Young Ha, Gyeonggi-do (KR); Jaekeol Rhee, Gyeonggi-do (KR)

(73) Assignee: HYUNDAI PHARM CO., LTD., Chungcheongnam-do (KR)

( * ) Notice: Subject to any disclaimer, the term of this patent is extended or adjusted under 35 U.S.C. 154(b) by 162 days.

This patent is subject to a terminal disclaimer.

(21) Appl. No.: 15/511,955

(22) PCT Filed: Oct. 16, 2015

(86) PCT No.: PCT/KR2015/010976
§ 371 (c)(1),
(2) Date: Mar. 16, 2017

(87) PCT Pub. No.: WO2016/060517
PCT Pub. Date: Apr. 21, 2016

(65) Prior Publication Data
US 2017/0296539 A1   Oct. 19, 2017

(30) Foreign Application Priority Data
Oct. 17, 2014  (KR) ........................ 10-2014-0141216

(51) Int. Cl.
*A61K 31/506* (2006.01)
*A61K 9/00* (2006.01)
(Continued)

(52) U.S. Cl.
CPC .......... *A61K 31/506* (2013.01); *A61K 9/0019* (2013.01); *A61K 9/14* (2013.01); *A61K 9/20* (2013.01); *A61K 9/48* (2013.01); *A61K 31/192* (2013.01); *A61K 31/357* (2013.01); *A61K 31/40* (2013.01); *A61K 31/4035* (2013.01); *A61K 31/44* (2013.01); *A61K 31/445* (2013.01); *A61K 31/454* (2013.01); *A61K 31/47* (2013.01); *A61K 31/495* (2013.01); *A61K 31/496* (2013.01); *A61K 45/06* (2013.01); *C07C 59/72* (2013.01); *C07D 207/06* (2013.01); *C07D 209/44* (2013.01); *C07D 211/14* (2013.01); *C07D 211/70* (2013.01); *C07D 215/06* (2013.01); *C07D 295/096* (2013.01); *C07D 317/72* (2013.01); *C07D 401/04* (2013.01); *C07D 403/04* (2013.01); *C07D 413/04* (2013.01); *C07D 417/04* (2013.01)

(58) Field of Classification Search
None
See application file for complete search history.

(56) References Cited

U.S. PATENT DOCUMENTS

2007/0142384 A1  6/2007  Akerman et al. ............. 514/249
2007/0213364 A1  9/2007  Yasuma et al.
(Continued)

FOREIGN PATENT DOCUMENTS

CN      1946666 A      4/2007
CN      104740635      7/2015  ............. A61K 45/06
(Continued)

OTHER PUBLICATIONS

Rosenstock et al., Efficacy and safety of empagliflozen, a sodium glucose cotransporter 2 (SGLT2) inhibitor, as add-on to metformin in type 2 diabetes with mild hyperglycaemia, 2013, Diabetes, Obesity and Metabolism, 15, pp. 1154-1160 (Year: 2013).*
(Continued)

*Primary Examiner* — Kortney L. Klinkel
*Assistant Examiner* — Tori Strong
(74) *Attorney, Agent, or Firm* — Harness, Dickey & Pierce, P.L.C.

(57) ABSTRACT

The present invention relates to a pharmaceutical composition for preventing or treating metabolic diseases, in which a novel 3-(4-(benzyloxy)phenyl)hex-4-inoic acid derivative and at least another active ingredient, which is selected from the group consisting of dipeptidyl peptidase-4 (DPPIV) inhibitor-based, sulfonylurea-based, thiazolidinedione (TZD)-based, biguanide-based, and sodium/glucose cotransporter 2 (SGLT2) inhibitor-based drugs, may be administered in combination or in the form of a composite preparation. The use of the composition of the present invention can provide a remarkably excellent blood sugar reducing effect in various animal diabetic disease models, and the composition of the present invention can be favorably used as a pharmaceutical composition for preventing or treating metabolic diseases, such as obesity, diabetes type I, diabetes type II, glucose intolerance symptoms, insulin resistance symptoms, hyperglycemia, hyperlipidemia, hypertriglyceridemia, hypercholesterolemia, dyslipidemia, and syndrome X.

22 Claims, 11 Drawing Sheets

(51) Int. Cl.

| | | |
|---|---|---|
| *A61K 9/14* | (2006.01) | |
| *A61K 9/20* | (2006.01) | |
| *A61K 9/48* | (2006.01) | |
| *A61K 31/132* | (2006.01) | |
| *A61K 31/357* | (2006.01) | |
| *A61K 31/40* | (2006.01) | |
| *A61K 31/4035* | (2006.01) | |
| *A61K 31/44* | (2006.01) | |
| *A61K 31/445* | (2006.01) | |
| *A61K 31/454* | (2006.01) | |
| *A61K 31/47* | (2006.01) | |
| *A61K 31/495* | (2006.01) | |
| *A61K 31/496* | (2006.01) | |
| *A61K 45/06* | (2006.01) | |
| *C07C 59/72* | (2006.01) | |
| *C07D 207/06* | (2006.01) | |
| *C07D 209/44* | (2006.01) | |
| *C07D 211/14* | (2006.01) | |
| *C07D 211/70* | (2006.01) | |
| *C07D 215/06* | (2006.01) | |
| *C07D 295/096* | (2006.01) | |
| *C07D 317/72* | (2006.01) | |
| *C07D 401/04* | (2006.01) | |
| *C07D 403/04* | (2006.01) | |
| *C07D 413/04* | (2006.01) | |
| *C07D 417/04* | (2006.01) | |
| *A61K 31/192* | (2006.01) | |

(56) References Cited

U.S. PATENT DOCUMENTS

| | | | |
|---|---|---|---|
| 2009/0111859 A1 | 4/2009 | Brown et al. | 514/369 |
| 2011/0092531 A1 | 4/2011 | Hamdouchi et al. | 514/278 |
| 2012/0004187 A1 | 1/2012 | Keil et al. | 514/21.3 |
| 2016/0024063 A1 | 1/2016 | Yang et al. | |

FOREIGN PATENT DOCUMENTS

| | | | | |
|---|---|---|---|---|
| JP | 2010-503695 A | 2/2010 | | |
| JP | 2010-524932 A | 7/2010 | | |
| JP | 2013-508279 A | 3/2013 | | |
| JP | 2013-512229 A | 4/2013 | | |
| KR | 10-2007-0004769 | 1/2007 | ........... | C07D 277/30 |
| KR | 10-2012-0051777 | 5/2012 | ........... | C07D 221/20 |
| KR | 10-2013-0135827 | 12/2013 | ............ | C07C 59/72 |
| KR | 10-2014-0126248 | 10/2014 | ........... | C07D 317/72 |
| RU | 2628077 C2 | 8/2017 | | |
| WO | WO-2005/086661 A2 | 9/2005 | | |
| WO | WO-2008/001931 A2 | 1/2008 | | |
| WO | WO 2008-030618 | 3/2008 | ........... | C07D 213/55 |
| WO | WO-2011/046851 A1 | 4/2011 | | |
| WO | WO-2013/167554 A1 | 11/2013 | | |
| WO | WO-2014/171762 A1 | 10/2014 | | |
| WO | WO 2015-097713 | 7/2015 | ........... | C07D 491/08 |

OTHER PUBLICATIONS

Ferdaoussi PhD, M. (2012) "Free fatty acid receptor 1: A new drug target for type 2 diabetes?", *Can J Diabetes*, 36:275-280.

Rajkumar J, (2013) "An overview of emerging pharmacological targets in treatment of type 2 diabetes mellitus." *Journal of Drug Discovery and Therapeutics*, 1(7):53-62.

Telvekar, V., (2008) "GPR40 carboxylic acid receptor family and diabetes: A new drug Target." *Current Drug Targets*, 9:899-910.

International Search Report (ISR) in PCT/KR2015/010976, dated Jul. 26, 2016 published in WO 2016/060517.

Extended European Search Report, European Application No. EP 15850582.6, dated Feb. 9, 2018.

Office Action from corresponding Chinese Patent Application No. 201580050675.X dated Sep. 5, 2018.

Office Action from corresponding Russian Patent Application No. 2017113130, dated Apr. 20, 2018, and it's English translation.

Search Report from corresponding Russian Patent Application No. 2017113130, dated Apr. 20, 2018, and it's English translation.

Office Action from corresponding Japanese Patent Application No. 2017-515685, dated Mar. 20, 2018.

\* cited by examiner

COMPOSITE PREPARATION, CONTAINING NOVEL 3-(4--(BENZYLOXY)PHENYL)HEX-4-INOIC ACID DERIVATIVE AND ANOTHER ACTIVE INGREDIENT, FOR PREVENTING OR TREATING METABOLIC DISEASES

CROSS-REFERENCE TO RELATED APPLICATIONS

This application is a national phase application of PCT Application No. PCT/KR2015/010976, filed on 16 Oct. 2015, which claims the benefit and priority to Korean Patent Application No. 10-2014-0141216, filed 17 Oct. 2014. The entire disclosures of the applications identified in this paragraph are incorporated herein by references.

FIELD

The present invention relates to a pharmaceutical composition for the prevention or treatment of metabolic diseases, in which a novel 3-(4-(benzyloxy)phenyl)hex-4-ynoic acid derivative and at least one selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based drugs can be administered, as different active ingredients, in combination or in the form of a composite preparation.

BACKGROUND

Diabetes is a serious disease that continually threatens our health and at least a hundred million people have been suffering over the world. Diabetes can be classified into two clinical symptom categories, which are type I diabetes and type II diabetes. Type I diabetes, also known as insulin-dependent diabetes mellitus (IDDM), is caused by autoimmune destruction of pancreatic beta cells that produce insulin, so that it requires regular administration of exogenous insulin. Type II diabetes, also known as non insulin-dependent diabetes mellitus (NIDDM), results from a defect in regulating blood sugar. So, those people who have type II diabetes characteristically show a defect in insulin secretion or insulin resistance, suggesting that they hardly have effective insulin secreted in vivo or cannot utilize insulin efficiently.

Diabetes is characterized by a high concentration of glucose in blood and urine, by which this disease causes polyuria, thirst, hunger, and other lipid and protein metabolism related problems. Diabetes can cause life threatening complications, such as vision loss, renal failure, and heart disease. Diabetes is also a cause of retinal damage, and increases the risk of cataract and glaucoma. Diabetes also lowers response to the pain relating to nerve injury in legs and feet and can be a cause of significant infection.

Recent drugs to treat diabetes are insulin, insulin-secretagogue, glucose lowering effector, peroxisome proliferator-activated receptor activator, etc. However, recent treatment methods have problems of inducing low blood sugar, increasing body weight, losing reactivity to the treatment drug over time, causing gastro-intestinal tract problems and edema, etc. Therefore, studies have been undergoing to introduce a more effective and efficient treatment method. One of those attempts is to use G-protein coupled receptor (GPCR).

GPR40 has recently been identified as one of G-protein coupled receptors (GPCR). It is known as free fatty acid receptor I, which is over-expressed in p-cells in the pancreas. Intracellular calcium concentration is increased by a compound that activates GPR40 (FFAR1) and accordingly glucose-stimulated insulin secretion (GSIS) is promoted (non-patent document 1). When the GPR40 activator was introduced in a normal mouse or a transgenic mouse being apt to have diabetes and a glucose tolerance test followed, it showed increased glucose tolerance. The treated mouse demonstrated a short-term increase of insulin in blood plasma. It was confirmed from the study on the functions of GPR40 that free fatty acid, which is the ligand of GPR40, was acting in pancreatic p cells, and as a result the p cells secreted insulin glucose concentration dependently. From the analysis with GPR knockout mouse, it was confirmed that GPR40 was involved in obesity and diabetes (non-patent document 2). Therefore, GPR40 is regarded as a novel target of a diabetes study.

Thus, the present inventors verified that the co-treatment with a novel 3-(4-(benzyloxy)phenyl)hex-4-ynoic acid derivative and at least one selected from the group consisting of dipeptidyl peptide IV (dipeptidyl peptidase-4, DPPIV) inhibitor-based, sulfonylurea-based, thiazolidinedione (TZD)-based, biguanide-based, and sodium/glucose cotransporter 2 (SGLT2) inhibitor-based drugs, as different active ingredients, exhibited an excellent blood glucose lowering effect, and then completed the present invention.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

PRIOR ART DOCUMENTS (Non-patent document 0001) Current Drug Targets, 2008, 9, 899-910
(Non-patent document 0002) Can J Diabetes 2012, 36, 275-280

DETAILED DESCRIPTION

Technical Problem

An aspect of the present invention is to provide a pharmaceutical composition for the prevention or treatment of metabolic diseases, in which a novel 3-(4-(benzyloxy)phenyl)hex-4-ynoic acid derivative, an optical isomer, hydrate, or solvate thereof, or a pharmaceutically acceptable salt thereof, and at least one selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based drugs can be administered, as different active ingredients, in combination or in the form of a composite preparation.

Other purposes and advantages of the present invention will become more obvious with the following detailed description of the invention, claims, and

DRAWINGS

Technical Solution

In accordance with an aspect of the present invention, there is provided a composition for the prevention or treatment of metabolic diseases, the composition containing: (a), as a first active ingredient, a compound represented by formula 1, an optical isomer, hydrate, or solvate thereof, or a pharmaceutically acceptable salt thereof, as a first active ingredient; and (b), as a second active ingredient, at least one compound selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based compounds:

[Formula 1]

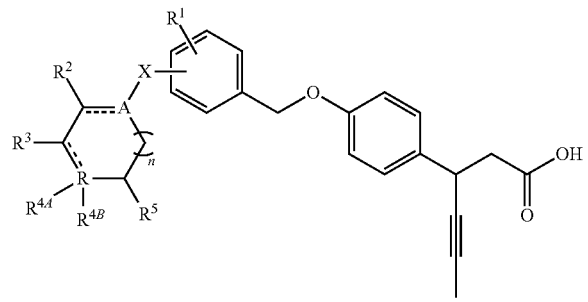

(In formula 1,

⸺ is a single bond or double bond;

A and E are each independently C, N, or O;

n is an integer of 0-5;

X is a single bond, or $C_{1-10}$ straight or branched alkylene;

$R^1$ is —H, —OH, halogen, $C_{1-10}$ straight or branched alkyl, $C_{1-10}$ straight or branched alkoxy, $C_{5-10}$ cycloalkyl, or $C_{5-10}$ cycloalkenyl;

$R^2$, $R^3$, and $R^5$ are independently —H, —OH, halogen, $C_{1-10}$ straight or branched alkyl, or $C_{1-10}$ straight or branched alkoxy, wherein, $R^2$ and $R^3$, together with the atoms to which they are attached, may form $C_{5-10}$ cycloalkyl, $C_{6-10}$ aryl, 5-10 membered heterocycloalkyl containing at least one hetero atom selected from the group consisting of N, O, and S, or 5-10 membered heteroaryl containing at least one hetero atom selected from the group consisting of N, O, and S;

$R^{4A}$ is —H, —OH, =O, unsubstituted or substituted $C_{6-10}$ aryl, or unsubstituted or substituted $C_{5-10}$ heteroaryl containing at least one hetero atom selected from the group consisting of N, O, and S, wherein, the substituted $C_{6-10}$ aryl and the substituted $C_{5-10}$ heteroaryl may be independently substituted with at least one substituent selected from the group consisting of —OH, halogen, nitrile, $C_{1-5}$ straight or branched chain alkyl unsubstituted or substituted with at least one halogen atom, $C_{1-5}$ straight or branched chain alkoxy unsubstituted or substituted with at least one halogen atom, $C_{1-10}$ straight or branched chain alkyl sulfonyl,

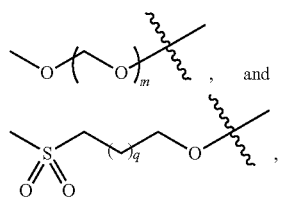 and and here, m and q are independently an integer of 1-10, also, phenyl may be fused to the unsubstituted or substituted $C_{5-10}$ heteroaryl, wherein, $R^3$ and $R^{4A}$, together with the atoms to which they are attached, may form $C_{5-10}$ cycloalkyl, $C_{6-10}$ aryl, 5-10 membered heterocycloalkyl containing at least one hetero atom selected from the group consisting of N, O, and S, or 5-10 membered heteroaryl containing at least one hetero atom selected from the group consisting of N, O, and S, also, the $C_{5-10}$ cycloalkyl, $C_{6-10}$ aryl, 5-10 membered heterocycloalkyl, and 5-10 membered heteroaryl may be independently substituted with $C_{1-5}$ straight or branched chain alkoxy; and $R^{4B}$ is absent, or $R^{4B}$, together with the atoms to which $R^{4B}$ is attached and $R^{4A}$ may form a $C_{5-10}$ hetero ring containing at least one hetero atom selected from the group consisting of N, O, and S.)

Here, the dipeptidyl peptidase IV inhibitor-based compound may include sitagliptin, vildagliptin, saxagliptin, linagliptin, teneligliptin, alogliptin, gemigliptin, dutogliptin, berberine, lupeol, red alder, and dandelion coffee, and the sulfonyl urea-based compound is any one selected from the group consisting of carbutamide, acetohexamide, chlorpropamide, tolbutamide, glipizide, gliclazide, glibenclamide, glibornuride, gliquidone, glisoxepide, glyclopyramide, and glimepiride.

The thiazolidinedione-based compound may be any one selected from the group consisting of rosiglitazone, pioglitazone, troglitazone, netoglitazone, rivoglitazone, ciglitazone, and rhodanine, and the biguanide-based compound may be any one selected from the group consisting of metformin, phenformin, buformin, proguanil, chlorproguanil, chlorhexidine, polyaminopropyl biguanide (PAPB), polihexanide, and alexidine.

The sodium/glucose cotransporter 2 (SGLT2) inhibitor-based compound is any one selected from the group consisting of empagliflozin, canagliflozin, and dapagliflozin.

In accordance with another aspect of the present invention, there is provided a method for the prevention or treatment of metabolic diseases, the method including administering, to a subject, a pharmaceutically effective amount of a composition containing: (a), as a first active ingredient, a compound represented by formula 1, an optical isomer, hydrate, or solvate thereof, or a pharmaceutically acceptable salt thereof; and (b), as a second active ingredient, at least one compound selected from the group consisting of dipeptidyl peptidase-IV (DPP-IV) inhibitor-based, sulfonylurea-based, thiazolidinedione (TZD)-based, biguanide-based, and sodium/glucose cotransporter 2 (SGLT2) inhibitor-based compounds, as a second active ingredient:

[Formula 1]

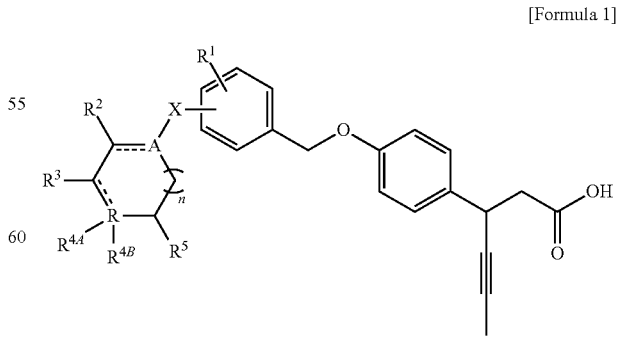

Here, Formula 1 is as described in the detailed description of the composition for the prevention or treatment of metabolic diseases.

The mixed composition of the first active ingredient and the second active ingredient is not particularly limited to the mixing weight ratio since no side effects or reduced efficacy are caused by the mixing weight ratio, and considering pathological conditions of patients, the known characteristics of the second active ingredient, and the like, the first active ingredient and the second active ingredient may be mixed at appropriate amounts and administered in combination. In an embodiment, the mixing weight ratio is 0.03:1 to 100:1. In another embodiment, the mixing weight ratio is 0.03:1 to 30:1, and in still another embodiment, the mixing weight ratio is 0.03:1 to 10:1.

Advantageous Effects

The combined treatment of a novel 3-(4-(benzyloxy) phenyl)hex-4-ynoic acid derivative, an optical isomer, hydrate, or solvate thereof, or a pharmaceutically acceptable salt thereof and at least one selected from the group consisting of dipeptidyl peptides IV (DPPIV) inhibitor-based, sulfonylurea-based, thiazolidinedione (TZD)-based, biguanide-based, and sodium/glucose cotransporter 2 (SGLT2) inhibitor-based drugs, as different active ingredients, showed a significantly excellent blood glucose-lowering effect in various animal diabetic diseases, and therefore, the composition of the present invention, in which the derivative, the optical isomer, hydrate, or solvate thereof, or the pharmaceutically acceptable salt thereof and at least one selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based drugs can be administered, as different active ingredients, in combination or in the form of a composite preparation, can be advantageously used as a pharmaceutical composition for the prevention or treatment of metabolic diseases, such as obesity, type I diabetes, type I diabetes, impaired glucose tolerance, insulin resistance syndrome, hyperglycemia, hyperlipidemia, hypertriglyceridemia, hypercholesterolemia, dyslipidemia, and syndrome X.

MODE FOR CARRYING OUT THE INVENTION

Figure 1:
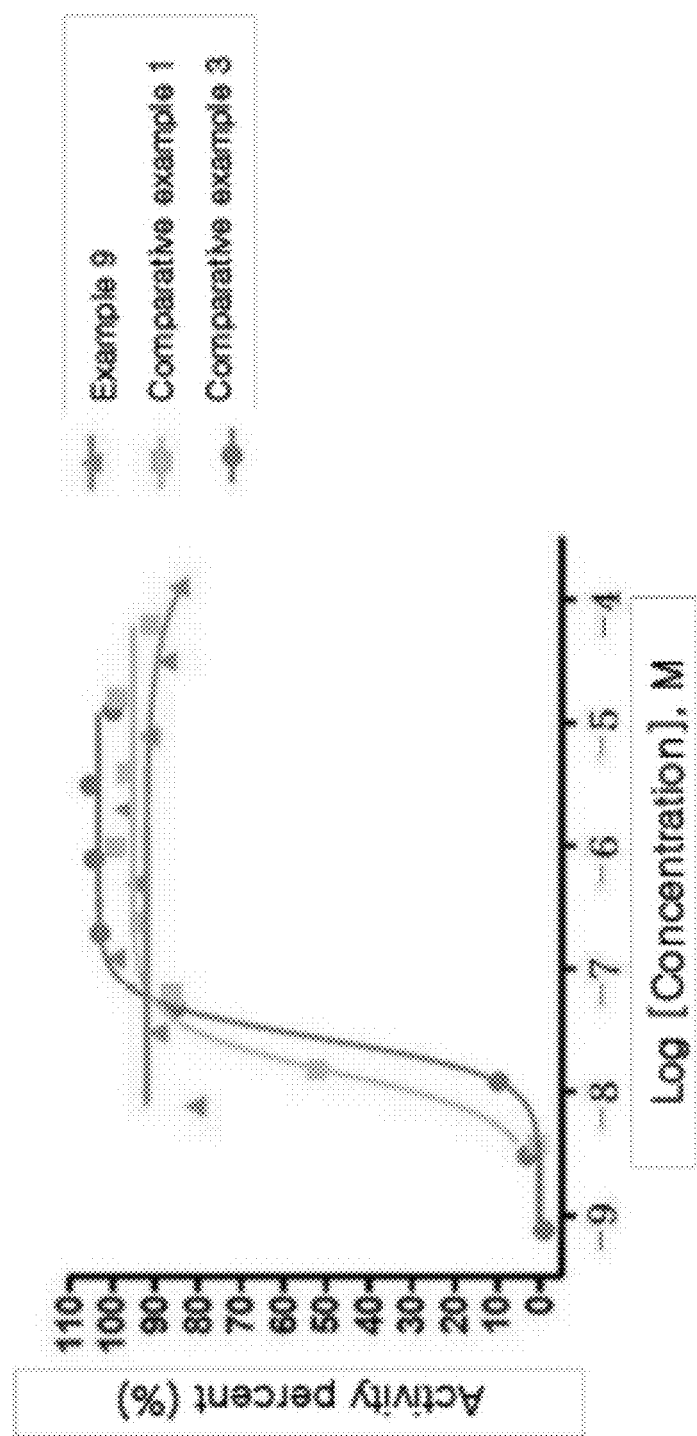
FIG. 1 is a graph illustrating the GPR40 protein activation pattern measured according to the concentrations of the compounds of Example 9, Comparative Example 1, and Comparative Example 3.

Hereinafter, the present invention will be described in detail.

In accordance with an aspect of the present invention, there is provided a composition for the prevention or treatment of metabolic diseases, the composition containing: (a), as a first active ingredient, a compound represented by formula 1, an optical isomer, hydrate, or solvate thereof, or a pharmaceutically acceptable salt thereof, as a first active ingredient; and (b), as a second active ingredient, at least one compound selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based compounds:

[Formula 1]

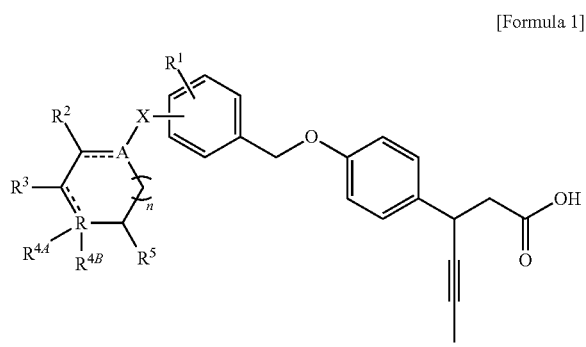

(In formula ═══ is a single bond or double bond; A and E are each independently C, N, or O; n is an integer of 0-5; X is a single bond, or $C_{1-10}$ straight or branched alkylene;

$R^1$ is —H, —OH, halogen, $C_{1-10}$ straight or branched alkyl, $C_{1-10}$ straight or branched alkoxy, $C_{5-10}$ cycloalkyl, or $C_{5-10}$ cycloalkenyl;

$R^2$, $R^3$, and $R^5$ are independently —H, —OH, halogen, $C_{1-10}$ straight or branched alkyl, or $C_{1-10}$ straight or branched alkoxy, wherein, $R^2$ and $R^3$, together with the atoms to which they are attached, may form $C_{5-10}$ cycloalkyl, $C_{6-10}$ aryl, 5-10 membered heterocycloalkyl containing at least one hetero atom selected from the group consisting of N, O, and S, or 5-10 membered heteroaryl containing at least one hetero atom selected from the group consisting of N, O, and S;

$R^{4A}$ is —H, —OH, =O, unsubstituted or substituted $C_{6-10}$ aryl, or unsubstituted or substituted $C_{5-10}$ heteroaryl containing at least one hetero atom selected from the group consisting of N, O, and S, wherein, the substituted $C_{6-10}$ aryl and the substituted $C_{5-10}$ heteroaryl may be independently substituted with at least one substituent selected from the group consisting of —OH, halogen, nitrile, $C_{1-5}$ straight or branched chain alkyl unsubstituted or substituted with at least one halogen atom, $C_{1-5}$ straight or branched chain alkoxy unsubstituted or substituted with at least one halogen atom, $C_{1-10}$ straight or branched chain alkyl sulfonyl,

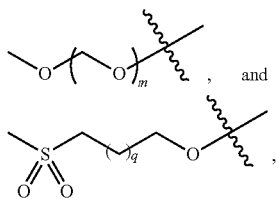, and and here, m and q are independently an integer of 1-10, also, phenyl may be fused to the unsubstituted or substituted $C_{5-10}$ heteroaryl, wherein, $R^3$ and $R^{4A}$, together with the atoms to which they are attached, may form $C_{5-10}$ cycloalkyl, $C_{6-10}$ aryl, 5-10 membered heterocycloalkyl containing at least one hetero atom selected from the group consisting of N, O, and S, or 5-10 membered heteroaryl containing at least one hetero atom selected from the group consisting of N, O, and S, also, the $C_{5-10}$ cycloalkyl, $C_{6-10}$ aryl, 5-10 membered heterocycloalkyl, and 5-10 membered heteroaryl may be independently substituted with $C_{1-5}$ straight or branched chain alkoxy; and $R^{4B}$ is absent, or $R^{4B}$, together with the atoms to which $R^{4B}$ is attached and $R^{4A}$ may form a $C_{5-10}$ hetero ring containing at least one hetero atom selected from the group consisting of N, O, and S).

In an embodiment of the present invention,
 --- is a single bond or double bond;
A and E are independently C, N, or O;
n is an integer of 0-3;
X is a single bond, or $C_{1-5}$ straight or branched alkylene;
$R^1$ is —H, —OH, halogen, $C_{1-5}$ straight or branched alkyl, $C_{1-5}$ straight or branched alkoxy, $C_{5-8}$ cycloalkyl, or $C_{5-8}$ cycloalkenyl;
$R^2$, $R^3$, and $R^5$ are independently —H, —OH, halogen, $C_{1-5}$ straight or branched alkyl, or $C_{1-5}$ straight or branched alkoxy,
wherein, $R^2$ and $R^3$, together with the atoms to which they are attached, may form $C_{5-8}$ cycloalkyl, $C_{6-8}$ aryl, 5-8 membered heterocycloalkyl containing at least one hetero atom selected from the group consisting of N, O, and S, or 5-8 membered heteroaryl containing at least one hetero atom selected from the group consisting of N, O, and S;
$R^{4A}$ is —H, —OH, =O, unsubstituted or substituted C-s aryl, or unsubstituted or substituted $C_{5-8}$ heteroaryl containing at least one hetero atom selected from the group consisting of N, O, and S, wherein, the substituted $C_{6-8}$ aryl and the substituted $C_{5-8}$ heteroaryl may be independently substituted with at least one substituent selected from the group consisting of —OH, halogen, nitrile, $C_{1-5}$ straight or branched chain alkyl unsubstituted or substituted with at least one halogen atom, $C_{1-5}$ straight or branched chain alkoxy unsubstituted or substituted with at least one halogen atom, $C_{1-8}$ straight or branched chain alkyl sulfonyl,

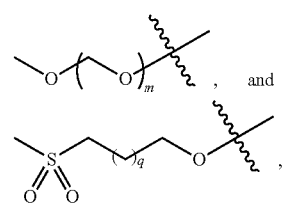, and and here, m and q are independently an integer of 1-5, also, phenyl may be fused to the unsubstituted or substituted $C_{5-8}$ heteroaryl, wherein, $R^3$ and $R^{4A}$, together with the atoms to which they are attached, may form $C_{5-8}$ cycloalkyl, $C_{6-8}$ aryl, 5-8 membered heterocycloalkyl containing at least one hetero atom selected from the group consisting of N, O, and S, or 5-8 membered heteroaryl containing at least one hetero atom selected from the group consisting of N, O, and S;

also, the $C_{5-8}$ cycloalkyl, $C_{6-8}$ aryl, 5-8 membered heterocycloalkyl, and 5-8 membered heteroaryl may be independently substituted with $C_{1-5}$ straight or branched chain alkoxy; and $R^{4B}$ is absent, or $R^{4B}$, together with the atoms to which $R^{4B}$ is attached and $R^{4A}$, may form a $C_{5-8}$ hetero ring containing at least one hetero atom selected from the group consisting of N, O, and S.)

In an embodiment of the present invention,
 --- is a single bond or double bond;
A and E are independently C or N;
n is an integer of 0-1;
X is a single bond, or $C_{1-3}$ straight or branched alkylene;
$R^1$ is —H or

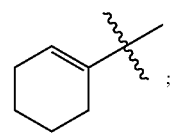 [SMILES: *C1=CCCCC1];

$R^2$, $R^3$, and $R^5$ are independently —H,
wherein, $R^2$ and $R^3$, together with the atoms to which they are attached, may form phenyl;
$R^{4A}$ is —H, —OH, =O,

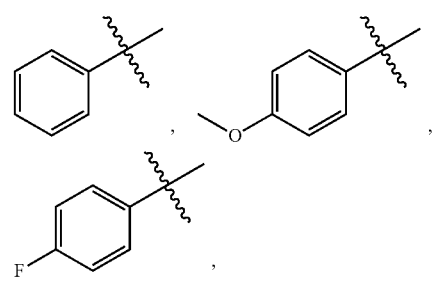

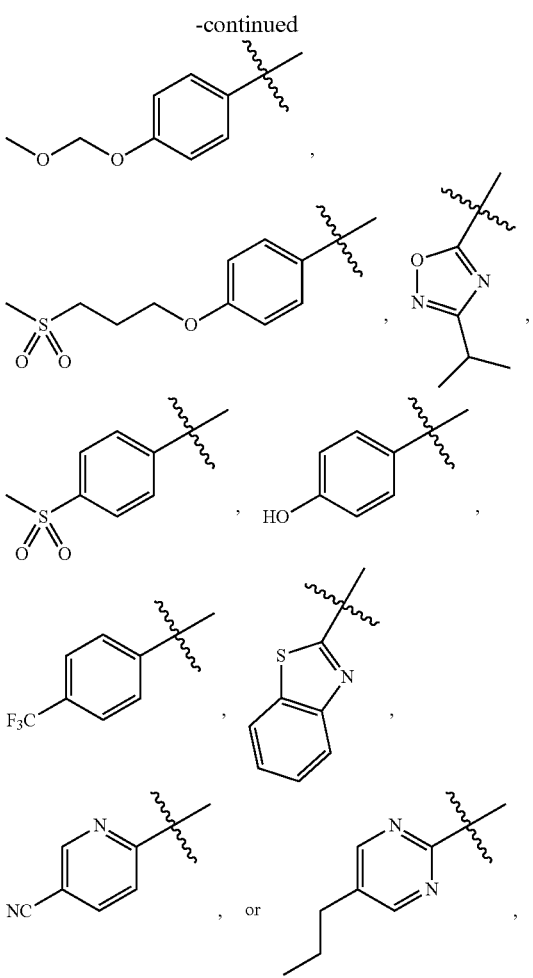

wherein, R³ and R⁴ᴬ, together with the atoms to which they are attached, may form phenyl, and the phenyl may be substituted with a methoxy group; and R⁴ᴮ is absent, or R⁴ᴮ, together with the atoms to which R⁴ᴮ is attached and R⁴ᴬ, may form

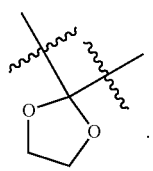 [SMILES: *C1(*)OCCO1]

In an embodiment of the present invention, the compound represented by formula 1 is any one selected from the following compound group:
(1) 3-(4-(3-(1,4-dioxaspiro[4.5]dec-7-en-8-yl)benzyloxy)phenyl)hex-4-ynoic acid;
(2) L-lysine 3-(4-(3-(1,4-dioxaspiro[4.5]dec-7-en-8-yl)benzyloxy)phenyl)hex-4-ynoate;
(3) 4-(4-(3-(1,4-dioxaspiro[4.5]dec-7-en-8-yl)benzyloxy)phenyl)hex-4-ynoic acid;
(4) 3-(4-(3-(4-oxocyclohex-1-enyl)benzyloxy)phenyl)hex-4-ynoic acid;
(5) 3-(4-(3-(4-hydroxycyclohex-1-enyl)benzyloxy)phenyl)hex-4-ynoic acid;
(6) L-lysine 3-(4-(3-(4-hydroxycyclohex-1-enyl)benzyloxy)phenyl)hex-4-ynoate;
(7) (3S)-3-(4-(3-(1,4-dioxaspiro[4.5]dec-7-en-8-yl)benzyloxy)phenyl)hex-4-ynoic acid;
(8) (3R)-3-(4-(3-(1,4-dioxaspiro[4.5]dec-7-en-8-yl)benzyloxy)phenyl)hex-4-ynoic acid;
(9) L-lysine (3S)-3-(4-(3-(1,4-dioxaspiro[4.5]dec-7-en-8-yl)benzyloxy)phenyl)hex-4-ynoate;
(10) L-lysine (3R)-3-(4-(3-(1,4-dioxaspiro[4.5]dec-7-en-8-yl)benzyloxy)phenyl)hex-4-ynoate;
(11) sodium (3S)-3-(4-(3-(1,4-dioxaspiro[4.5]dec-7-en-8-yl)benzyloxy)phenyl)hex-4-ynoate;
(12) 3-(4-(4-((3,4-dihydroisoquinolin-2(1H)-yl)methyl)benzyloxy)phenyl)hex-4-ynoic acid;
(13) 3-(4-(3-cyclohexenyl-4-((3,4-dihydroisoquinolin-2(1H)-yl)methyl)benzyloxy)phenyl)hex-4-ynoic acid;
(14) 3-(4-(4-((4-phenyl-5,6-dihydropyridin-1(2H)-yl)methyl)benzyloxy)phenyl)hex-4-ynoic acid;
(15) 3-(4-(4-((4-phenylpiperazin-1-yl)methyl)benzyloxy)phenyl)hex-4-ynoic acid;
(16) 3-(4-(4-((6-methoxy-3,4-dihydroisoquinolin-2(1H)-yl)methyl)benzyloxy)phenyl)hex-4-ynoic acid;
(17) 3-(4-(4-((4-phenylpiperidin-1-yl)methyl)benzyloxy)phenyl)hex-4-ynoic acid;
(18) 3-(4-(4-((4-(4-fluorophenyl)piperazin-1-yl)methyl)benzyloxy)phenyl)hex-4-ynoic acid;
(19) 3-(4-(4-((4-(4-(trifluoromethyl)phenyl)piperazin-1-yl)methyl)benzyloxy)phenyl)hex-4-ynoic acid;
(20) 3-(4-(4-((4-(4-(3-(methylsulfonyl)propoxy)phenyl)piperazin-1-yl)methyl)benzyloxy)phenyl)hex-4-ynoic acid;
(21) (S)-3-(4-(4-((3,4-dihydroisoquinolin-2(1H)-yl)methyl)benzyloxy)phenyl)hex-4-ynoic acid;
(22) (S)-3-(4-(4-((4-(4-(trifluoromethyl)phenyl)piperazin-1-yl)methyl)benzyloxy)phenyl)hex-4-ynoic acid;
(23) (S)-3-(4-(4-((4-(4-fluorophenyl)piperazin-1-yl)methyl)benzyloxy)phenyl)hex-4-ynoic acid;
(24) potassium (S)-3-(4-(4-((4-(4-(trifluoromethyl)phenyl)piperazin-1-yl)methyl)benzyloxy)phenyl)hex-4-ynoate;
(25) (S)-3-(4-(4-((6-methoxy-3,4-dihydroisoquinolin-2(1H)-yl)methyl)benzyloxy)phenyl)hex-4-ynoic acid;
(26) (S)-3-(4-(4-((4-phenylpiperidin-1-yl)methyl)benzyloxy)phenyl)hex-4-ynoic acid;
(27) (S)-3-(4-(4-(isoindolin-2-ylmethyl)benzyloxy)phenyl)hex-4-ynoic acid;
(28) (S)-3-(4-(4-((4-phenyl-5,6-dihydropyridin-1(2H)-yl)methyl)benzyloxy)phenyl)hex-4-ynoic acid;
(29) (S)-3-(4-(4-((4-(4-(methoxymethoxy)phenyl)piperazin-1-yl)methyl)benzyloxy)phenyl)hex-4-ynoic acid;
(30) (S)-3-(4-(4-((4-(5-isopropyl-1,2,4-oxadiazol-3-yl)piperidin-1-yl)methyl)benzyloxy)phenyl)hex-4-ynoic acid;
(31) (S)-3-(4-(4-((4-(5-isopropyl-1,2,4-oxadiazol-3-yl)piperazin-1-yl)methyl)benzyloxy)phenyl)hex-4-ynoic acid;
(32) (S)-3-(4-(4-((4-(4-(methylsulfonyl)phenyl)-5,6-dihydropyridin-1(2H)-yl)methyl)benzyloxy)phenyl)hex-4-ynoic acid;
(33) (S)-3-(4-(4-((4-(4-(3-(methylsulfonyl)propoxy)phenyl)-5,6-dihydropyridin-1(2H)-yl)methyl)benzyloxy)phenyl)hex-4-ynoic acid;
(34) (3S)-3-(4-(4-(1-(3,4-dihydroisoquinolin-2(1H)-yl)ethyl)benzyloxy)phenyl)hex-4-ynoic acid;
(35) (S)-3-(4-(4-((4-(4-hydroxyphenyl)piperazin-1-yl)methyl)benzyloxy)phenyl)hex-4-ynoic acid;
(36) (S)-3-(4-(4-((4-(4-(3-(methylsulfonyl)propoxy)phenyl)piperazin-1-yl)methyl)benzyloxy)phenyl)hex-4-ynoic acid;
(37) sodium (S)-3-(4-(4-(isoindolin-2-ylmethyl)benzyloxy)phenyl)hex-4-ynoate;
(38) L-lysine (S)-3-(4-(4-(isoindolin-2-ylmethyl)benzyloxy)phenyl)hex-4-ynoate;

(39) (S)-3-(4-(4-((4-(4-fluorophenyl)-5,6-dihydropyridin-1 (2H)-yl)methyl)benzyloxy)phenyl)hex-4-ynoic acid;
(40) (S)-3-(4-(4-((4-(4-methoxyphenyl)piperazin-1-yl) methyl)benzyloxy)phenyl)hex-4-ynoic acid;
(41) sodium (S)-3-(4-(4-((3,4-dihydroquinolin-1(2H)-yl) methyl)benzyloxy)phenyl)hex-4-ynoate;
(42) potassium (S)-3-(4-(4-((3,4-dihydroquinolin-1(2H)-yl) methyl)benzyloxy)phenyl)hex-4-ynoate;
(43) (S)-3-(4-(4-((4-(benzo[d]thiazol-2-yl)piperazin-1-yl) methyl)benzyloxy)phenyl)hex-4-ynoic acid;
(44) (S)-3-(4-(4-((4-(5-propylpyrimidin-2-yl)piperazin-1-yl)methyl)benzyloxy)phenyl)hex-4-ynoic acid;
(45) (S)-3-(4-(4-((4-(5-cyanopyridin-2-yl)piperazin-1-yl) methyl)benzyloxy)phenyl)hex-4-ynoic acid;
(46) (3S)-3-(4-(4-((3-phenylpyrrolidin-1-yl)methyl)benzyloxy)phenyl)hex-4-ynoic acid;
(47) sodium (S)-3-(4-(3-(4-(4-methoxyphenyl)piperazin-1-yl)benzyloxy) phenyl)hex-4-ynoate;
(48) (S)-3-(4-(4-(2-(6-methoxy-3,4-dihydroisoquinolin-2 (1H)-yl)ethyl)benzyloxy)phenyl)hex-4-ynoic acid;
(49) (S)-3-(4-(4-(2-(isoindolin-2-yl)ethyl)benzyloxy)phenyl)hex-4-ynoic acid;
(50) (S)-3-(4-(4-(2-(3,4-dihydroisoquinolin-2(1H)-yl)ethyl) benzyloxy)phenyl)hex-4-ynoic acid; and
(51) sodium (S)-3-(4-(4-((6-methoxy-3,4-dihydroisoquinolin-2(1H)-yl)methyl)benzyloxy)phenyl)hex-4-ynoate.

The compound represented by formula 1 of the present invention may be used in the form of a pharmaceutically acceptable salt, in which the salt is usefully an acid addition salt formed by a pharmaceutically acceptable free acid. The acid addition salt is obtained from: inorganic acids, such as hydrochloric acid, nitric acid, phosphoric acid, sulfuric acid, hydrobromic acid, hydriodic acid, nitrous acid, and phosphorous acid; non-toxic organic acids, such as aliphatic mono and dicarboxylate, phenyl-substituted alkanoate, hydroxy alkanoate and alkane dioate, aromatic acids, and aliphatic and aromatic sulfonic acids; or organic acids, such as acetic acid, benzoic acid, citric acid, lactic acid, maleic acid, gluconic acid, methanesulfonic acid, 4-toluenesulfonic acid, tartaric acid, and fumaric acid. Examples of the pharmaceutically non-toxic salt include sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1, 4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, p-hydroxybutylate, glycolate, malate, tartrate, methanesulfonate, propanesulfonate, naphthalene-1-sulfonate, naphthalene-2-sulfonate, and mandelate.

The acid addition salt of the present invention may be prepared by a conventional method, and for example, the acid addition salt may be prepared by dissolving the derivative of formula 1 in an organic solvent, such as methanol, ethanol, acetone, methylene chloride, or acetonitrile, adding an organic acid or inorganic acid thereto to generate a precipitate, and then filtering and drying the precipitate, or may be prepared by distilling a solvent and an excess acid under reduced pressure, followed by drying and crystallization in an organic solvent.

In addition, a pharmaceutically acceptable metal salt may be prepared by using a base. For example, an alkali metal or alkaline earth metal salt is obtained by dissolving the compound in an excessive alkali metal hydroxide or alkaline earth metal hydroxide solution, filtering a non-soluble compound salt, and then evaporating and drying the filtrate. Here, as the metal salt, a sodium, potassium, or calcium salt is preferably prepared from a pharmaceutical aspect. In addition, the corresponding salt is obtained by reacting an alkali metal or alkaline earth metal salt with a suitable salt (e.g., silver nitrate).

Furthermore, a pharmaceutically acceptable salt may be prepared by using an amino acid in which an amino group is attached to an organic acid, and, as the amino acid salt, a natural amino acid, such as glycine, alanine, phenylalanine, valine, lysine, or glutamic acid, is preferably prepared from a pharmaceutical aspect, and L-lysine is most preferably prepared from a pharmaceutical aspect.

In addition, the present invention includes not only the compound represented by formula 1 and the pharmaceutically acceptable salt thereof but also a solvate, an optical isomer, a hydrate, and the like, which may be prepared therefrom.

The pharmaceutical composition of the present invention may contain a pharmaceutically acceptable carrier in addition to active ingredients. The pharmaceutically acceptable carrier contained in the pharmaceutical composition of the present invention is conventionally used in the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in Remington's Pharmaceutical Sciences (19th ed., 1995).

In addition, the effective dose of the compound of the present invention on the human body may vary depending on the age, body weight, sex, form of administration, health condition, and disease severity of a patient, and is generally about 0.001-100 mg/kg/day, and preferably 0.01-35 mg/kg/day. Based on an adult patient weighing 70 kg, the dose is generally 0.07-7000 mg/day, and preferably 0.7-2500 mg/day, and the dose may be administered once or several times a day at a predetermined time interval according to the judgment of a doctor or a pharmacist.

The pharmaceutical composition of the present invention may be administered orally or parenterally, and examples of the parenteral administration may include a topical application to skin, an intravenous injection, a subcutaneous injection, a muscular injection, an intraperitoneal injection, and a transdermal administration. The pharmaceutical composition of the present invention may be preferably administered orally. Examples of a solid preparation for oral administration include a tablet, a pill, a powder, a granule, a capsule, a troche, and the like, and such solid preparations are formulated by mixing one or more of the compounds of the present invention with at least one excipient, such as starch, calcium carbonate, sucrose or lactose, or gelatin. In addition to simple excipients, lubricants such as magnesium stearate and talc are also used. Examples of a liquid preparation for oral administration may include a suspension, a liquid for internal use, an emulsion, a syrup, and the like. In addition to commonly used simple diluents, such as water and liquid paraffin, various excipients, such as a wetting agent, a sweetener, an aroma, and a preservative may be included in the liquid preparation.

Examples of the preparation for oral administration include a sterilized aqueous solution, a non-aqueous solvent, a suspension solvent, an emulsion, a freeze-drying agent, and a suppository. As the non-aqueous solvent and the suspension solvent, propylene glycol, polyethylene glycol, a vegetable oil such as an olive oil, an injectable ester such as ethylolate, or the like may be used. As a substrate for the suppository, witepsol, macrogol, tween 61, cacao paper, laurin, glycerol, gelatin, and the like may be used.

The pharmaceutical composition of the present invention may be formulated using a pharmaceutically acceptable carrier and/or excipient according to a method which can be easily carried out by a person having ordinary skill in the art to which the present invention pertains, and may be prepared in a unit dosage form or may be prepared by being packaged in a multi-dose container. Here, the dosage form may be a solution in an oily or aqueous medium, a suspension, an emulsion, an extract, a powder, a granule, a tablet, or a capsule, and may further contain a dispersant or a stabilizer.

In an embodiment of the present invention, the dipeptidyl peptidase IV inhibitor-based compound is any one selected from the group consisting of sitagliptin, vildagliptin, saxagliptin, linagliptin, teneligliptin, alogliptin, gemigliptin, dutogliptin, berberine, lupeol, red alder, and dandelion coffee.

In an embodiment of the present invention, the sulfonyl urea-based compound is any one selected from the group consisting of carbutamide, acetohexamide, chlorpropamide, tolbutamide, glipizide, gliclazide, glibenclamide, glibornuride, gliquidone, glisoxepide, glyclopyramide, and glimepiride.

In an embodiment of the present invention, the thiazolidinedione-based compound is any one selected from the group consisting of rosiglitazone, pioglitazone, troglitazone, netoglitazone, rivoglitazone, ciglitazone, and rhodanine.

In an embodiment of the present invention, the e biguanide-based compound is any one selected from the group consisting of metformin, phenformin, buformin, proguanil, chlorproguanil, chlorhexidine, polyaminopropyl biguanide (PAPB), polihexanide, and alexidine.

In an embodiment of the present invention, the SGLT2 inhibitor-based compound is any one selected from the group consisting of empagliflozin, canagliflozin, and dapagliflozin.

In an embodiment of the present invention, the mixing weight ratio of the first active ingredient and the second active ingredient of the present invention is 0.03:1 to 100:1. In another embodiment, the mixing weight ratio is 0.03:1 to 30:1, and in still another embodiment, the mixing weight ratio is 0.03:1 to 10:1. However, the composition of the present invention is not particularly limited to the mixing weight ratio since no side effects or reduced efficacy are caused by the mixing weight ratio, and considering pathological conditions of patients, the known characteristics of the second active ingredient, and the like, the first active ingredient and the second active ingredient may be mixed at appropriate amounts and administered in combination.

In an embodiment of the present invention, the composition of the present invention activates G-protein receptor 40 (GPR40) enzyme. GPR40 is the G-protein coupled receptor (GPCR) that is mainly expressed in insulin secreting cells of the pancreas. The GPR40 expression profile has the potential usability for the treatment of various metabolic diseases including obesity and diabetes.

In the present invention, as a result of evaluating the activity of GPR40 receptor when a compound represented by formula 1, an optical isomer thereof, or a pharmaceutically acceptable salt thereof, as a first active ingredient, was used alone, it could be seen that the compounds of all the examples of the present invention activated the GPR40 receptor by 50% (EC50) at low concentrations, and thus, the activation effects of the compounds of the present invention were excellent (see Experimental Examples 1 and 2, and FIG. 1).

In addition, in the present invention, as a result of evaluating CYP enzyme inhibitory activity by the drug metabolisms of a compound represented by formula 1, an optical isomer thereof, or a pharmaceutically acceptable salt thereof, as a first active ingredient, it was verified that the compounds of the examples of the present invention had low CYP enzyme inhibitory activity, causing no toxicity due to the concentration at the time of the co-administration with other drugs, and thus, the compounds of the present invention could be co-administered with other drugs in the complication incidence (see Experimental Example 3).

Furthermore, in the present invention, as a result of conducting the oral glucose tolerance experiment of a compound represented by formula 1, an optical isomer thereof, or a pharmaceutically acceptable salt thereof, as a first active ingredient, it could be seen that the compounds of all the examples of the present invention showed similar or excellent blood sugar-lowering effects compared with a GPR40 activator that has been known in the conventional art, and thus, the compounds of the present invention had a significantly excellent effect in activating GPR40 in vivo (see Experimental Examples 4, 5, and 6).

Figure 2:
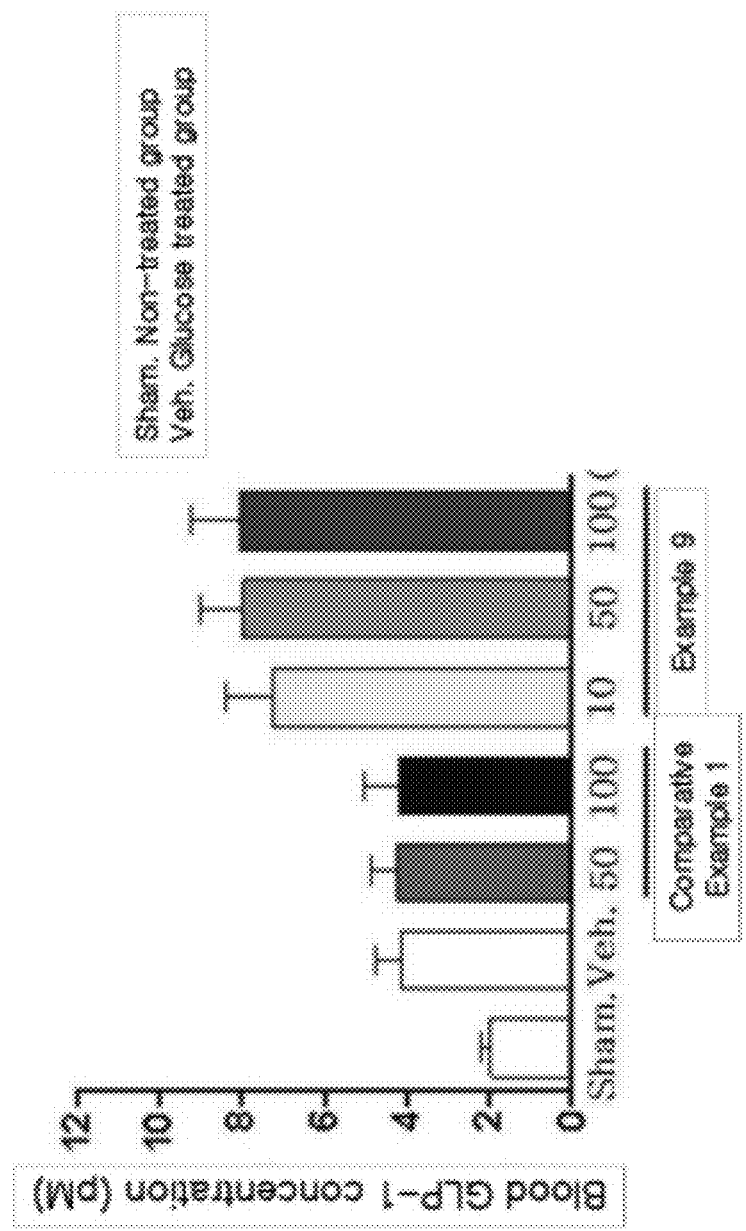
FIG. 2 is a graph illustrating the blood GLP-1 concentrations when Sprague Dawley (SD) rats were orally administered with the compounds of Example 9 and Comparative Example 1.

Furthermore, in the present invention, as a result of conducting an experiment for evaluating a blood GLP-1 concentration increase rate after the oral administration of a compound represented by formula 1, an optical isomer thereof, or a pharmaceutically acceptable salt thereof, as a first active ingredient, it was verified that, compared with a glucose treated group (Veh.), the compound of Comparative Example 1 showed no blood GLP-1 concentration increase effect after administration, but the compound of Example 9 increased the blood GLP-1 concentration when administered to SD rat (see Experimental Example 7, and FIG. 2).

Furthermore, it was verified that the co-administration of a novel 3-(4-(benzyloxy)phenyl)hex-4-ynoic acid derivative of the present invention and a representative drug, such as dipeptidyl peptidase IV (DPPIV) inhibitor-based, sulfonylurea-based, thiazolidinedione (TZD)-based, biguanide-based, and SGLT2 inhibitor-based drugs, had an excellent blood glucose-lowering effect compared with the administration of the drugs alone (see tables 8 to 14 in Experimental Examples 8 to 12, and FIGS. 3 to 12).

In short, the pharmaceutical composition of the present invention has an excellent effect of activating GPR40 protein, leading to an excellent insulin secretion promoting effect, and can be co-administered together with other drugs, and also, has a significantly excellent effect of activating GPR40 protein in vivo.

In an embodiment of the present invention, the metabolic disease is any one selected from the group consisting of obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X. The composition of the present invention can be advantageously used for the prevention or treatment of the above-mentioned metabolic diseases through the blood sugar-lowering effect thereof.

A method for preparing a compound represented by formula 1 of the present invention will be described as follows:

Preparation Method 1

A compound represented by formula 1 of the present invention may be prepared, as shown in Reaction Scheme 1 below, by including steps of: carrying out a condensation reaction of a compound represented by formula 2 and a compound represented by formula 3 to prepare a compound represented by formula 4 (Step 1); and carrying out a reduction reaction of the compound represented by formula 4 prepared in step 1 to prepare the compound represented by formula 1 (Step 2).

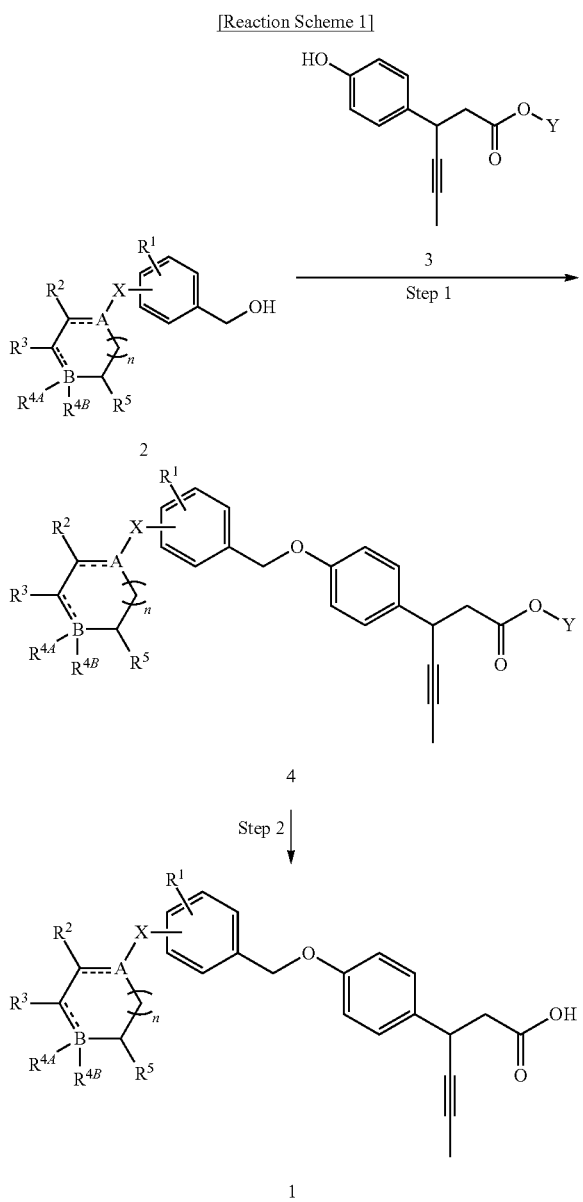

(wherein Reaction Scheme 1, $R^1$, $R^2$, $R^3$, $R^{4A}$, $R^{4B}$, R, A, E, n, and X are as defined in formula 1; and Y is $C_{1-10}$ straight or branched chain alkyl).

Hereinafter, the preparation method for the compound represented by formula 1 of the present invention will be described by steps in detail.

In the preparation method for the compound represented by formula 1 of the present invention, step 1) is to prepare a compound represented by formula 4 by carrying out a coupling reaction between a compound represented by formula 2 and a compound represented by formula 3. More specifically, the compound represented by formula 2, an azocarboxylate reagent is slowly added dropwise to a solution, in which the compound represented by formula 3, and triphenylphosphine are mixed, at a temperature of −5° C. to 10° C. to carry out the Mitsunobu reaction to give the compound represented by formula 4.

Here, as the azocarboxylate reagent, diethyl azodicarboxylate (DEAD) or diisopropyl azodicarboxylate (DIAD) may be used, and preferably diisopropyl azodicarboxylate (DIAD) may be used.

In addition, as the reaction solvent, tetrahydrofuran (THF), dichloromethane (DCM), toluene, or acetonitrile may be used, and preferably tetrahydrofuran (THF) may be used.

Furthermore, the reaction temperature is preferably carried out between 0° C. to the boiling point of the solvent, and the reaction time is not particularly limited, but the reaction may preferably be carried out for 0.5-10 hours.

In the preparation method for the compound represented by formula 1 of the present invention, step 2) is to prepare the compound represented by formula 1 by carrying out a reduction reaction of the compound represented by formula 4, prepared in step 1), in the presence of a base. More specifically, the compound represented by formula 4 prepared in step 1) is reacted with the base at room temperature to prepare the compound represented by formula 1 wherein an ester group contained in the compound represented by formula 4 is reduced into a carboxyl group.

Here, as the base, potassium hydroxide (KOH), sodium hydroxide (NaOH), or lithium hydroxide (LiOH) may be used, and preferably, potassium hydroxide (KOH) may be used.

In addition, as the reaction solvent, tetrahydrofuran (THF), dichloromethane (DCM), toluene, or acetonitrile may be used, and preferably tetrahydrofuran (THF) may be used.

Furthermore, the reaction temperature is preferably carried out between 0° C. to the boiling point of the solvent, and the reaction time is not particularly limited, but the reaction may preferably be carried out for 0.5-10 hours.

Preparation Method of Starting Material
(Compound Represented by Formula 2)

In the reaction formula 1 in the present invention, the compound represented by formula 2 used as a starting material may be prepared by the method including the following steps, as shown in Reaction Scheme 2 below:

reacting a compound represented by formula 8 with a compound represented by formula 9 to prepare a compound represented by formula 10 (step 1);

reacting the compound represented by formula 10 prepared in step 1) with a compound represented by formula 11 to prepare a compound represented by formula 12 (step 2); and carrying out a reduction reaction of the compound represented by formula 12 prepared in step 2) to prepare the compound represented by formula 2 (step 3).

[Reaction Scheme 2]

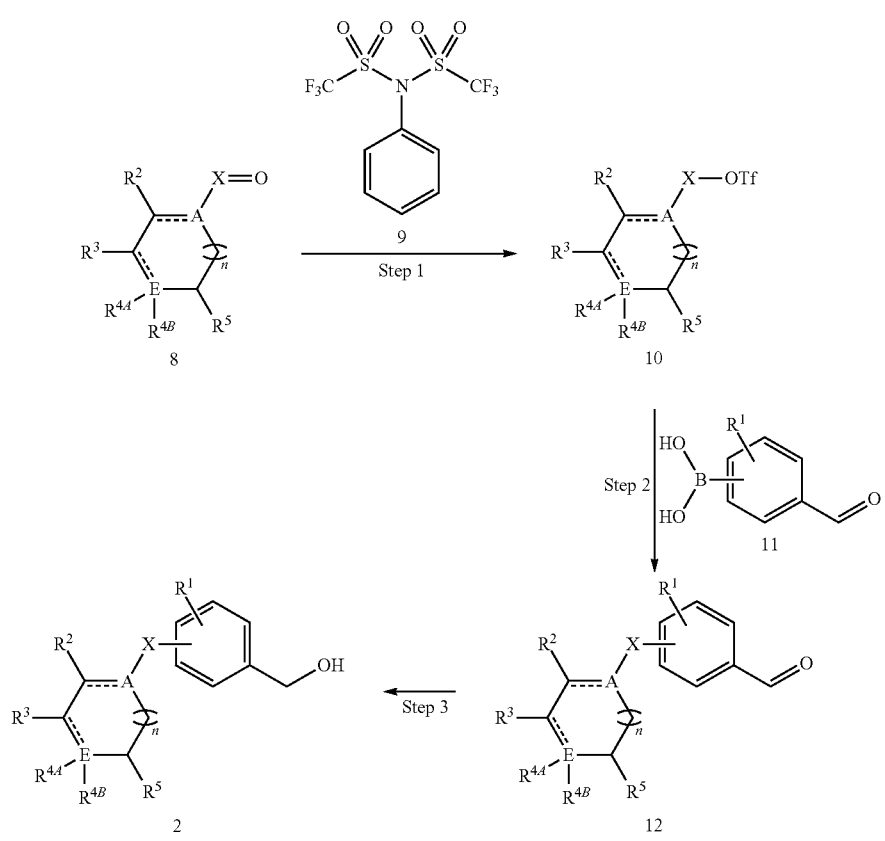

(wherein Reaction Scheme 2, $R^1$, $R^2$, $R^3$, $R^{4A}$, $R^{4B}$, $R^5$, A, E, n, and X are as defined in formula 1; and -OTf is a trifluoromethanesulfonate group).

Hereinafter, the preparation method for the compound represented by formula 2 of the present invention will be described by steps in detail.

In the preparation method for the compound represented by formula 2 of the present invention, step 1) is to prepare the compound represented by formula 10 by reacting a compound represented by formula 8 with a compound represented by formula 9. More specifically, the compound represented by formula 8 and the compound represented by formula 9 are dissolved in an organic solvent at −80° C. to −70° C., and then a bis(trimethylsilyl)amide metal complex is slowly added dropwise thereto, and the mixture was stirred while the temperature was raised to room temperature, thereby giving the compound represented by formula 10.

Here, as the bis(trimethylsilyl)amide metal complex, potassium bis(trimethylsilyl)amide, lithium bis(trimethylsilyl)amide, or sodium bis(trimethylsilyl)amide may be used, and preferably, potassium bis(trimethylsilyl)amide may be used.

In addition, as the organic solvent, tetrahydrofuran (THF), diethylether, diphenylether, diisopropylether (DIPE), dimethylformamide (DMF), dimethylacetamide (DMA), dimethylsulfoxide DMSO), dichloromethane (DCM), chlorobenzene, toluene, and benzene may be used.

Furthermore, the reaction temperature is preferably carried out between −80° C. to the boiling point of the solvent, and the reaction time is not particularly limited, but the reaction may preferably be carried out for 0.5-10 hours.

In the preparation method for the compound represented by formula 2 of the present invention, step 2) is to prepare the compound represented by formula 12 by reacting the compound represented by formula 10 prepared in step 1) with the compound represented by formula 11. More specifically, a Suzuki coupling reaction of the compound represented by formula 10 prepared in step 1) and the compound represented by formula 11 is carried out in the presence of a palladium catalyst to give the compound represented by formula 12.

Here, as the palladium catalyst, tetrakis(triphenylphosphine) (Pd(PPh$_3$)$_4$), bis(triphenylphosphine)palladium(II) dichloride (PdCl$_2$(PPh$_3$)$_2$), palladium dichloride (PdCl$_2$), or palladium acetate (Pd(OCOCH$_3$)$_2$), may be used, and preferably, tetrakis(triphenylphosphine) (Pd(PPh$_3$)$_4$) may be used.

In addition, as the organic solvent, tetrahydrofuran (THF), diethylether, diphenylether, diisopropylether (DIPE), dimethylformamide (DMF), dimethylacetamide (DMA), dimethylsulfoxide DMSO), dichloromethane (DCM), chlorobenzene, toluene, or benzene may be used, and preferably, toluene may be used.

Furthermore, the reaction temperature is preferably carried out between 0° C. to the boiling point of the solvent, and the reaction time is not particularly limited, but the reaction may preferably be carried out for 0.5-10 hours.

In the preparation method for the compound represented by formula 2 of the present invention, step 3) is to prepare the compound represented by formula 2 by carrying out a reduction reaction of the compound represented by formula 12, prepared in step 2), in the presence of a base. More specifically, the compound represented by formula 12 prepared in step 2) is dissolved in an organic solvent, and the base is added, thereby giving the compound represented by formula 2 wherein an aldehyde group contained in the compound represented by formula 12 is reduced into a carboxyl group.

Here, as the organic solvent, methanol, ethanol, ethylacetate, tetrahydrofuran, diethyl ether, or a mixed solution of two or more thereof may be used, and preferably, a tetrahydrofuran: methanol (4:1) mixed solution may be used.

In addition, as the base, sodium borohydride ($NaBH_3$) or lithium aluminum hydride ($LiAlH_4$) may be used, and preferably, sodium borohydride ($NaBH_3$) may be used.

Furthermore, the reaction temperature is preferably carried out between 0° C. to the boiling point of the solvent, and the reaction time is not particularly limited, but the reaction may preferably be carried out for 0.5-10 hours.

Preparation Method 2

The compound represented by formula 1 of the present invention may be prepared, as shown in Reaction Scheme 3 below, by including steps of: carrying out a coupling reaction of a compound represented by formula 5 and a compound represented by formula 3 to prepare a compound represented by formula 6 (step 1);

carrying out a Mesylate reaction of the compound represented by formula 6 prepared in step 1) to prepare a compound represented by formula 7 (step 2);

replacing the Mesylate site of the compound represented by formula 7 prepared in step 2) with a compound represented by formula 13 to prepare a compound represented by formula 4 (step 3); and carrying out a reduction reaction of the compound represented by formula 4 prepared in step 3) to prepare the compound represented by formula 1 (step 4).

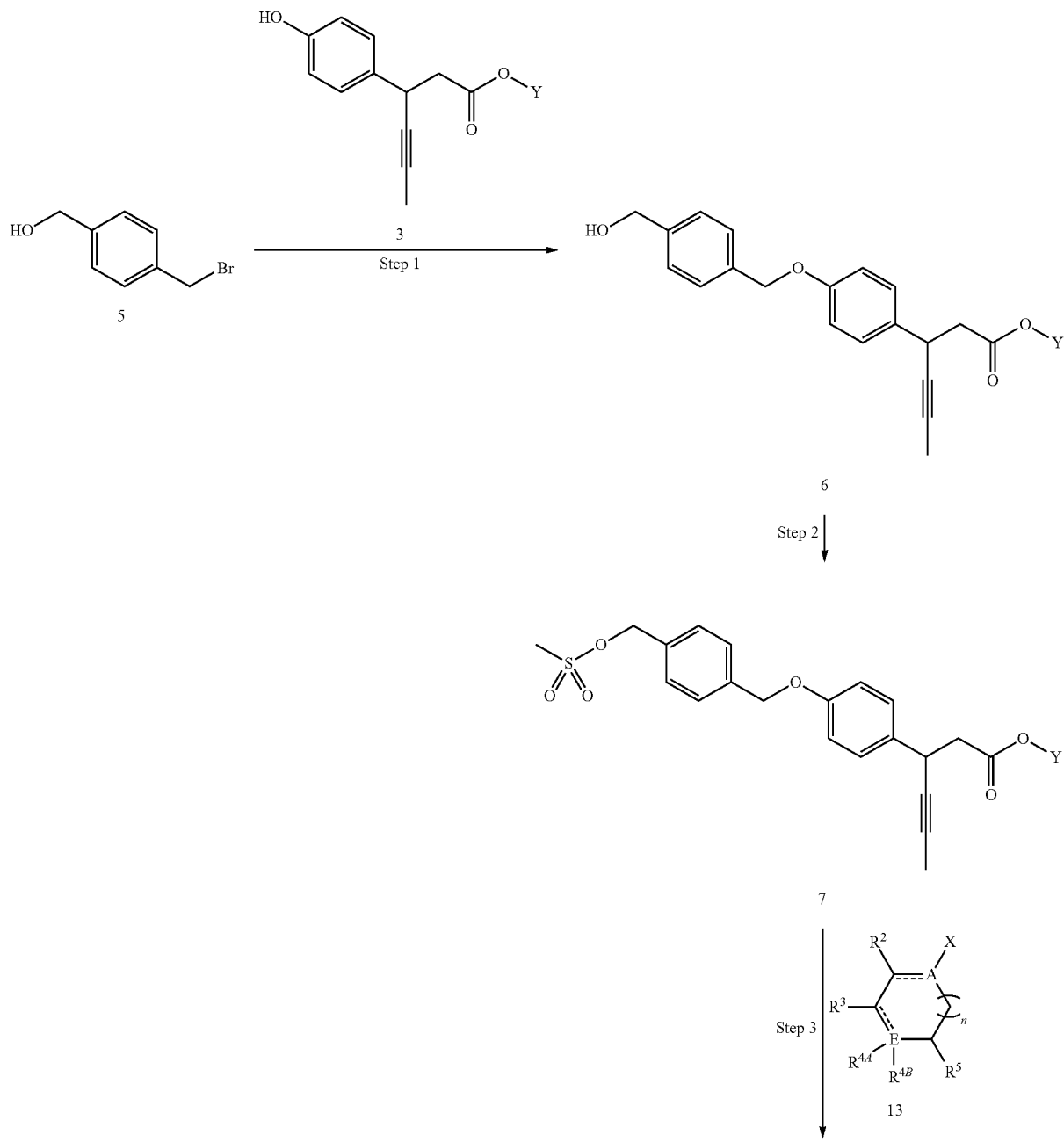

[Reaction Scheme 3]

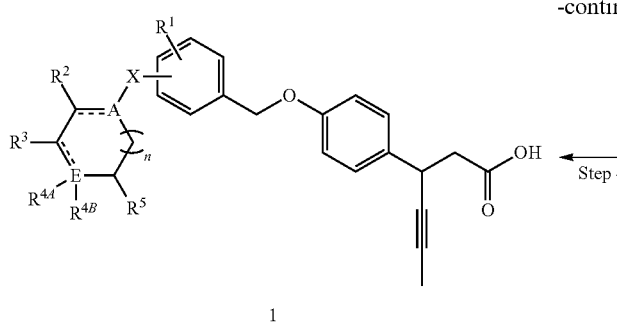

1

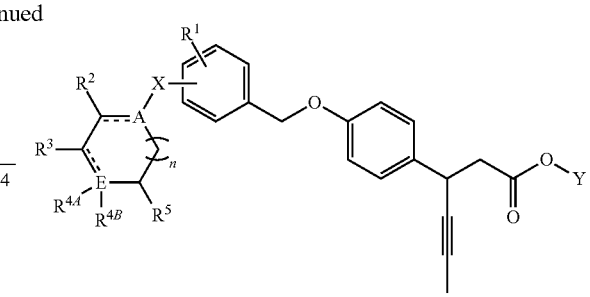

4

(wherein Reaction Scheme 3, $R^1$, $R^2$, $R^3$, $R^{4A}$, $R^{4B}$, R, A, E, n, and X are as defined in formula 1; and Y is $C_{1-10}$ straight or branched chain alkyl).

Hereinafter, the preparation method for the compound represented by formula 1 of the present invention will be described by steps in detail.

In the preparation method for the compound represented by formula 1 of the present invention, step 1) is to prepare the compound represented by formula 6 by carrying out a coupling reaction of the compound represented by formula 5 and the compound represented by formula 3.

Here, as the organic solvent, tetrahydrofuran (THF), diethylether, diphenylether, diisopropylether (DIPE), dimethylformamide (DMF), dimethylacetamide (DMA), dimethylsulfoxide DMSO), dichloromethane (DCM), chlorobenzene, toluene, or benzene may be used, and preferably, dimethylformamide (DMF) may be used.

In addition, as the base, cesium carbonate ($Cs_2CO_3$), sodium borohydride ($NaBH_3$), or lithium aluminum hydride ($LiAlH_4$) may be used, and preferably, cesium carbonate ($Cs_2CO_3$) may be used.

Furthermore, the reaction temperature is preferably carried out between 0° C. to the boiling point of the solvent, and the reaction time is not particularly limited, but the reaction may preferably be carried out for 0.5-10 hours.

In the preparation method for the compound represented by formula 1 of the present invention, step 2) is to prepare the compound represented by formula 7 by carrying out a Mesylate reaction of the compound represented by formula 6 prepared in step 1) in a solvent.

Here, as the reagent used in the Mesylate reaction, methanesulfonyl chloride (MsCl) may be used.

In addition, as the organic solvent, triethylamine (TEA), tetrahydrofuran (THF), diethylether, diphenylether, diisopropylether (DIPE), dimethylformamide (DMF), dimethylacetamide (DMA), dimethylsulfoxide (DMSO), dichloromethane (DCM), chlorobenzene, toluene, or benzene may be used, and preferably, triethylamine (TEA) may be used.

Furthermore, the reaction temperature is preferably carried out between 0° C. to the boiling point of the solvent, and the reaction time is not particularly limited, but the reaction may preferably be carried out for 0.5-10 hours.

In the preparation method for the compound represented by formula 1 of the present invention, step 3) is to prepare the compound represented by formula 4 by replacing the Mesylate site of the compound represented by formula 7 prepared in step 2) with the compound represented by formula 13.

Here, as the organic solvent, tetrahydrofuran (THF), diethylether, diphenylether, diisopropylether (DIPE), dimethylformamide (DMF), dimethylacetamide (DMA), dimethylsulfoxide DMSO), dichloromethane (DCM), chlorobenzene, toluene, or benzene may be used, and preferably, dichloromethane (DCM) may be used.

In addition, as the base, cesium carbonate ($Cs_2CO_3$), sodium borohydride ($NaBH_3$), or lithium aluminum hydride ($LiAlH_4$) may be used, and preferably, cesium carbonate ($Cs_2CO_3$) may be used.

Furthermore, the reaction temperature is preferably carried out between 0° C. to the boiling point of the solvent, and the reaction time is not particularly limited, but the reaction may preferably be carried out for 0.5-10 hours.

In the preparation method for the compound represented by formula 1 of the present invention, step 4) is to prepare the compound represented by formula 1 by carrying out a reduction reaction of the compound represented by formula 4, prepared in step 3), in the presence of a base. More specifically, the compound represented by formula 4 prepared in step 3) is reacted with the base at room temperature to give the compound represented by formula 1 wherein the ester group contained in the compound represented by formula 4 is reduced into the carboxyl group.

Here, as the base, potassium hydroxide (KOH), sodium hydroxide (NaOH), and lithium hydroxide (LiOH) may be used, and preferably, potassium hydroxide (KOH) may be used.

In addition, as the reaction solvent, tetrahydrofuran (THF), dichloromethane (DCM), toluene, and acetonitrile may be used, and preferably tetrahydrofuran (THF) may be used.

Furthermore, the reaction temperature is preferably carried out between 0° C. to the boiling point of the solvent, and the reaction time is not particularly limited, but the reaction may preferably be carried out for 0.5-10 hours.

Preparation Method 3

The compound represented by formula 1 of the present invention may be prepared, as shown in Reaction Scheme 4 below, by including a step for carrying out a ring-opening reaction of a compound represented by formula 1a to prepare a compound represented by formula 1b (step 1).

[Reaction Scheme 4]

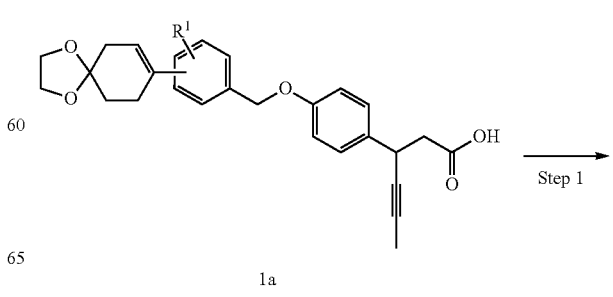

1a

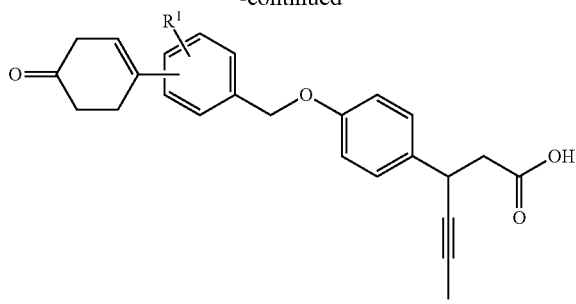

1b

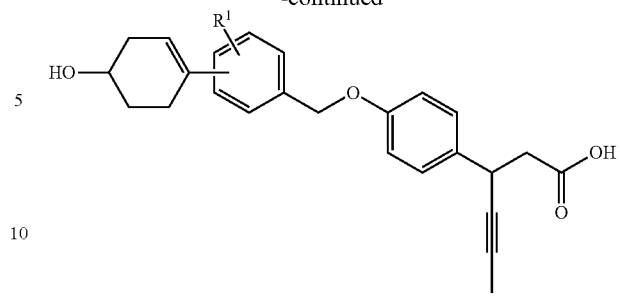

1c (wherein Reaction Scheme 4, $R^1$ is as defined in formula 1; and the compounds represented by formulas 1a and 1b are included in the compound represented by formula 1).

Hereinafter, the preparation method for the compound represented by formula 1 of the present invention will be described by steps in detail.

In the preparation method for the compound represented by formula 1 of the present invention, step 1) is to prepare the compound represented by formula 1b by carrying out a ring-opening reaction of the compound represented by formula 1a in the presence of an acid. More specifically, the compound represented by formula 1a included in the compound represented by formula 1 is subjected to a ring-opening reaction in the presence of an acid, thereby giving the compound represented by formula 1b, which contains carbonyl through the ring opening of the hetero ring of the compound represented by formula 1a.

Here, as the acid, an inorganic acid, such as hydrochloric acid, sulfuric acid, or phosphoric acid, may be used, and preferably, hydrochloric acid may be used.

In addition, as the reaction solvent, tetrahydrofuran (THF), dichloromethane (DCM), toluene, and acetonitrile may be used, and preferably tetrahydrofuran (THF) may be used.

Furthermore, the reaction temperature is preferably carried out between 0° C. to the boiling point of the solvent, and the reaction time is not particularly limited, but the reaction may preferably be carried out for 0.5-10 hours.

Preparation Method 4

The compound represented by formula 1 of the present invention may be prepared, as shown in Reaction Scheme 5 below, by including a step for carrying out a reduction reaction of a compound represented by formula 1b to prepare a compound represented by formula 1c (step 1).

[Reaction Scheme 5]

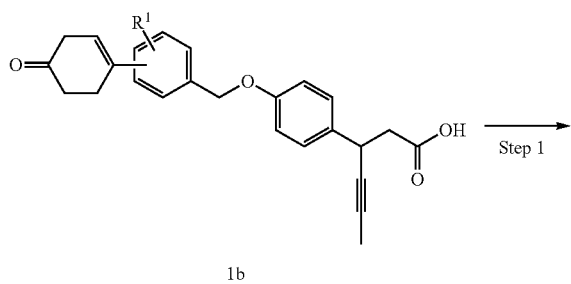

1b (wherein Reaction Scheme 5, $R^1$ is as defined in formula 1; and the compounds represented by formulas 1b and 1c are included in the compound represented by formula 1).

Hereinafter, the preparation method for the compound represented by formula 1 of the present invention will be described by steps in detail.

In the preparation method for the compound represented by formula 1 of the present invention, step 1) is to prepare the compound represented by formula 1c by carrying out a reduction reaction of the compound represented by formula 1b in the presence of a base. More specifically, the compound represented by formula 1b, which is one of the compounds represented by formula 1, is subjected to a reduction reaction in the presence of a base, thereby giving the compound represented by formula 1c in which the carbonyl group of the compound represented by formula 1b is reduced to the hydroxyl group.

In addition, as the base, sodium borohydride ($NaBH_3$) or lithium aluminum hydride ($LiAlH_4$) may be used, and preferably, sodium borohydride ($NaBH_3$) may be used.

In addition, as the reaction solvent, tetrahydrofuran (THF), dichloromethane (DCM), toluene, and acetonitrile may be used, and preferably tetrahydrofuran (THF) may be used.

Furthermore, the reaction temperature is preferably carried out between 0° C. to the boiling point of the solvent, and the reaction time is not particularly limited, but the reaction may preferably be carried out for 0.5-10 hours.

The pharmaceutical composition of the present invention is characterized by activating the GPR40 enzyme.

GPR40 is the G-protein coupled receptor (GPCR) that is mainly expressed in insulin secreting cells of the pancreas. The GPR40 expression profile has the potential usability for the treatment of various metabolic diseases including obesity and diabetes.

In this regard, as a result of evaluating the GPR40 receptor activity of a compound represented by formula 1 of the present invention, an optical isomer thereof, or a pharmaceutically acceptable salt thereof, it was verified that the compounds of all the examples of the present invention activated the GPR40 receptor by 50% ($EC_{50}$) at low concentrations, and thus, the activating effects of the compounds were excellent (see Experimental Examples 1 and 2, and FIG. 1).

In addition, as a result of evaluating the CYP enzyme inhibitory activity by the drug metabolisms of a compound represented by formula 1 of the present invention, an optical isomer thereof, or a pharmaceutically acceptable salt thereof, it was verified that the compounds of all the examples of the present invention had low CYP enzyme inhibitory activity, causing no toxicity due to the concentration at the time of co-administration with other drugs, and thus, the compounds of the present invention could be co-administered with other drugs in the complication incidence (see Experimental Example 3).

Furthermore, as a result of conducting the oral glucose tolerance experiment for a compound represented by formula 1 of the present invention, an optical isomer thereof, or the pharmaceutically acceptable salt thereof, it could be seen that the compounds of all the examples of the present invention showed a similar or superior blood sugar lowering effect compared with a GPR40 activator that has been known in the conventional art, and thus, the compounds of the present invention had a significantly excellent effect in activating GPR40 in vivo (see Experimental Examples 4, 5, and 6).

In addition, as a result of conducting an experiment for evaluating a blood GLP-1 concentration increase rate after the oral administration of a compound represented by formula 1 of the present invention, an optical isomer thereof, or a pharmaceutically acceptable salt thereof, it was verified that, compared with a glucose treated group (Veh.), the compound of Comparative Example 1 showed no blood GLP-1 concentration increase effect after administration, but the compound of Example 9 of the present invention increased the blood GLP-1 concentration when administered to SD rats (see Experimental Example 7, and FIG. 2).

Furthermore, it was verified that the co-administration with a novel 3-(4-(benzyloxy)phenyl)hex-4-ynoic acid derivative of the present invention and a representative drug, such as dipeptidyl peptidase IV (DPPIV) inhibitor-based, sulfonylurea-based, thiazolidinedione (TZD)-based, or biguanide-based drug, showed an excellent blood glucose-lowering effect compared with the administration of the drugs alone (see Tables 8, 9, 10, and 11 of Experimental Examples 8, 9, 10, and 11, and FIGS. 3, 4, 5, and 6).

Therefore, the compounds represented by formula 1 of the present invention have an excellent effect of activating GPR40 protein, leading to an excellent insulin secretion promoting effect, and can be co-administered together with other drugs, and also, have a significantly excellent effect in activating GPR40 protein in vivo, and thus, the composition containing the compound represented by formula 1 as an active ingredient can be advantageously used as a pharmaceutical composition for the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

The compound represented by formula 1 of the present invention can be administered in several dosage forms for oral or parenteral administration at the time of clinical administration, and may be formulated by using a diluent or excipient, such as a filler, an extender, a binder, a wetting agent, a disintegrant, or a surfactant, that is ordinarily used.

Solid preparations for oral administration include a tablet, a pill, a powder, granules, a capsule, a troche, and the like. These solid preparations may be prepared by mixing a least one of the compounds of the present invention and at least one excipient, for example, starch, calcium carbonate, sucrose or lactose, gelatin, or the like. In addition to simple excipients, lubricants such as magnesium stearate and talc may also be used. Examples of a liquid preparation for oral administration may include a suspension, an oral liquid, an emulsion, a syrup, and the like. In addition to commonly used simple diluents, such as water and liquid paraffin, various excipients, such as a wetting agent, a sweetener, an aroma, a preservative, and the like may be included in the liquid preparation.

Preparations for parenteral administration include a sterilized aqueous solution, a non-aqueous solvent, a suspension solvent, an emulsion, a freeze-drying agent, and a suppository. As the non-aqueous solvent and the suspension solvent, propylene glycol, polyethylene glycol, a vegetable oil such as an olive oil, an injectable ester such as ethylolate, and the like may be used. As a substrate for the suppository, Witepsol, Macrogol, twin 61, cacao butter, laurin butter, glycerol, gelatin, or the like may be used.

In addition, the effective dose of the compound of the present invention on the human body may vary depending on the age, body weight, sex, form of administration, health condition, and disease severity of a patient, and is generally about 0.001-100 mg/kg/day, and preferably 0.01-35 mg/kg/day. Based on an adult patient weighing 70 kg, the dose is generally 0.07-7000 mg/day, and preferably 0.7-2500 mg/day, and the dose may be administered once or several times a day at a predetermined time interval according to the judgment of a doctor or a pharmacist.

Hereinafter, the present invention will be described in detail with reference to examples and experimental examples.

However, the following examples and experimental examples are merely for illustrating the present invention, and are not intended to limit the scope of the present invention.

<Preparative Example 1> Preparation of ethyl 3-(4-hydroxyphenyl)hex-4-ynoate

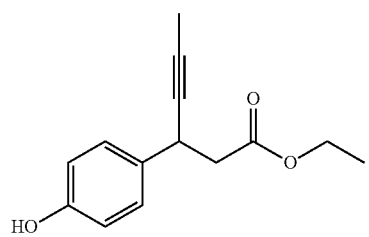 [SMILES: CC#CC(CC(=O)OCC)c1ccc(O)cc1]

Under a nitrogen atmosphere, 3-(4-hydroxyphenyl)-hex-4-ynoic acid (20.0 g) and ethanol (200 mL) were loaded in a 250-mL flask and stirred to dissolve, and then, sulfuric acid (9.6 mL) was slowly added dropwise at room temperature. Thereafter, the reaction mixture was stirred under reflux for 6 hours or longer. Upon completion of the reaction, distilled water (150 mL) was slowly added dropwise, followed by extraction using ethylacetate (200 mL). The extracted organic layer was dried under reduced pressure to give the title compound (19.5 g, 85.7%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

<Preparative Example 2> Preparation of (S)-ethyl 3-(4-hydroxyphenyl)hex-4-ynoate

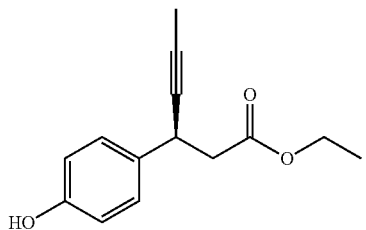 [SMILES: CC#C[C@@H](CC(=O)OCC)c1ccc(O)cc1]

Under a nitrogen atmosphere, (S)-3-(4-hydroxyphenyl)-hex-4-ynoic acid (20.0 g) and ethanol (200 mL) were loaded in a 250-mL flask and stirred to dissolve, and then, sulfuric acid (9.6 mL) was slowly added dropwise at room temperature. Thereafter, the reaction mixture was stirred under reflux for 6 hours or longer. Upon completion of the reaction, distilled water (150 mL) was slowly added dropwise, followed by extraction using ethylacetate (200 mL). The extracted organic layer was dried under reduced pressure to give the title compound (21.2 g, 93.2%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

<Preparative Example 3> Preparation of (S)-ethyl 3-(4-hydroxyphenyl)hex-4-ynoate

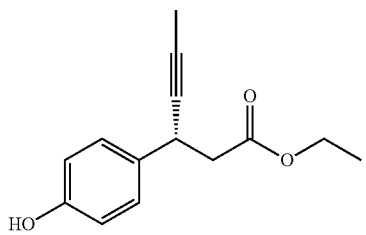 [SMILES: CC#C[C@H](CC(=O)OCC)c1ccc(O)cc1]

Under a nitrogen atmosphere, (R)-3-(4-hydroxyphenyl)-hex-4-ynoic acid (20.0 g) and ethanol (200 mL) were loaded in a 250-mL flask and stirred to dissolve, and then, sulfuric acid (9.6 mL) was slowly added dropwise at room temperature. Thereafter, the reaction mixture was stirred under reflux for 6 hours or longer. Upon completion of the reaction, distilled water (150 mL) was slowly added dropwise, followed by extraction using ethylacetate (200 mL). The extracted organic layer was dried under reduced pressure to give the title compound (20.6 g, 90.6%).

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

<Preparative Example 4> Preparation of (3-(1,4-dioxaspiro[4.5]dec-7-en-8-yl)phenyl)methanol

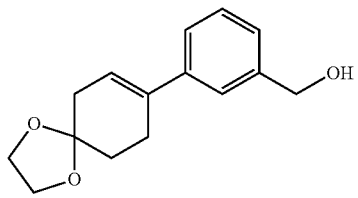 [SMILES: OCc1cccc(C2=CCC3(CC2)OCCO3)c1]

Step 1: Preparation of 1,4-dioxaspiro[4.5]dec-7-en-8-yl trifluoromethanesulfonate Under a nitrogen atmosphere, 1.4-dioxaspiro[4.5]decan-8-one (30.0 g) and toluene (300 mL) were loaded in a 1000-mL flask and stirred to dissolve, and then, N-phenyl bis(trifluoromethanesulfonimide) (64.3 g) was added. Thereafter, a 0.7 M potassium bis(trimethylsilyl)amide solution (257 mL) was slowly added dropwise thereto by using a dropping funnel at −78° C., and then the mixture was stirred for 4 hours or longer while the temperature was slowly raised to room temperature. Upon completion of the reaction, distilled water (200 mL) was slowly added dropwise, followed by extraction using ethylacetate (300 mL), and then the extracted organic layer was dried under reduced pressure to give the title compound (54.7 g, 98.8%).

$^1$H NMR (400 MHz, CDCl$_3$): δ 5.68 (1H, t), 4.01 (4H, s), 2.55 (2H, t), 2.42 (2H, d), 1.92 (2H, t).

Step 2: Preparation of 3-(1,4-dioxaspiro[4.5]dec-7-en-8-yl)benzaldehyde

Under a nitrogen atmosphere, 1.4-dioxaspiro[4.5]dec-7-en-8-yl trifluoromethanesulfonate (54.70 g) and toluene (300 mL) were loaded in a 1000-mL flask and stirred to dissolve, and then, 3-formylphenyl boronic acid (28.7 g) and cesium carbonate (156 g) were added. The mixture was cooled to 0° C., and tetrakis(triphenylphosphine)palladium (11.09 g) was slowly added, and then the mixture was stirred for 3 hours or longer while the temperature was again raised to room temperature. Upon completion of the reaction, distilled water (200 mL) was slowly added dropwise, followed by extraction using ethylacetate (300 mL), and then the extracted organic layer was dried under reduced pressure to give the title compound (45.9 g, 99%).

$^1$H NMR (400 MHz, CDCl$_3$): δ 10.03 (1H, s), 7.92 (1H, s), 7.76 (1H, d), 7.67 (1H, d), 7.47 (1H, t), 6.11 (1H, s), 4.05 (4H, s), 2.71 (2H, t), 2.51 (2H, s), 1.97 (2H, t).

Step 3: Preparation of (3-(1,4-dioxaspiro[4.5]dec-7-en-8-yl)phenyl)methanol

Under a nitrogen atmosphere, 3-(1.4-dioxaspiro[4.5]dec-7-en-8-yl)benzaldehyde (46.9 g), tetrahydrofuran (160 mL), and methanol (40 mL) were added to a 500-mL flask and stirred to dissolve, and then the mixture was cooled to 0° C. Thereafter, sodium borohydride (10.9 g) was added slowly, and the mixture was stirred for 3 hours or longer while the temperature was raised to room temperature. Upon completion of the reaction, distilled water (150 mL) was slowly added dropwise, followed by extraction using ethylacetate (150 mL), and then the extracted organic layer was dried under reduced pressure to give the title compound (37.8 g, 81.7%).

$^1$H NMR (400 MHz, CDCl$_3$): δ 7.34 (1H, s), 7.25 (3H, m), 6.01 (1H, m), 4.69 (2H, d), 4.04 (4H, s), 2.68 (2H, m), 2.48 (2H, s), 1.94 (2H, t), 1.80 (1H, t).

<Preparative Example 5> Preparation of (4-(1,4-dioxaspiro[4.5]dec-7-en-8-yl)phenyl)methanol

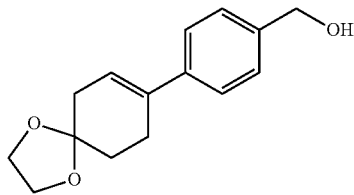 [SMILES: OCc1ccc(C2=CCC3(CC2)OCCO3)cc1]

Step 1: Preparation of 4-(1,4-dioxaspiro[4.5]dec-7-en-8-yl)benzaldehyde

Under a nitrogen atmosphere, 1,4-dioxaspiro[4.5]dec-7-en-8-yl trifluoromethanesulfonate (3.0 g) and toluene (50 mL) were loaded in a 250-mL flask and stirred to dissolve, and then, 3-formylphenyl boronic acid (1.8 g) and cesium carbonate (8.47 g) were added, followed by cooling to 0° C. Thereafter, tetrakis(triphenyl phosphine)palladium (601 mg) was slowly added, and then the mixture was stirred for 3 hours or longer while the temperature was raised. Upon completion of the reaction, distilled water (500 mL) was slowly added dropwise, followed by extraction using ethylacetate (100 mL), and then the extracted organic layer was dried under reduced pressure to give the title compound (2.0 g, 78.7%).

$^1$H NMR (400 MHz, CDCl$_3$): δ 10.00 (1H, s), 7.84 (2H, d), 7.57 (2H, d), 6.19 (1H, s), 4.06 (4H, s), 2.71 (2H, t), 2.53 (2H, s), 1.97 (2H, t).

Step 2: Preparation of (4-(1,4-dioxaspiro[4.5]dec-7-en-8-yl)phenyl)methanol

Under a nitrogen atmosphere, 4-(1,4-dioxaspiro[4.5]dec-7-en-8-yl)benzaldehyde (2.0 g), tetrahydrofuran (40 mL), and methanol (10 mL) were added to a 250-mL flask and stirred to dissolve, and then the mixture was cooled to 0° C. Thereafter, sodium borohydride (619 mg) was added slowly, and the mixture was stirred for 3 hours or longer while the temperature was raised to room temperature. Upon completion of the reaction, distilled water (50 mL) was slowly added dropwise, followed by extraction using ethylacetate (100 mL), and then the extracted organic layer was dried under reduced pressure to give the title compound (1.6 g, 52.9%).

$^1$H NMR (400 MHz, CDCl$_3$): δ 7.40 (2H, d), 7.32 (2H, d), 6.01 (1H, m), 4.70 (2H, d), 4.13 (4H, s), 2.68 (2H, t), 2.49 (2H, s), 1.93 (2H, t), 1.60 (1H, t).

<Preparative Example 6> Ethyl 3-(4-(4-((methylsulfonyloxy)methyl)benzyloxy) phenyl)hex-4-ynoate Step 1: Preparation of (4-(bromomethyl)phenyl)methanol

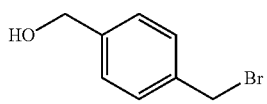

Under a nitrogen atmosphere, 4-(bromomethyl)benzoate (5.0 g) and MC (20 mL) were added to a 1-L flask and stirred to dissolve, and then DIBAL-H (70 ml) was slowly added dropwise. After stirring for 5 hours, upon completion of the reaction, the temperature was lowered to 0° C., and distilled water was slowly added dropwise, followed by extraction using MC. The extracted organic layer was dried under reduced pressure to give the title compound.

$^1$H NMR (400 MHz, CDCl$_3$): δ 7.42 (2H, d), 7.38 (2H, d), 4.73 (2H, s), 4.52 (2H, m).

Step 2: Preparation of ethyl 3-(4-(4-(hydroxymethyl)benzyloxy)phenyl)hex-4-ynoate

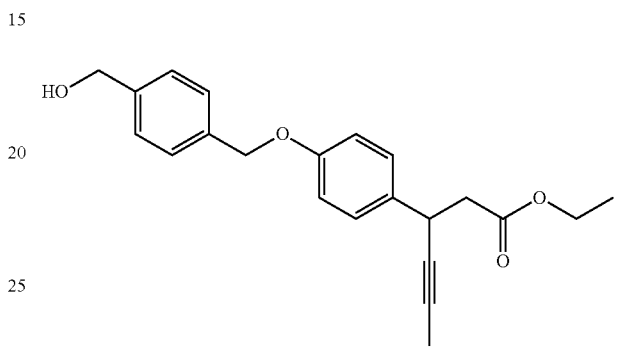

Under a nitrogen atmosphere, ethyl 3-(4-hydroxyphenyl) hex-4-ynoate (4.0 g) obtained in Preparative Example 1 and (4-(bromomethyl)phenyl)methanol (5.0 g) obtained in step 1 were added to DMF (50 mL) in a 500-mL flask and stirred to dissolve, followed by adding dropwise Cs2CO3 (9.0 g), and then the mixture was stirred at room temperature for 12 hours. Upon completion of the reaction, distilled water was slowly added dropwise, extracted with ethyl acetate, washed with brine, dried over anhydrous magnesium sulfate, and then concentrated. Thereafter, the reaction product was separated by silica column chromatography to give the title compound.

$^1$H NMR (400 MHz, CDCl$_3$): δ 7.42 (2H, d), 7.38 (2H, d), 7.29 (2H, d), 6.93 (2H, d), 5.06 (2H, s), 4.73 (2H, d), 4.15 (2H, m), 4.06 (1H, m), 2.68 (2H, m), 1.84 (3H, s), 1.69 (1H, m), 1.24 (3H, m).

Step 3: Preparation of ethyl 3-(4-(4-(methylsulfonlyoxy)methyl)benzyloxy)phenyl) hex-4-ynoate

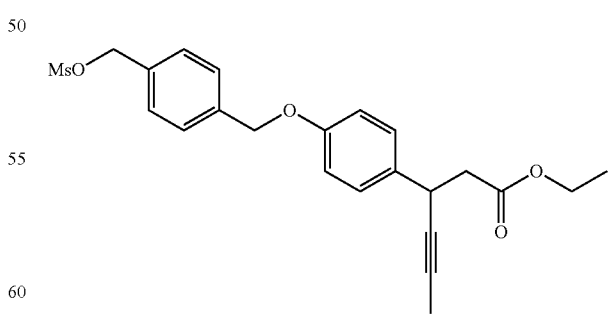

Under a nitrogen atmosphere, 3-(4-(4-(hydroxymethyl) benzyloxy)phenyl) hex-4-ynoate (3.0 g) obtained in step 2 was added to MC (30 mL) in a 500-mL flask and stirred to dissolve, and then TEA (4.0 mL) was added dropwise at 0° C. After 30 minutes, MsCl (2.1 mL) was slowly added dropwise. Upon completion of the reaction after one hour, distilled water was slowly added dropwise, followed by extraction using MC. The extracted organic layer was dried under reduced pressure to give the title compound.

¹H NMR (400 MHz, CDCl₃): δ 7.49 (4H, m), 7.29 (2H, d), 6.93 (2H, d), 5.27 (2H, s), 5.08 (2H, s), 4.15 (2H, m), 4.06 (1H, m), 2.95 (3H, s), 2.68 (2H, m), 1.84 (3H, s), 1.69 (1H, m), 1.24 (3H, m).

<Preparative Example 7> Preparation of (S)-ethyl 3-(4-(4-((methylsulfonyloxy) methyl)benzyloxy) phenyl)hex-4-ynoate Step 1: Preparation of (S)-ethyl 3-(4-(4-(hydroxymethyl)benzyloxy)phenyl)hex-4-ynoate

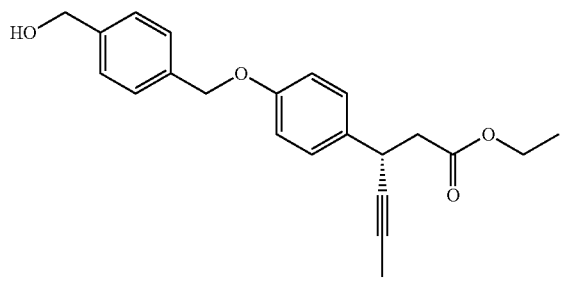 [SMILES: CC#C[C@@H](CC(=O)OCC)c1ccc(OCc2ccc(CO)cc2)cc1]

The title compound was obtained by the same method as in step 2 in Preparative Example 6 except that (S)-ethyl 3-(4-hydroxyphenyl)hex-4-ynoate is used instead of ethyl 3-(4-hydroxyphenyl)hex-4-ynoate.

¹H NMR (400 MHz, CDCl₃): δ 7.42 (2H, d), 7.38 (2H, d), 7.29 (2H, d), 6.93 (2H, d), 5.06 (2H, s), 4.73 (2H, d), 4.15 (2H, m), 4.06 (1H, m), 2.68 (2H, m), 1.84 (3H, s), 1.69 (1H, m), 1.24 (3H, m).

Step 2: Preparation of (S)-ethyl 3-(4-(4-((methylsulfonlyoxy)methyl)benzyloxy) phenyl)hex-4-ynoate

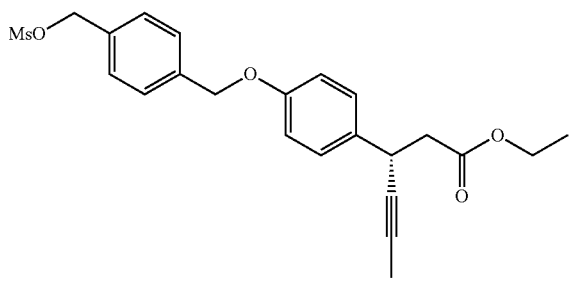 [SMILES: CC#C[C@@H](CC(=O)OCC)c1ccc(OCc2ccc(COS(C)(=O)=O)cc2)cc1]

The title compound was obtained by the same method as in step 3 in Preparative Example 6 except that (S)-ethyl 3-(4-(4-(hydroxymethyl)benzyl)phenyl)hex-4-ynoate obtained in step 1 was used instead of ethyl 3-(4-(4-(hydroxymethyl)benzyloxy)phenyl)hex-4-ynoate.

¹H NMR (400 MHz, CDCl₃): δ 7.49 (4H, m), 7.29 (2H, d), 6.93 (2H, d), 5.27 (2H, s), 5.08 (2H, s), 4.15 (2H, m), 4.06 (1H, m), 2.95 (3H, s), 2.68 (2H, m), 1.84 (3H, s), 1.69 (1H, m), 1.24 (3H, m).

<Preparative Example 8> Preparation of 6-methoxy-1,2,3,4-tetrahydroisoquinoline

Step 1: Preparation of ethyl 3-methoxyphenethyl carbamate

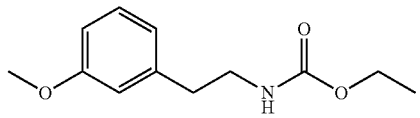 [SMILES: CCOC(=O)NCCc1cccc(OC)c1]

Under a nitrogen atmosphere, 2-(3-methoxyphenyl)ethylamine (25 g) was added to MC (300 mL) and stirred to dissolve, and then TEA (24.2 mL) was added to dropwise at 0° C. After 30 minutes, ethyl chloroformate (16.6 mL) was slowly added dropwise. Upon completion of the reaction after one hour, distilled water was slowly added dropwise, followed by extraction using MC. The extracted organic layer was dried under reduced pressure to give the title compound.

¹H NMR (400 MHz, CDCl₃): δ 7.25 (1H, m), 6.79 (3H, m), 4.70 (1H, s), 4.13 (2H, m), 3.81 (3H, s), 3.46 (2H, m), 2.80 (2H, m), 1.25 (3H, m).

Step 2: Preparation of 6-methoxy-3,4-dihydroisoquinoline-1(2H)-one

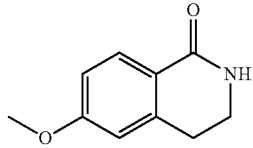

Under a nitrogen atmosphere, 36 g of ethyl 3-methoxyphenethylcarbamate obtained in step 1 was stirred to dissolve in 120 g of polyphosphoric acid in a 500-mL flask, and the mixture was heated under reflux for 3 hours or longer. After the temperature was lowered to room temperature, ethyl acetate and distilled water were slowly added dropwise, followed by extraction three times or more. The extracted organic layer was washed with brine, and dried over anhydrous magnesium sulfate, and then concentrated. Thereafter, the reaction product was separated by silica column chromatography to give the title compound.

¹H NMR (400 MHz, CDCl₃): δ 8.03 (1H, d), 6.87 (1H, d), 6.72 (1H, s), 6.44 (1H, s), 3.86 (3H, s), 3.57 (2H, m), 2.98 (2H, m).

Step 3: Preparation of 6-methoxy-1,2,3,4-tetrahydroisoquinoline

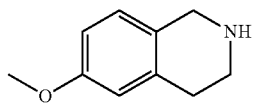

Under a nitrogen atmosphere, 10 g of 6-methoxy-3,4-dihydroisoquinoline-1(2H)-one obtained in step 2 was stirred to dissolve in 150 mL of THF, and 4.3 g of LAH was slowly added dropwise at 0° C. After heating under reflux for 5 hours or longer, upon completion of the reaction, distilled water was slowly added dropwise, extracted with ethyl acetate, washed with brine, dried over anhydrous magnesium sulfate, and then concentrated. Thereafter, the title compound was obtained by solidification.

$^1$H NMR (400 MHz, CDCl$_3$): δ 6.94 (1H, d), 6.73 (1H, d), 6.65 (1H, s), 4.14 (2H, s), 3.80 (3H, s), 3.13 (2H, m), 2.79 (2H, m).

<Preparative Example 9> Preparation of 4-(4-(methylsulfonyl)phenyl)-1,2,3,6-tetrahydropyridine hydrochloride Step 1: Preparation of tert-butyl 4-(4-(methylsulfonyl)phenyl)-5,6-dihydropyridine-1(2H)-carboxylate

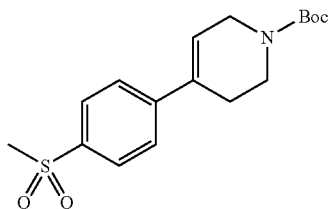 [SMILES: CC(C)(C)OC(=O)N1CC=C(c2ccc(S(C)(=O)=O)cc2)CC1]

Under a nitrogen atmosphere, 3.31 g of tert-butyl 4-(trifluoromethylsulfonyloxy)-5,6-dihydropyridine-1(2H)-carboxylate and 50 mL of toluene were loaded in a 1000-mL flask and stirred to dissolve, and then 2.0 g of 4-(methylsulfonyl)phenylboronic acid and 6.6 g of cesium carbonate were added. Thereafter, the mixture was cooled to 0° C., followed by slowly adding 1.16 g of tetrakis(triphenylphosphine)palladium, and then stirred for 3 hours or longer while the temperature was again raised to room temperature. Upon completion of the reaction, distilled water was slowly added dropwise, and then extracted with ethyl acetate. The extracted organic layer was dried under reduced pressure, and then separated by silica column chromatography to give the title compound.

$^1$H NMR (400 MHz, CDCl$_3$): δ 7.92 (2H. d), 7.56 (2H, d), 6.21 (1H, s), 4.14 (2H, d), 3.68 (2H, m), 3.07 (3H, s), 2.56 (2H, s), 1.49 (9H, s).

Step 2: Preparation of 4-(4-(methylsulfonyl)phenyl)-1,2,3,6-tetrahydropyridine hydrochloride

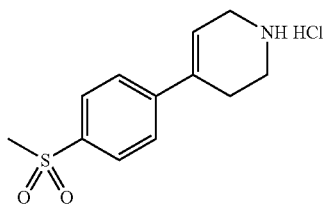

After 1.4 g of tert-butyl 4-(4-(methylsulfonyl)phenyl)-5,6-dihydropyridine-1(2H)-carboxylate (1.4 g) obtained in step 1 was dissolved in 20 ml of MC, 10.4 mL of 4 N HCl was added dropwise. Upon completion of the reaction after five hours, diethyl ether was added dropwise and solidified to give the title compound.

$^1$H NMR (400 MHz, D$_2$O): δ 7.92 (2H. d), 7.56 (2H, d), 6.21 (1H, s), 4.14 (2H, d), 3.68 (2H, m), 3.07 (3H, s), 2.56 (2H, s).

<Preparative Example 10> Preparation of 4-(1,2,3,6-tetrahydropyridin-4-yl)phenol hydrochloride Step 1: Preparation of tert-butyl 4-(4-hydroxyphenyl)-5,6-dihydropyridine-1(2H)-carboxylate

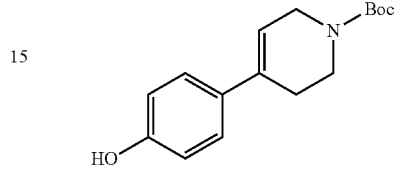

The title compound was obtained by the same method as in step 1 in Preparative Example 9 except that 4-hydroxyphenylboronic acid was used instead of 4-(methylsulfonyl)phenylboronic acid.

$^1$H NMR (400 MHz, CDCl$_3$): δ 7.26 (2H, d), 6.83 (2H, d), 5.93 (1H, s), 5.47 (1H, s), 4.07 (2H, s), 3.66 (2H, m), 2.50 (2H, s), 1.52 (9H, s).

Step 2: Preparation of 4-(1,2,3,6-tetrahydropyridin-4-yl)phenol hydrochloride

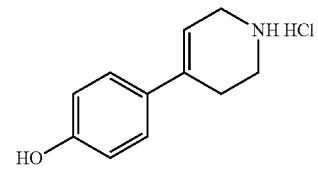

The title compound was obtained by the same method as in step 2 in Preparative Example 9 except that tert-butyl 4-(4-hydroxyphenyl)-5,6-dihydropyridine-1(2H)-carboxylate obtained in step 1 was used instead of tert-butyl 4-(4-(methylsulfonyl)phenyl)-5,6-dihydropyridine-1(2H)-carboxylate.

$^1$H NMR (400 MHz, D$_2$O): δ 7.26 (2H, d), 6.83 (2H, d), 5.93 (1H, s), 5.47 (1H, s), 4.07 (2H, s), 3.66 (2H, m), 2.50 (2H, s).

<Preparative Example 11> Preparation of 4-(4-(3-(methylsulfonyl)propoxy)phenyl)-1,2,3,6-tetrahydropyridine hydrochloride Step 1: Preparation of 3-(methylthio)propyl 4-methylbenzenesulfonate

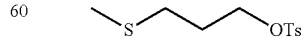

Under a nitrogen atmosphere, 25.4 g of 3-(methylthio)propan-1-ol was added in 500 mL of MC in a 500-mL flask and stirred to dissolve, and then 44 mL of TEA was added to dropwise at 0° C. After 30 minutes, 46 g of TsCl was slowly added dropwise, and upon completion of the reaction after one hour, distilled water was slowly added dropwise, followed by extraction using MC. The extracted organic layer was dried under reduced pressure to give the title compound.

$^1$H NMR (400 MHz, CDCl$_3$): δ 7.81 (2H, d), 7.38 (2H, d), 4.16 (2H, m), 2.53 (2H, m), 2.47 (3H, s), 2.05 (3H, s), 1.94 (2H, m).

Step 2: Preparation of 3-(methylsulfonyl)propyl 4-methylbenzenesulfonate

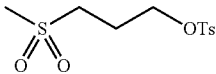 [SMILES: Cc1ccc(S(=O)(=O)OCCCS(C)(=O)=O)cc1]

Under a nitrogen atmosphere, 62 g of 3-(methylthio)propyl 4-methylbenzenesulfonate obtained in step 1 was added in THF/distilled water (150/100 mL) in a flask and stirred to dissolve, and then 310 g of oxone was added dropwise at 0° C. After stirring at room temperature for 12 hours or longer, upon completion of the reaction, distilled water was slowly added dropwise, extracted with ethyl acetate, washed with brine, and dried over anhydrous magnesium sulfate to give the title compound.

$^1$H NMR (400 MHz, CDCl$_3$): δ 7.81 (2H, d), 7.38 (2H, d), 4.20 (2H, m), 3.13 (2H, m), 2.93 (3H, s), 2.48 (3H, s), 2.23 (2H, m).

Step 3: Preparation of tert-butyl 4-(4-(3-methylsulfonyl)propoxy)phenyl)-5,6-dihydropyridine-1(2H)-carboxylate

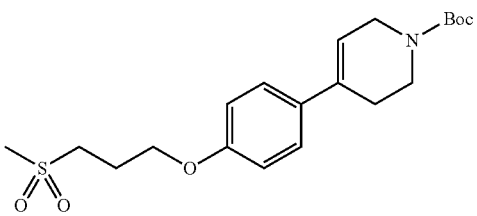 [SMILES: CC(C)(C)OC(=O)N1CC=C(c2ccc(OCCCS(C)(=O)=O)cc2)CC1]

The title compound was obtained by the same method as in step 2 in Preparative Example 6 except that tert-butyl 4-(4-hydroxyphenyl)-5,6-dihydropyridine-1(2H)-carboxylate obtained in step 1 and 3-(methylsulfonyl)propyl 4-methylbenzenesulfonate obtained in step 2 were used.

$^1$H NMR (400 MHz, CDCl$_3$): δ 7.34 (2H, d), 6.85 (2H, d), 6.00 (1H, s), 4.12 (2H, s), 3.28 (2H, m), 3.18 (2H, s), 2.97 (3H, s), 2.72 (2H, m), 2.56 (2H, m), 2.36 (2H, m), 1.52 (9H, s).

Step 4: Preparation of 4-(4-(3-(methylsulfonyl)propoxy)phenyl)-1,2,3,6-tetrahydropyridine hydrochloride

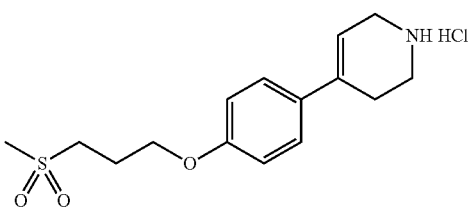

The title compound was obtained by the same method as in step 2 in Preparative Example 9 except that tert-butyl 4-(4-(3-methylsulfonyl)propoxy)phenyl)-5,6-dihydropyridine-1(2H)-carboxylate obtained in step 3 was used instead of tert-butyl 4-(4-(methylsulfonyl)phenyl)-5,6-dihydropyridine-1(2H)-carboxylate.

$^1$H NMR (400 MHz, D$_2$O): δ 7.34 (2H, d), 6.85 (2H, d), 6.00 (1H, s), 4.12 (2H, s), 3.28 (2H, m), 3.18 (2H, s), 2.97 (3H, s), 2.72 (2H, m), 2.56 (2H, m), 2.36 (2H, m).

<Preparative Example 12> Preparation of (3S)-ethyl 3-(4-(4-(1-bromoethyl) benzyloxy)phenyl)hex-4-ynoate Step 1: Preparation of 1-(4-(bromomethyl)phenyl)ethanone

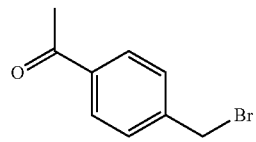

Under a nitrogen atmosphere, 5.0 g of 1-p-tolyl ethanone was added to 100 mL of CCl$_4$ in a flask and stirred to dissolve, and 14.6 g of NBS and 6.7 g of AIBN were added dropwise at 0° C. After heating under reflux for 5 hours or longer, upon completion of the reaction, distilled water was slowly added dropwise, extracted with MC, washed with brine, dried over anhydrous magnesium sulfate, and then concentrated. Thereafter, the reaction product was separated by silica column chromatography to give the title compound.

$^1$H NMR (400 MHz, CDCl$_3$): δ 7.95 (2H, d), 7.50 (2H, d), 4.52 (2H, s), 2.62 (3H, s).

Step 2: Preparation of (S)-ethyl 3-(4-(4-(acetylbenzyloxy)phenyl)hex-4-ynoate

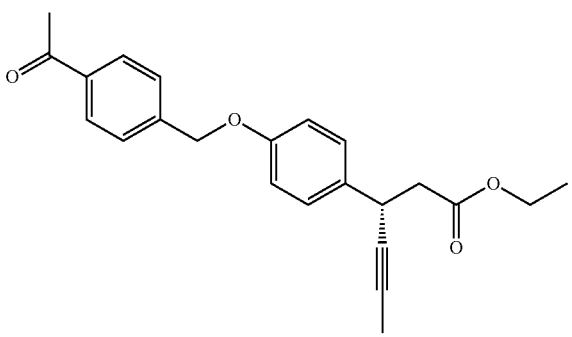 [SMILES: CC#C[C@@H](CC(=O)OCC)c1ccc(OCc2ccc(C(C)=O)cc2)cc1]

The title compound was obtained by the same method as in step 2 in Preparative Example 6 except that (S)-ethyl 3-(4-hydroxyphenyl)hex-4-ynoate obtained in Preparative Example 2 and 1-(4-(bromomethyl)phenyl)ethanone obtained in step 1 were used.

$^1$H NMR (400 MHz, CDCl$_3$): δ 7.99 (2H, d), 7.53 (2H, d) 7.31 (2H, d), 6.92 (2H, d), 5.13 (2H, s), 4.15 (2H, m), 4.09 (1H, m), 2.75 (2H, m), 2.64 (3H, s), 1.84 (3H, d), 1.24 (3H, m).

Step 3: Preparation of (3S)-ethyl 3-(4-(4-(1-hydroxyethyl)benzyloxy)phenyl)hex-4-ynoate

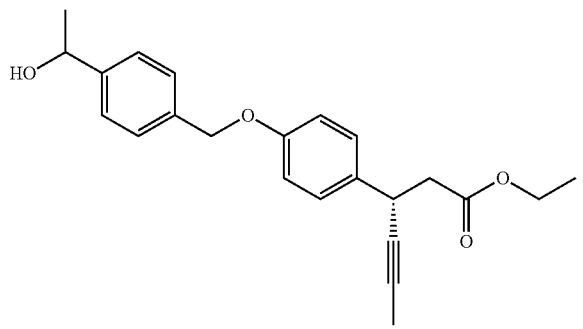 [SMILES: CC#C[C@@H](CC(=O)OCC)c1ccc(OCc2ccc(C(C)O)cc2)cc1]

Under a nitrogen atmosphere, 1.0 g of (S)-ethyl 3-(4-(4-acetylbenzyloxy)phenyl)hex-4-ynoate obtained in step 2 was added to 50 mL of THF in a flask and stirred to dissolve, and then 0.16 g of NaBH$_4$ was added dropwise at 0° C. After stirring at room temperature for 2 hours or longer, upon completion of the reaction, distilled water was slowly added dropwise, extracted with EA, washed with brine, dried over anhydrous magnesium sulfate, and then concentrated to give the title compound.

$^1$H NMR (400 MHz, CDCl$_3$): δ 8.02 (2H, d), 7.57 (2H, d) 7.36 (2H, d), 6.99 (2H, d), 5.21 (2H, s), 4.23 (2H, m), 4.17 (1H, m), 3.81 (1H, s), 2.75 (2H, m), 2.64 (3H, s), 1.84 (3H, d), 1.24 (3H, m).

Step 4: Preparation of (3S)-ethyl 3-(4-(4-(1-bromoethyl)benzyloxy)phenyl)hex-4-ynoate

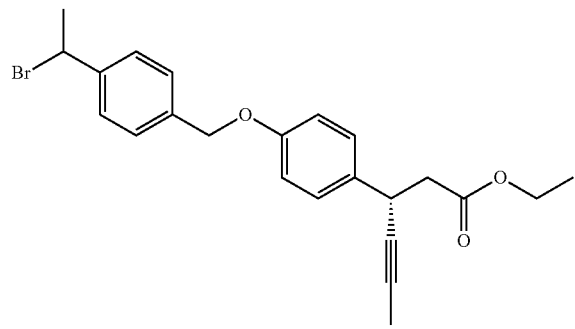 [SMILES: CC#C[C@@H](CC(=O)OCC)c1ccc(OCc2ccc(C(C)Br)cc2)cc1]

Under a nitrogen atmosphere, 0.76 g of (3S)-ethyl 3-(4-(4-(1-hydroxyethyl)benzyloxy)phenyl)hex-4-ynoate obtained in step 3 was added to 50 mL of MC in a flask and stirred to dissolve, and then 0.6 g of triphenylphosphine and 0.75 g of CBr$_4$ were added dropwise at 0° C. After stirring at room temperature for 2 hours or longer, upon completion of the reaction, distilled water was slowly added dropwise, extracted with EA, washed with brine, dried over anhydrous magnesium sulfate, and then concentrated to give the title compound.

$^1$H NMR (400 MHz, CDCl$_3$): δ 8.02 (2H, d), 7.57 (2H, d) 7.36 (2H, d), 6.99 (2H, d), 5.21 (2H, s), 4.23 (2H, m), 4.17 (1H, m), 3.92 (1H, s), 2.85 (2H, m), 2.44 (3H, s), 1.86 (3H, d), 1.27 (3H, m).

<Preparative Example 13> Preparation of 2-(piperazin-1-yl)benzo[d]thiazole hydrochloride Step 1: Preparation of tert-butyl 4-(benzo[d]thiazol-2-yl)piperazine-1-carboxylate

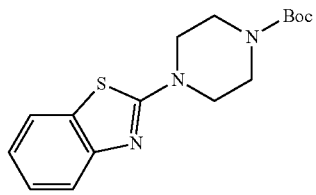 [SMILES: CC(C)(C)OC(=O)N1CCN(c2nc3ccccc3s2)CC1]

Under a nitrogen atmosphere, 2.0 g of tert-butyl piperazine-1-carboxylate was added to AN/distilled water (100/50 mL) in a flask and stirred to dissolve, and then 2.1 mL of DIPEA was added dropwise at 0° C. Thereafter, 0.9 g of 2-chlorobenzo[d]thiazole was added dropwise thereto, and the mixture was heated under reflux for 2 hours or longer. Upon completion of the reaction, distilled water was slowly added dropwise, extracted with EA, washed with brine, dried over anhydrous magnesium sulfate, and then concentrated to give the title compound.

$^1$H NMR (400 MHz, CDCl$_3$): δ 7.61 (1H, d), 7.60 (1H, d), 7.29 (1H, m), 7.09 (1H, m), 3.77 (4H, m), 2.62 (4H, m), 1.52 (9H, s).

Step 2: Preparation of 2-(piperazin-1-yl)benzo[d]thiazole hydrochloride

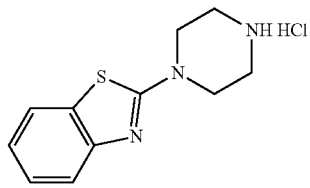

The title compound was obtained by the same method as in step 2 in Preparative Example 9 except that tert-butyl 4-(benzo[d]thiazol-2-yl)piperazine-1-carboxylate obtained in step 1 was used instead of tert-butyl 4-(4-(methylsulfonyl)phenyl)-5,6-dihydropyridine-1(2H)-carboxylate.

$^1$H NMR (400 MHz, D$_2$O): δ 7.61 (1H, d), 7.60 (1H, d), 7.29 (1H, m), 7.09 (1H, m), 3.77 (4H, m), 2.62 (4H, m).

<Preparative Example 14> Preparation of 2-(piperazin-1-yl)-5-propylpyrimidine hydrochloride Step 1: Preparation of tert-butyl 4-(5-propylpyrimidin-2-yl)piperazine-1-carboxylate

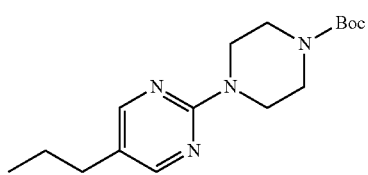 [SMILES: CCCc1cnc(N2CCN(C(=O)OC(C)(C)C)CC2)nc1]

The title compound was obtained by the same method as in step 1 in Preparative Example 13 except that 2-chloro-5-propylpyrimidine was used instead of 2-chlorobenzo[d]thiazole.

$^1$H NMR (400 MHz, CDCl$_3$): δ 8.19 (2H, s), 3.77 (4H, m), 2.62 (4H, m), 2.41 (2H, m), 1.61 (2H, m), 1.52 (9H, s), 0.96 (3H, m).

Step 2: Preparation of 2-(piperazin-1-yl)-5-propylpyrimidine hydrochloride

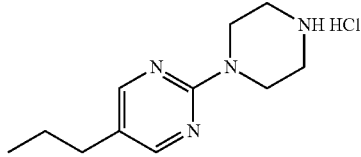

The title compound was obtained by the same method as in step 2 in Preparative Example 9 except that tert-butyl 4-(5-propylpyrimidin-2-yl)piperazine-1-carboxylate obtained in step 1 was used instead of tert-butyl 4-(4-(methylsulfonyl)phenyl)-5,6-dihydropyridine-1(2H)-carboxylate.

$^1$H NMR (400 MHz, D$_2$O): δ 8.19 (2H, s), 3.77 (4H, m), 2.62 (4H, m), 2.41 (2H, m), 1.61 (2H, m), 0.96 (3H, m).

<Preparative Example 15> Preparation of 6-(piperazin-1-yl)nicotinonitrile hydrochloride Step 1: Preparation of tert-butyl 4-(5-cyanopyridin-2-yl)piperazine-1-carboxylate

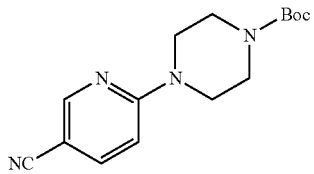 [SMILES: CC(C)(C)OC(=O)N1CCN(c2ccc(C#N)cn2)CC1]

The title compound was obtained by the same method as in step 1 in Preparative Example 13 except that 6-chloronicotinonitrile was used instead of 2-chlorobenzo[d]thiazole.

$^1$H NMR (400 MHz, CDCl$_3$): δ 8.41 (1H, s) 7.61 (1H, d), 6.59 (1H, d), 3.77 (4H, m), 2.62 (4H, m), 1.52 (9H, s).

Step 2: Preparation of 6-(piperazin-1-yl)nicotinonitrile hydrochloride

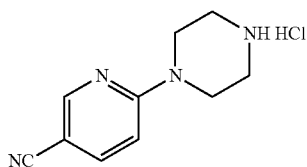

The title compound was obtained by the same method as in step 2 in Preparative Example 9 except that tert-butyl 4-(5-cyanopyridin-2-yl)piperazine-1-carboxylate obtained in step 1 was used instead of tert-butyl 4-(4-(methylsulfonyl)phenyl)-5,6-dihydropyridine-1(2H)-carboxylate.

$^1$H NMR (400 MHz, D$_2$O): δ 8.41 (1H, s), 7.61 (1H, d), 6.59 (1H, d), 3.77 (4H, m), 2.62 (4H, m).

<Preparative Example 16> Preparation of (S)-ethyl 3-(4-(4-(2-(methylsulfonyloxy) ethyl)benzyloxy)phenyl)hex-4-ynoate Step 1: Preparation of 2-(4-(bromomethyl)phenyl)ethanol

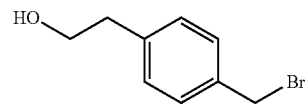 [SMILES: OCCc1ccc(CBr)cc1]

Under a nitrogen atmosphere, 5 g of 2-(4-(bromomethyl)phenyl)acetic acid and 100 mL of THF were loaded in a flask and stirred to dissolve, and then 70 mL of a borane-THF solution was slowly added dropwise at 0° C. After stirring for 2 hours, upon completion of the reaction, the temperature was lowered to 0° C., and distilled water was slowly added dropwise, followed by extraction using EA. The extracted organic layer was dried under reduced pressure to give the title compound.

$^1$H NMR (400 MHz, CDCl$_3$): 37 (2H, d), 7.24 (2H, d), 4.51 (2H, s), 3.89 (2H, m), 2.89 (2H, m).

Step 2: Preparation of (S)-ethyl 3-(4-(4-(2-hydroxyethyl)benzyloxy)phenyl)hex-4-ynoate

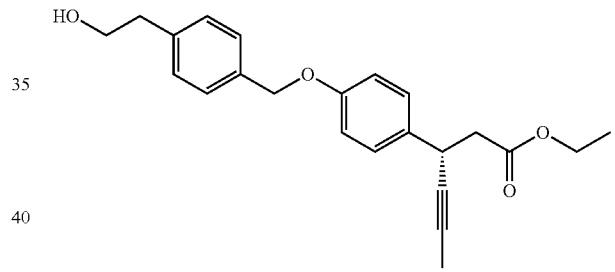

The title compound was obtained by the same method as in step 2 in Preparative Example 5 except that 2-(4-(bromomethyl)phenyl)ethanol obtained in step 1 was used instead of 4-(bromomethyl)phenyl)methanol.

$^1$H NMR (400 MHz, CDCl$_3$): δ 7.40 (2H, d), 7.30 (2H, d), 7.27 (2H, d), 6.95 (2H, d), 5.04 (2H, s), 4.18 (2H, m), 4.11 (1H, m), 3.89 (2H, m), 2.91 (2H, m), 2.71 (2H, m), 1.84 (3H, s), 1.38 (1H, m), 1.25 (3H, m).

Step 3: Preparation of (S)-ethyl 3-(4-(4-(2-(methylsulfonyloxy)ethyl)benzyloxy) phenyl)hex-4-ynoate

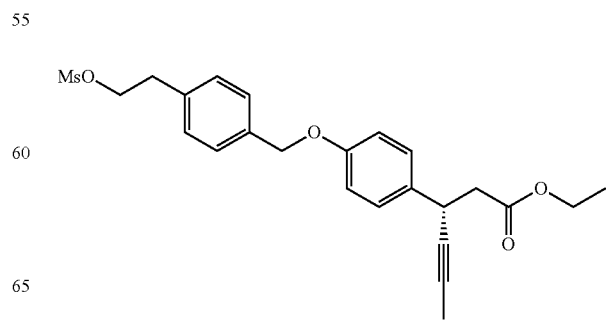

The title compound was obtained by the same method as in step 3 in Preparative Example 6 except that (S)-ethyl 3-(4-(4-(2-hydroxyethyl)benzyloxy)phenyl)hex-4-ynoate obtained in step 2 was used instead of ethyl 3-(4-(4-(hydroxymethyl)benzyloxy)phenyl)hex-4-ynoate.

$^1$H NMR (400 MHz, CDCl$_3$): δ 7.40 (2H, d), 7.30 (2H, d), 7.27 (2H, d), 6.95 (2H, d), 5.04 (2H, s), 4.18 (2H, m), 4.11 (1H, m), 3.99 (2H, m), 2.95 (3H, s), 2.93 (2H, m), 2.71 (2H, m), 1.84 (3H, s), 1.25 (3H, m).

<Example 1> Preparation of 3-(4-(3-(1,4-dioxaspiro[4.5]dec-7-en-8-yl)benzyloxy) phenyl)hex-4-ynoic acid

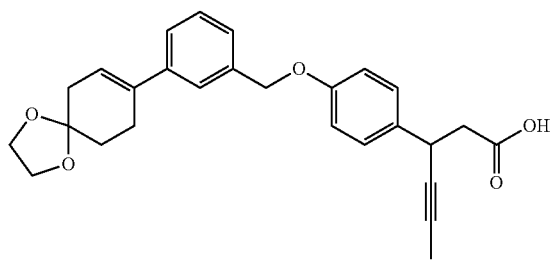 [SMILES: CC#CC(CC(=O)O)c1ccc(OCc2cccc(C3=CCC4(CC3)OCCO4)c2)cc1]

Step 1: Preparation of ethyl 3-(4-(3-(1,4-dioxaspiro[4.5]dec-7-en-8-yl)benzyloxy) phenyl)hex-4-ynoate Under a nitrogen atmosphere, (3-(1,4-dioxaspiro[4.5]dec-7-en-8-yl)phenyl)methanol (19.54 g) prepared in Preparative Example 4 and tetrahydrofuran (80 mL) were loaded in a 500-mL flask and stirred to dissolve, and then ethyl 3-(4-hydroxyphenyl)hex-4-ynoate (18.42 g) prepared in Preparative Example 1 and triphenyl phosphine (31.21 g) were slowly added. Thereafter, diisopropyl azodicarboxylate (23.4 mL) was slowly added dropwise using a dropping funnel at 0° C., and then stirred for 4 hours or longer while the temperature was raised to room temperature. Upon completion of the reaction, distilled water (200 mL) was slowly added dropwise and extracted with ethylacetate (300 mL), and then the extracted organic layer was dried under reduced pressure to give the title compound (32.1 g, 87.9%).

$^1$H NMR (400 MHz, CDCl$_3$): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of 3-(4-(3-(1,4-dioxaspiro[4.5]dec-7-en-8-yl)benzyloxy)phenyl) hex-4-ynoic acid Under a nitrogen atmosphere, ethyl 3-(4-(3-(1,4-dioxaspiro[4.5]dec-7-en-8-yl)benzyloxy)phenyl)hex-4-ynoate (32.1 g) prepared in step 1, methanol (50 mL), and distilled water (50 mL) were loaded in a 500-mL flask and stirred to dissolve, and then potassium hydroxide (19.5 g) was slowly added at room temperature, followed by stirring for one hour or longer. Upon completion of the reaction, the mixture was acidified with a 1 M hydrochloric acid aqueous solution to a pH of 2-3, extracted with ethyl acetate (300 mL), and dried under reduced pressure to give the title compound (24.1 g, 79.9%).

$^1$H NMR (400 MHz, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

<Example 2> Preparation of L-lysine 3-(4-(3-(1,4-dioxaspiro[4.5]dec-7-en-8-yl)benzyloxy)phenyl)hex-4-ynoate

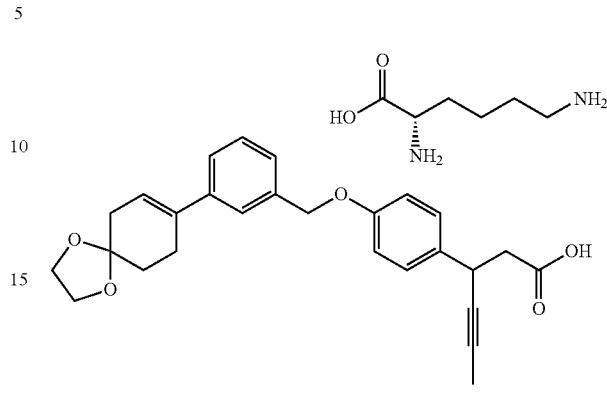

Under a nitrogen atmosphere, 3-(4-(3-(1,4-dioxaspiro[4.5]dec-7-en-8-yl)benzyloxy)phenyl)hex-4-ynoic acid (24.1 g) prepared in Example 1 and ethanol (170 mL) were loaded in a 500-mL flask and stirred to dissolve, and then L-lysine (7.33 g) was added thereto. Thereafter, the reaction temperature was raised to 50° C., and the mixture was stirred for 30 minutes at 50° C., and again cooled to room temperature, followed by stirring for 30 minutes. Upon completion of the reaction, the produced solid was filtered to give the title compound (31.5 g, 73.3%).

$^1$H NMR (400 MHz, D$_2$O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

<Example 3> Preparation of 4-(4-(3-(1,4-dioxaspiro[4.5]dec-7-en-8-yl)benzyloxy)phenyl)hex-4-ynoic Acid

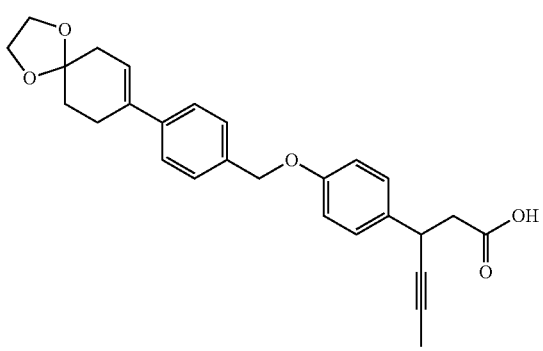 [SMILES: CC#CC(CC(=O)O)c1ccc(OCc2ccc(C3=CCC4(CC3)OCCO4)cc2)cc1]

Step 1: Preparation of ethyl 4-(4-(3-(1,4-dioxaspiro[4.5]dec-7-en-8-yl)benzyloxy)phenyl)hex-4-ynoate Under a nitrogen atmosphere, (4-(1,4-dioxaspiro[4.5]dec-7-en-8-yl)phenyl)methanol (1.5 g) prepared in Preparative Example 5 and tetrahydrofuran (20 mL) were loaded in a 100-mL flask and stirred to dissolve, and then ethyl 3-(4-hydroxyphenyl)hex-4-ynoate (1.41 g) prepared in Preparative Example 1 and triphenyl phosphine (2.39 g) were slowly added. Thereafter, diisopropyl azodicarboxylate (9.38 mL) was slowly added dropwise using a dropping funnel at 0° C., and then stirred for 4 hours or longer while the temperature was raised to room temperature. Upon completion of the reaction, distilled water (50 mL) was slowly added dropwise, followed by extraction using ethylacetate (100 mL), and then the extracted organic layer was dried under reduced pressure to give the title compound (1.38 g, 49.2%).

$^{1}$H NMR (400 MHz, CDCl$_{3}$): δ 7.42 (2H, d), 7.37 (2H, d), 7.30 (2H, d), 6.92 (2H, d), 6.01 (1H, s), 5.01 (2H, s), 4.14 (2H, m), 4.06 (5H, m), 2.70 (4H, m), 2.49 (2H, s), 1.94 (2H, t), 1.84 (3H, d), 1.24 (3H, t).

Step 2: Preparation of 4-(4-(3-(1,4-dioxaspiro[4.5]dec-7-en-8-yl)benzyloxy) phenyl)hex-4-ynoic acid Under a nitrogen atmosphere, ethyl 4-(4-(3-(1,4-dioxaspiro[4.5]dec-7-en-8-yl)benzyloxy)phenyl)hex-4-ynoate (1.38 g) prepared in step 1, methanol (10 mL), and distilled water (10 mL) were loaded in a 500-mL flask and stirred to dissolve, and then potassium hydroxide (1.25 g) was slowly added at room temperature, followed by stirring for one hour or longer. Upon completion of the reaction, the mixture was acidified with a 1 M hydrochloric acid aqueous solution to a pH of 2-3, extracted with ethyl acetate (50 mL), and dried under reduced pressure to give the title compound (0.98 g, 75.6%).

$^{1}$H NMR (400 MHz, CDCl$_{3}$): δ 7.41 (2H, d), 7.36 (2H, d), 7.29 (2H, d), 6.92 (2H, d), 6.01 (1H, s), 5.01 (2H, s), 4.04 (5H, m), 2.77 (4H, m), 2.49 (2H, s), 1.96 (2H, t), 1.83 (3H, d).

<Example 4> Preparation of 3-(4-(3-(4-oxocyclohex-1-enyl)benzyloxy)phenyl)hex-4-ynoic acid

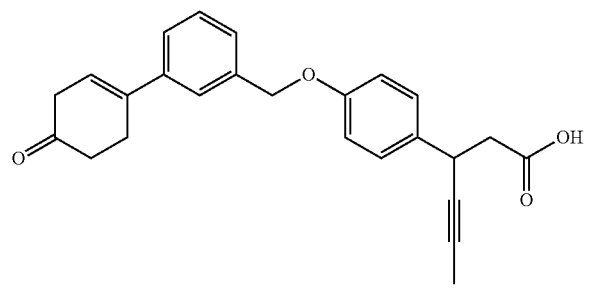 [SMILES: CC#CC(CC(=O)O)c1ccc(OCc2cccc(C3=CCC(=O)CC3)c2)cc1]

Under a nitrogen atmosphere, 3-(4-(3-(1,4-dioxaspiro[4.5]dec-7-en-8-yl)benzyloxy)phenyl)hex-4-ynoic acid (1 g) prepared in Example 1 and tetrahydrofurane (5 mL) were loaded and stirred to dissolve, and then a 6 N hydrochloric acid aqueous solution (5 mL) was added, and the mixture was stirred at room temperature for 1 hour or longer. Upon completion of the reaction, distilled water (50 mL) was slowly added dropwise, followed by extraction using ethylacetate (50 mL), and then the extracted organic layer was dried under reduced pressure to give the title compound (0.76 g, 84.6%).

$^{1}$H NMR (400 MHz, CDCl$_{3}$): δ 7.48 (1H, s), 7.40 (5H, m), 6.94 (2H, d), 6.13 (1H, s), 5.07 (2H, s), 4.05 (1H, m), 3.10 (1.5H, t), 2.93 (1.5H, t), 2.82 (2H, m), 2.67 (2H, t), 1.85 (3H, s).

<Example 5> Preparation of 3-(4-(3-(4-hydroxycyclohex-1-enyl)benzyloxy) phenyl)hex-4-ynoic Acid

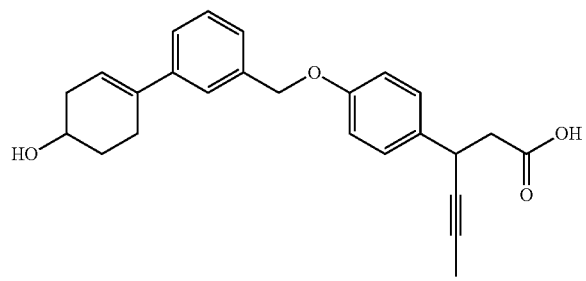 [SMILES: CC#CC(CC(=O)O)c1ccc(OCc2cccc(C3=CCC(O)CC3)c2)cc1]

Under a nitrogen atmosphere, 3-(4-(3-(4-oxocyclohex-1-enyl)benzyloxy)phenyl)hex-4-ynoic acid (1 g) prepared in Example 4 and ethanol (10 mL) were loaded in a 100-mL flask and stirred to dissolve, and then sodium borohydride (0.3 g) was added, followed by stirring at room temperature for 3 hours or longer. Upon completion of the reaction, the mixture was acidified with a 1 M hydrochloric acid aqueous solution to a pH of 4-5, and extracted with ethyl acetate (100 mL) and distilled water (100 mL). The extracted organic layer was dried under reduced pressure to give the title compound (0.81 g, 80.6%).

$^{1}$H NMR (400 MHz, CDCl$_{3}$): δ 7.44 (1H, s), 7.33 (5H, m), 6.93 (2H, d), 6.02 (1H, s), 5.03 (2H, s), 4.08 (2H, s), 2.78 (2H, m), 2.55 (2.5H, m), 2.22 (1H, m), 2.04 (1H, m), 1.85 (3H, s).

<Example 6> Preparation of L-lysine 3-(4-(3-(4-hydroxycyclohex-1-enyl)benzyloxy)phenyl)hex-4-ynoate

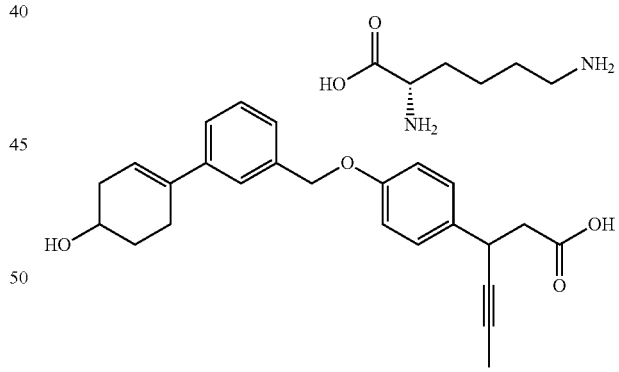

Under a nitrogen atmosphere, 3-(4-(3-(4-hydroxycyclohex-1-enyl)benzyloxy)phenyl)hex-4-ynoic acid (1 g) prepared in Example 5 and ethanol (170 mL) were loaded in a 100-mL flask and stirred to dissolve, and then L-lysine (0.7 g) was added thereto. Thereafter, the reaction temperature was raised to 50° C., and the mixture was stirred for 30 minutes at 50° C., and again cooled to room temperature, followed by stirring for 30 minutes. Upon completion of the reaction, the produced solid was filtered to give the title compound (0.95 g, 69.1%).

$^{1}$H NMR (400 MHz, D$_{2}$O): δ 7.11 (3H, m), 6.99 (3H, m), 6.64 (2H, d), 5.65 (1H, s), 4.59 (2H, s), 3.79 (1H, s), 3.60

(1H, t), 2.88 (2H, t), 2.35 (2H, d), 2.23 (2H, s), 2.14 (2H, s), 1.75 (2H, m), 1.59 (7H, m), 1.38 (2H, m).

<Example 7> Preparation of (3S)-3-(4-(3-(1,4-dioxaspiro[4.5]dec-7-en-8-yl)benzyloxy)phenyl)hex-4-ynoic Acid

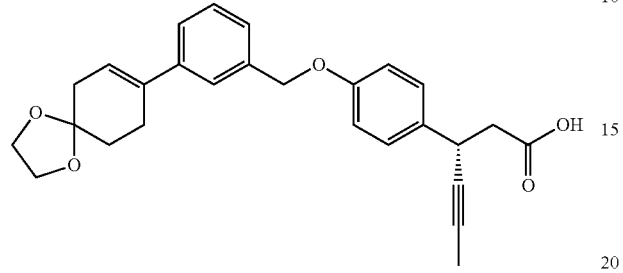

Step 1: Preparation of ethyl-(3S)-3-(4-(3-(1,4-dioxaspiro[4.5]dec-7-en-8-yl)benzyloxy)phenyl)hex-4-ynoate Under a nitrogen atmosphere, (3-(1,4-dioxaspiro[4.5]dec-7-en-8-yl)phenyl)methanol (19.54 g) prepared in Preparative Example 4 and tetrahydrofuran (80 mL) were loaded in a 500-mL flask and stirred to dissolve, and then (S)-ethyl 3-(4-hydroxyphenyl)hex-4-ynoate (18.42 g) prepared in Preparative Example 2 and triphenyl phosphine (31.21 g) were slowly added. Thereafter, diisopropyl azodicarboxylate (23.4 mL) was slowly added dropwise using a dropping funnel at 0° C., and then stirred for 4 hours or longer while the temperature was raised to room temperature. Upon completion of the reaction, distilled water (200 mL) was slowly added dropwise and extracted with ethylacetate (300 mL), and then the extracted organic layer was dried under reduced pressure to give the title compound.

$^1$H NMR (400 MHz, CDCl$_3$): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of (3S)-3-(4-(3-(1,4-dioxaspiro[4.5]dec-7-en-8-yl)benzyloxy) phenyl)hex-4-ynoic acid Under a nitrogen atmosphere, ethyl-(3S)-3-(4-(3-(1,4-dioxaspiro[4.5]dec-7-en-8-yl)benzyloxy)phenyl)hex-4-ynoate (32.1 g) prepared in step 1, methanol (50 mL), and distilled water (50 mL) were loaded in a 500-mL flask and stirred to dissolve, and then potassium hydroxide (19.5 g) was slowly added at room temperature, followed by stirring for one hour or longer. Upon completion of the reaction, the mixture was acidified with a 1 M hydrochloric acid aqueous solution to a pH of 2-3, extracted with ethyl acetate (300 mL), and dried under reduced pressure to give the title compound (24.1 g, 66.2%).

$^1$H NMR (400 MHz, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

<Example 8> Preparation of (3R)-3-(4-(3-(1,4-dioxaspiro[4.5]dec-7-en-8-yl)benzyloxy)phenyl)hex-4-ynoic acid

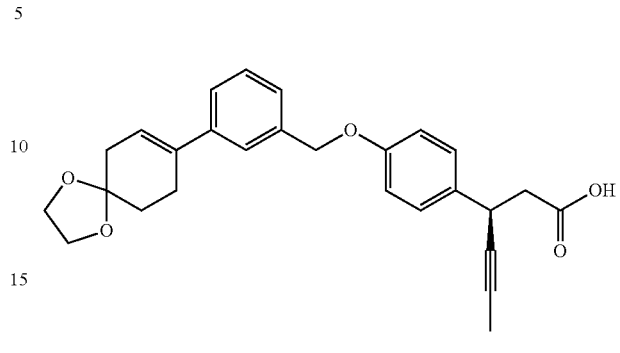

Step 1: Preparation of ethyl-(3R)-3-(4-(3-(1,4-dioxaspiro[4.5]dec-7-en-8-yl)benzyloxy)phenyl)hex-4-ynoate Under a nitrogen atmosphere, (3-(1,4-dioxaspiro[4.5]dec-7-en-8-yl)phenyl)methanol (19.54 g) prepared in Preparative Example 4 and tetrahydrofuran (80 mL) were loaded in a 500-mL flask and stirred to dissolve, and then (R)-ethyl 3-(4-hydroxyphenyl)hex-4-ynoate (18.42 g) prepared in Preparative Example 3 and triphenyl phosphine (31.21 g) were slowly added. Thereafter, diisopropyl azodicarboxylate (23.4 mL) was slowly added dropwise using a dropping funnel at 0° C., and then stirred for 4 hours or longer while the temperature was raised to room temperature. Upon completion of the reaction, distilled water (200 mL) was slowly added dropwise and extracted with ethylacetate (300 mL), and then the extracted organic layer was dried under reduced pressure to give the title compound.

$^1$H NMR (400 MHz, CDCl$_3$): δ 7.46 (1H, s), 7.31 (5H, m), 6.93 (2H, d), 6.02 (1H, m), 5.04 (2H, s), 4.13 (2H, m), 4.08 (1H, m), 4.04 (4H, s), 2.69 (4H, m), 2.49 (2H, s), 1.94 (2H, t), 1.84 (3H, d), 1.31 (3H, t).

Step 2: Preparation of (3R)-3-(4-(3-(1,4-dioxaspiro[4.5]dec-7-en-8-yl)benzyloxy) phenyl)hex-4-ynoic acid Under a nitrogen atmosphere, ethyl-(3R)-3-(4-(3-(1,4-dioxaspiro[4.5]dec-7-en-8-yl)benzyloxy)phenyl)hex-4-ynoate (32.1 g) prepared in step 1, methanol (50 mL), and distilled water (50 mL) were loaded in a 500-mL flask and stirred to dissolve, and then potassium hydroxide (19.5 g) was slowly added at room temperature, followed by stirring for one hour or longer. Upon completion of the reaction, the mixture was acidified with a 1 M hydrochloric acid aqueous solution to a pH of 2-3, extracted with ethyl acetate (300 mL), and dried under reduced pressure to give the title compound (17.3 g, 47.5%).

$^1$H NMR (400 MHz, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s).

<Example 9> Preparation of L-lysine (3S)-3-(4-(3-(1,4-dioxaspiro[4.5]dec-7-en-8-yl)benzyloxy)phenyl)hex-4-ynoate

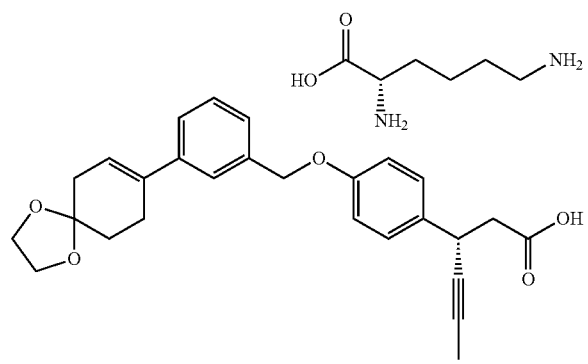

Under a nitrogen atmosphere, (3S)-3-(4-(3-(1,4-dioxaspiro[4.5]dec-7-en-8-yl)benzyloxy)phenyl)hex-4-ynoic acid (24.1 g) prepared in Example 7 and ethanol (170 mL) were loaded in a 500-mL flask and stirred to dissolve, and then L-lysine (7.33 g) was added thereto. Thereafter, the reaction temperature was raised to 50° C., and the mixture was stirred for 30 minutes at 50° C., and again cooled to room temperature, followed by stirring for 30 minutes. Upon completion of the reaction, the produced solid was filtered to give the title compound (22.5 g, 69.8%).

$^1$H NMR (400 MHz, D$_2$O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

<Example 10> Preparation of L-lysine (3R)-3-(4-(3-(1,4-dioxaspiro[4.5]dec-7-en-8-yl)benzyloxy)phenyl)hex-4-ynoate

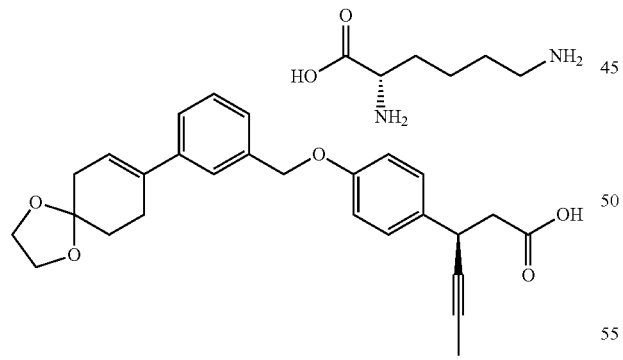

Under a nitrogen atmosphere, (3R)-3-(4-(3-(1,4-dioxaspiro[4.5]dec-7-en-8-yl)benzyloxy)phenyl)hex-4-ynoic acid (24.1 g) prepared in Example 8 and ethanol (170 mL) were loaded in a 500-mL flask and stirred to dissolve, and then L-lysine (7.33 g) was added thereto. Thereafter, the reaction temperature was raised to 50° C., and the mixture was stirred for 30 minutes at 50° C., and again cooled to room temperature, followed by stirring for 30 minutes. Upon completion of the reaction, the produced solid was filtered to give the title compound (16.2 g, 71.4%).

$^1$H NMR (400 MHz, D$_2$O): δ 7.11 (3H, m), 6.99 (3H, m), 6.64 (2H, d), 5.65 (1H, s), 4.59 (2H, s), 3.79 (5H, s), 3.60 (1H, t), 2.88 (2H, t), 2.35 (2H, d), 2.23 (2H, s), 2.14 (2H, s), 1.75 (2H, m), 1.59 (7H, m), 1.38 (2H, m).

<Example 11> Preparation of sodium (3S)-3-(4-(3-(1,4-dioxaspiro[4.5]dec-7-en-8-yl)benzyloxy)phenyl)hex-4-ynoate

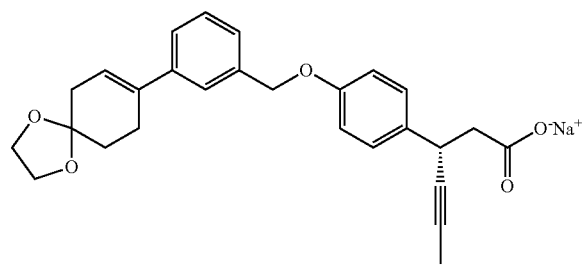

Under a nitrogen atmosphere, (3S)-3-(4-(3-(1,4-dioxaspiro[4.5]dec-7-en-8-yl)benzyloxy)phenyl)hex-4-ynoic acid (1 g) prepared in Example 7 and ethanol (170 mL) were loaded in a 500-mL flask and stirred to dissolve, and then a 3 N sodiumhydroxide aqueous solution (0.77 mL) was added dropwise. Thereafter, the mixture was stirred at room temperature, and upon completion of the reaction, the reaction solution was concentrated under reduced pressure, followed by addition of isopropylalcohol (10 mL), and the produced solid was filtered to give the target compound (0.73 g, 69.2%).

$^1$H NMR (400, CDCl$_3$): δ 7.44 (1H, s), 7.34 (5H, m), 6.91 (2H, d), 6.00 (1H, t), 5.02 (2H, s), 4.08 (1H, m), 4.04 (4H, s), 2.73 (4H, m), 2.48 (2H, s), 1.92 (2H, t), 1.82 (3H, s)

<Example 12> Preparation of 3-(4-(4-((3,4-dihydroisoquinolin-2(1H)-yl)methyl)benzyloxy)phenyl)hex-4-ynoic acid

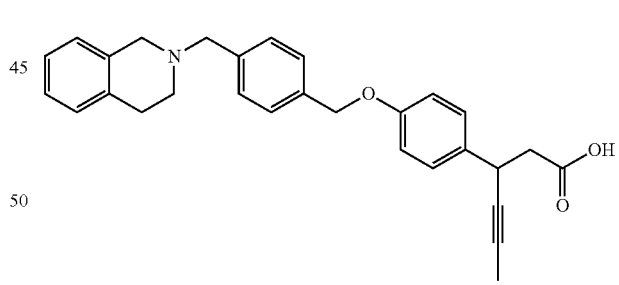

Step 1: Preparation of ethyl 3-(4-(4-((3,4-dihydroisoquinolin-2(1H)-yl)methyl)benzyloxy)phenyl)hex-4-ynoate Under a nitrogen atmosphere, 0.5 g of 1,2,3,4-tetrahydroisoquinoline was added to 20 mL of DMF in a flask and stirred to dissolve, and then 1.2 g of cesium carbonate was added at room temperature. After 30 minutes, 1.0 g of ethyl 3-(4-(4-((methylsulfonyloxy)methyl)benzyloxy)phenyl)hex-4-ynoate was added dropwise, followed by stirring at room temperature for 12 hours. Upon completion of the reaction, distilled water was slowly added dropwise, extracted with ethyl acetate, washed with brine, dried over anhydrous magnesium sulfate, and then concentrated. Thereafter, the reaction product was separated by silica column chromatography to give the title compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.14 (2H, m), 4.09 (1H, s), 3.91 (1H, d), 3.70 (3H, m), 2.92 (4H, s), 2.73 (2H, m), 1.83 (3H, s), 1.29 (3H, m).

Step 2: Preparation of 3-(4-(4-(((3,4-dihydroisoquinolin-2(1H)-yl)methyl) benzyloxy)phenyl)hex-4-ynoic acid Under a nitrogen atmosphere, 0.7 g of ethyl 3-(4-(4-(3,4-dihydroisoquinolin-2(1H)-yl)methyl)benzyloxy)phenyl) hex-4-ynoate prepared in step 1 was added to THF, methanol, and distilled water in a flask and stirred to dissolve, and then, 0.7 g of lithium hydroxide was slowly added at room temperature, followed by stirring for 1 hour or longer. Upon completion of the reaction, the mixture was acidified with a 1 M hydrochloric acid aqueous solution to a pH of 2-3, extracted with ethyl acetate, and dried under reduced pressure to give the title compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.09 (1H, s), 3.91 (1H, d), 3.70 (3H, m), 2.92 (4H, s), 2.73 (2H, m), 1.83 (3H, s).

<Example 13> Preparation of 3-(4-(3-cyclohexenyl-4-((3,4-dihydroisoquinolin-2(1H)-yl)methyl)benzyloxy)phenyl)hex-4-ynoic acid

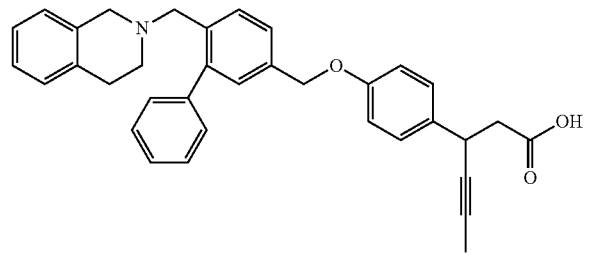 [SMILES: CC#CC(CC(=O)O)c1ccc(OCc2ccc(CN3CCc4ccccc4C3)c(-c3ccccc3)c2)cc1]

Step 1: Preparation of ethyl 3-(4-(3-cyclohexenyl-4-((3,4-dihydroisoquinolin-2(1H)-yl)methyl)benzyloxy)phenyl)hex-4-ynoate Under a nitrogen atmosphere, 1.0 g of (3-cyclohexenyl-4-((3,4-dihydroisoquinolin-2(1H)-yl)methyl)phenyl)methanol and 30 mL of tetrahydrofuran were loaded in a flask and stirred to dissolve, and then 0.8 g of ethyl 3-(4-hydroxyphenyl)hex-4-ynoate prepared in Preparative Example 1 and 0.6 g of triphenyl phosphine were slowly added. Thereafter, 0.5 mL of diisopropyl azodicarboxylate was slowly added dropwise using a dropping funnel at 0° C., and then stirred for 4 hours or longer while the temperature was raised to room temperature. Under completion of the reaction, distilled water was slowly added dropwise, followed by extraction using ethyl acetate, and the extracted organic layer was dried under reduced pressure to give the title compound.

$^1$H NMR (400 MHz, CDCl$_3$): δ 12.56 (1H, s), 8.26 (1H, d), 7.43 (2H, d), 7.25 (6H, m), 7.21 (1H, d), 7.02 (1H, d), 6.89 (2H, d), 5.46 (1H, s), 5.03 (2H, s), 4.14 (2H, m), 4.05 (1H, s), 3.92 (1H, s), 3.70 (1H, s), 3.35 (1H, s), 3.27 (1H, s), 3.03 (1H, s), 2.83 (2H, m), 2.01 (4H, m), 1.84 (3H, d), 1.51 (4H, m), 1.29 (3H, m).

Step 2: Preparation of 3-(4-(3-cyclohexenyl-4-((3,4-dihydroisoquinolin-2(1H)-yl)methyl)benzyloxy)phenyl)hex-4-ynoic acid The title compound was obtained by the same method as in step 2 in Example 12 except that ethyl 3-(4-(3-cyclohexenyl-4-((3,4-dihydroisoquinolin-2(1H)-yl)methyl)benzyloxy)phenyl)hex-4-ynoate was used instead of ethyl 3-(4-(4-((3,4-dihydroisoquinolin-2(1H)-yl)methyl)benzyloxy)phenyl)hex-4-ynoate.

$^1$H NMR (400 MHz, CDCl$_3$): δ 12.56 (1H, s), 8.26 (1H, d), 7.43 (2H, d), 7.25 (6H, m), 7.21 (1H, d), 7.02 (1H, d), 6.89 (2H, d), 5.46 (1H, s), 5.03 (2H, s), 4.05 (1H, s), 3.92 (1H, s), 3.70 (1H, s), 3.35 (1H, s), 3.27 (1H, s), 3.03 (1H, s), 2.83 (2H, m), 2.01 (4H, m), 1.84 (3H, d), 1.51 (4H, m).

<Example 14> Preparation of 3-(4-(4-((4-phenyl-5,6-dihydropyridin-1(2H)-yl)methyl)benzyloxy)phenyl)hex-4-ynoic acid

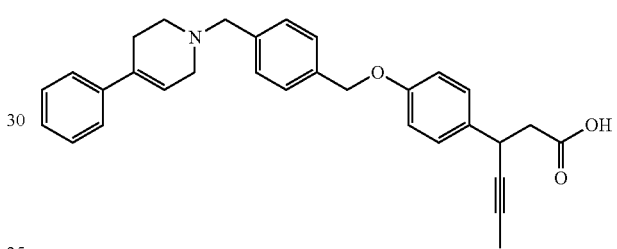

The title compound was obtained by the same method as in Example 12 except that 4-phenyl-1,2,3,6-tetrahydropyridine hydrochloride was used instead of 1,2,3,4-tetrahydroisoquinoline.

$^1$H NMR (400 MHz, CDCl$_3$): δ 7.25 (2H, d), 6.78 (2H, d), 4.95 (1H, s), 4.14 (2H, m), 4.04 (1H, m), 2.68 (2H, m), 1.84 (3H, d), 1.29 (3H, t).

<Example 15> Preparation of 3-(4-(4-((4-phenylpiperazin-1-yl)methyl) benzyloxy)phenyl)hex-4-ynoic acid

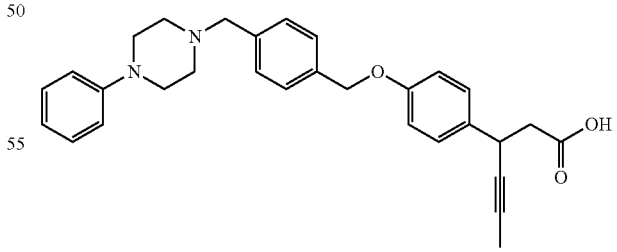

The title compound was obtained by the same method as in Example 12 except that 1-phenylpiperazine was used instead of 1,2,3,4-tetrahydroisoquinoline.

$^1$H NMR (400 MHz, CDCl$_3$): δ 7.37 (2H, d), 7.29 (4H, m), 7.11 (2H, d), 6.93 (5H, m), 4.96 (2H, s), 4.13 (1H, s), 3.66 (2H, m), 3.23 (4H, s), 2.83 (2H, m), 2.66 (2H, s), 1.82 (3H, s).

<Example 16> Preparation of 3-(4-(4-((6-methoxy-3,4-dihydroisoquinolin-2(1H)-yl)methyl)benzyloxy)phenyl)hex-4-ynoic acid

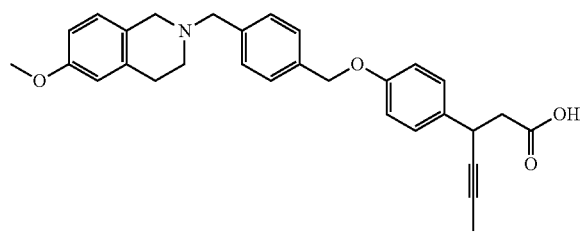 [SMILES: CC#CC(CC(=O)O)c1ccc(OCc2ccc(CN3CCc4cc(OC)ccc4C3)cc2)cc1]

The title compound was obtained by the same method as in Example 12 except that 6-methoxy-1,2,3,4-tetrahydroisoquinoline was used instead of 1,2,3,4-tetrahydroisoquinoline.

$^1$H NMR (400 MHz, CDCl$_3$): δ 7.40 (4H, q), 7.26 (2H, d), 6.92 (3H, q), 6.66 (2H, d), 5.06 (2H, s), 3.94 (1H, s), 3.73 (3H, s), 3.63 (2H, s), 3.35 (3H, s), 2.78 (2H, t), 2.62 (2H, t), 2.58 (2H, s), 1.77 (3H, s)

<Example 17> Preparation of 3-(4-(4-((4-phenylpiperidin-1-yl)methyl)benzyloxy) phenyl)hex-4-ynoic acid

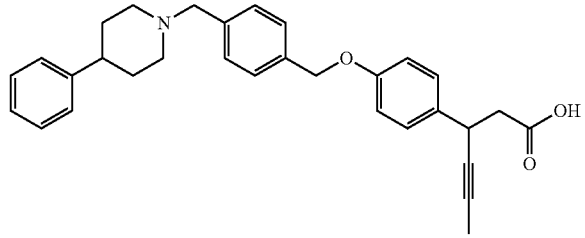 [SMILES: CC#CC(CC(=O)O)c1ccc(OCc2ccc(CN3CCC(c4ccccc4)CC3)cc2)cc1]

The title compound was obtained by the same method as in Example 12 except that 4-phenylpiperidine was used instead of 1,2,3,4-tetrahydroisoquinoline.

$^1$H NMR (400 MHz, CDCl$_3$): δ 7.44 (2H, d), 7.32 (2H, d), 7.23 (5H, t), 7.13 (2H, d), 6.96 (2H, d), 4.92 (2H, s), 4.16 (1H, s), 3.85 (2H, q), 3.33 (2H, t), 2.90 (1H, d), 2.78 (1H, m), 2.58 (1H, t), 2.38 (2H, t), 2.02 (2H, m), 1.83 (5H, m).

<Example 18> Preparation of 3-(4-(4-((4-(4-fluorophenyl)piperazin-1-yl)methyl) benzyloxy)phenyl)hex-4-ynoic acid

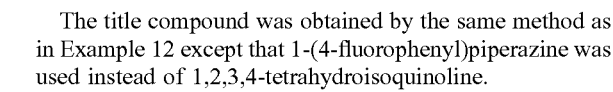

The title compound was obtained by the same method as in Example 12 except that 1-(4-fluorophenyl)piperazine was used instead of 1,2,3,4-tetrahydroisoquinoline.

$^1$H NMR (400 MHz, CDCl$_3$): δ 7.60 (2H, d), 7.46 (2H, d), 7.30 (3H, d), 6.97 (2H, t), 6.86 (4H, m), 5.01 (2H, s), 4.21 (2H, s), 4.04 (1H, t), 3.50 (4H, d), 3.25 (4H, s), 2.78 (2H, m), 1.80 (3H, d).

<Example 19> Preparation of 3-(4-(4-((4-(4-(trifluoromethyl)phenyl)piperazin-1-yl)methyl)benzyloxy)phenyl)hex-4-ynoic acid

The title compound was obtained by the same method as in Example 12 except that 1-(4-(trifluoromethyl)phenyl)piperazine was used instead of 1,2,3,4-tetrahydroisoquinoline.

$^1$H NMR (400 MHz, CDCl$_3$): δ 7.63 (2H, d), 7.51 (4H, d), 7.21 (2H, d), 6.93 (2H, d), 6.74 (2H, s), 5.03 (2H, s), 4.13 (2H, m), 4.01 (1H, t), 3.73 (4H, s), 2.96 (4H, s), 2.71 (2H, m), 1.78 (3H, s).

<Example 20> Preparation of 3-(4-(4-((4-(4-(3-(methylsulfonyl)propoxy)phenyl) piperazin-1-yl)methyl)benzyloxy)phenyl)hex-4-ynoic acid

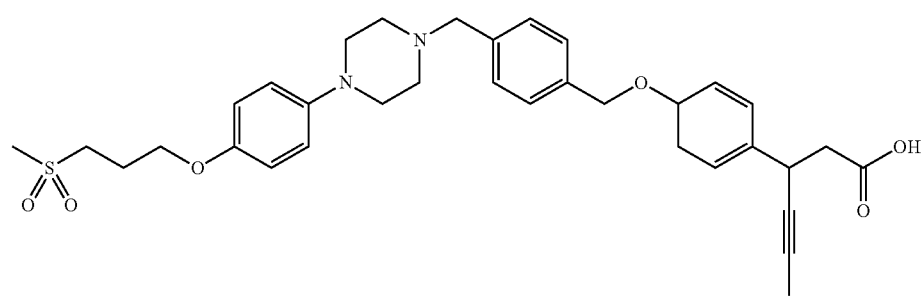 [SMILES: CC#CC(CC(=O)O)C1=CCC(OCc2ccc(CN3CCN(c4ccc(OCCCS(C)(=O)=O)cc4)CC3)cc2)C=C1]

The title compound was obtained by the same method as in Example 12 except that 1-(4-(3-(methylsulfonyl)propoxy)phenyl)piperazine hydrochloride was used instead of 1,2,3,4-tetrahydroisoquinoline.

$^1$H NMR (400 MHz, CDCl$_3$): δ 7.65 (2H, d), 7.49 (2H, d), 7.30 (2H, d), 6.87 (6H, m), 5.07 (2H, s), 4.20 (2H, d), 4.08 (2H, t), 4.01 (1H, t), 6.63 (2H, s), 3.49 (4H, m), 3.26 (2H, t), 3.01 (2H, s), 2.97 (3H, s), 2.71 (2H, m), 2.34 (2H, m), 1.83 (2H, d).

<Example 21> Preparation of (S)-3-(4-(4-((3,4-dihydroisoquinolin-2(1H)-yl)methyl) benzyloxy)phenyl)hex-4-ynoic acid

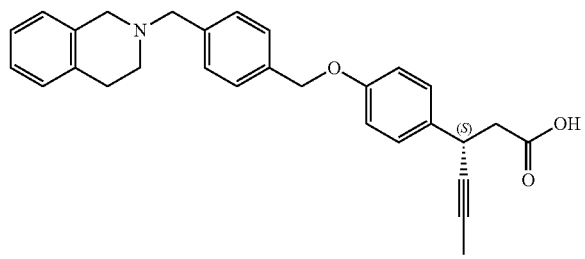

Step 1: Preparation of ethyl (S)-3-(4-(4-((3,4-dihydroisoquinolin-2(1H)-yl)methyl)benzyloxy)phenyl)hex-4-ynoate Under a nitrogen atmosphere, 0.5 g of 1,2,3,4-tetrahydroisoquinoline was added to 20 mL of DMF in a flask and stirred to dissolve, and then 1.1 g of cesium carbonate was added at room temperature. After 30 minutes, 1.0 g of (S)-ethyl 3-(4-(4-((methylsulfonyloxy)methyl)benzyloxy)phenyl)hex-4-ynoate prepared in Preparative Example 7 was added dropwise, followed by stirring at room temperature for 12 hours. Upon completion of the reaction, distilled water was slowly added dropwise, extracted with ethyl acetate, washed with brine, dried over anhydrous magnesium sulfate, and then concentrated. Thereafter, the reaction product was separated by silica column chromatography to give the title compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.14 (2H, m), 4.09 (1H, s), 3.91 (1H, d), 3.70 (3H, m), 2.92 (4H, s), 2.73 (2H, m), 1.83 (3H, s), 1.29 (3H, m).

Step 2: Preparation of (S)-3-(4-(4-((3,4-dihydroisoquinolin-2(1H)-yl)methyl) benzyloxy)phenyl)hex-4-ynoic acid Under a nitrogen atmosphere, 0.5 g of ethyl (S)-3-(4-(4-(3,4-dihydroisoquinolin-2(1H)-yl)methyl)benzyloxy)phenyl)hex-4-ynoate prepared in step 1 was added to THF, methanol, and distilled water in a flask and stirred to dissolve, and then, 0.5 g of lithium hydroxide was slowly added at room temperature, followed by stirring for 1 hour or longer. Upon completion of the reaction, the mixture was acidified with a 1 M hydrochloric acid aqueous solution to a pH of 2-3, extracted with ethyl acetate, and dried under reduced pressure to give the title compound.

$^1$H NMR (400 MHz, CDCl$_3$): δ 7.38 (2H, d), 7.31 (2H, d), 7.22 (2H, d), 7.16 (3H, m), 6.97 (3H, m), 4.98 (2H, s), 4.09 (1H, s), 3.91 (1H, d), 3.70 (3H, m), 2.92 (4H, s), 2.73 (2H, m), 1.83 (3H, s).

<Example 22> Preparation of(S)-3-(4-(4-((4-(4-(trifluoromethyl)phenyl)piperazin-1-yl)methyl)benzyloxy)phenyl)hex-4-ynoic acid

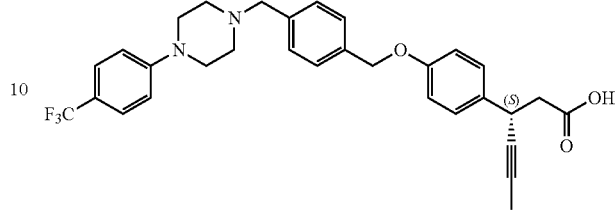

The title compound was obtained by the same method as in Example 21 except that 1-(4-(trifluoromethyl)phenyl)piperazine was used instead of 1,2,3,4-tetrahydroisoquinoline.

$^1$H NMR (400 MHz, CDCl$_3$): δ 7.65 (2H, d), 7.51 (4H, m), 7.30 (2H, d), 6.61 (2H, d), 6.85 (2H, d), 5.05 (2H, s), 4.21 (2H, s), 4.03 (1H, t), 3.68 (4H, s), 3.49 (2H, s), 2.84 (2H, s), 2.70 (2H, m), 1.82 (3H, s).

<Example 23> Preparation of (S)-3-(4-(4-((4-(4-fluorophenyl)piperazin-1-yl)methyl) benzyloxy)phenyl)hex-4-ynoic acid

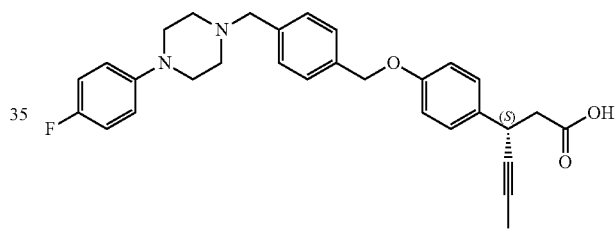

The title compound was obtained by the same method as in Example 21 except that 1-(4-fluorophenyl)piperazine was used instead of 1,2,3,4-tetrahydroisoquinoline.

$^1$H NMR (400 MHz, CDCl$_3$): & 7.39 (2H, d), 7.30 (2H, d), 7.19 (2H, d), 6.96 (4H, m), 6.87 (2H, m), 4.97 (2H, s), 4.10 (2H, s), 3.81 (1H, d), 3.51 (1H, d), 3.15 (4H, s), 2.80 (6H, m), 1.82 (3H, s).

<Example 24> Preparation of potassium (S)-3-(4-(4-((4-(4-(trifluoromethyl)phenyl)piperazin-1-yl)methyl)benzyloxy)phenyl)hex-4-ynoate

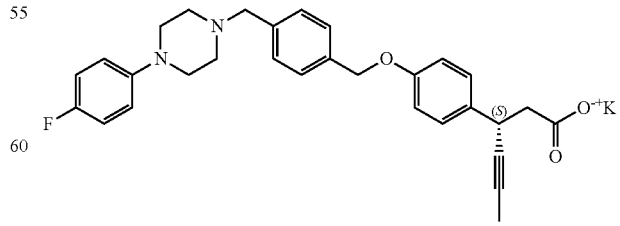

Under a nitrogen atmosphere, 0.4 g of (S)-3-(4-(4-((4-(4-fluorophenyl) piperazin-1-yl)methyl)benzyloxy)phenyl)hex-4-ynoic acid prepared in Example 23 and 10 mL of ethanol were loaded in a flask and stirred to dissolve, and then 0.3 mL of a 3 N potassium hydroxide aqueous solution was added dropwise. Thereafter, the mixture was stirred at room temperature, and upon completion of the reaction, the reaction solution was concentrated under reduced pressure, followed by addition of isopropylalcohol, and the produced solid was filtered to give the target compound.

$^1$H NMR (400 MHz, D$_2$O): δ 7.10 (4H, m), 6.98 (2H, d), 6.57 (4H, d), 6.38 (2H, s), 4.55 (2H, s), 3.82 (1H, s), 3.07 (2H, s), 2.59 (4H, s), 2.36 (2H, s), 2.13 (4H, s), 1.51 (3H, s).

<Example 25> Preparation of (S)-3-(4-(4-((6-methoxy-3,4-dihydroisoquinolin-2(1H)-yl)methyl)benzyloxy)phenyl)hex-4-ynoic acid

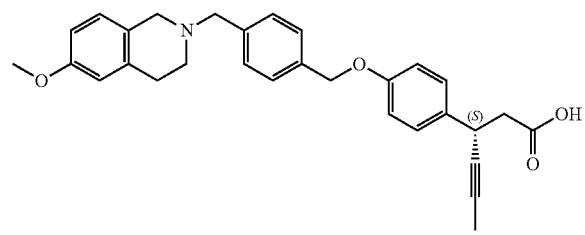

The title compound was obtained by the same method as in Example 21 except that 6-methoxy-1,2,3,4-tetrahydroisoquinoline was used instead of 1,2,3,4-tetrahydroisoquinoline.

$^1$H NMR (400 MHz, DMSO): δ 7.40 (4H, q), 7.26 (2H, d), 6.94 (3H, m), 6.68 (2H, m), 5.06 (2H, s), 3.95 (1H, t), 3.70 (3H, s), 3.51 (2H, s), 3.43 (2H, s), 2.77 (2H, t), 2.66 (2H, t), 2.57 (2H, d), 1.75 (3H, d).

<Example 26> Preparation of (S)-3-(4-(4-((4-phenylpiperidin-1-yl)methyl) benzyloxy)phenyl)hex-4-ynoic acid

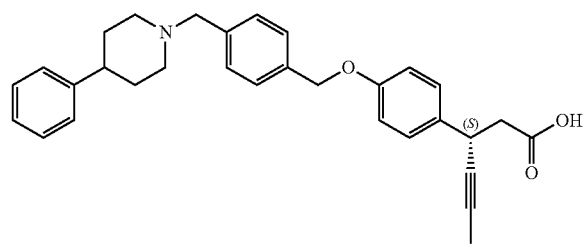

The title compound was obtained by the same method as in Example 21 except that 4-phenylpiperidine was used instead of 1,2,3,4-tetrahydroisoquinoline.

$^1$H NMR (400 MHz, CDCl$_3$): δ 7.66 (2H, d), 7.49 (2H, d), 7.30 (7H, m), 6.87 (2H, d), 5.04 (2H, s), 4.19 (2H, s), 4.06 (1H, t), 3.59 (2H, d), 2.73 (7H, m), 2.00 (2H, d), 1.82 (3H, s).

<Example 27> Preparation of (S)-3-(4-(4-(isoindolin-2-ylmethyl)benzyloxy) phenyl)hex-4-ynoic acid

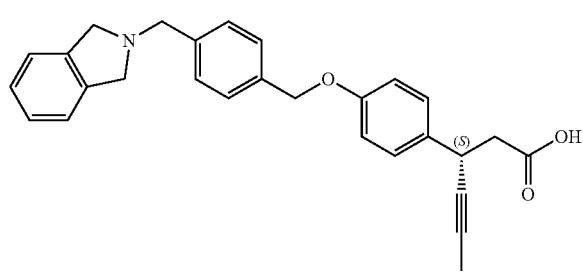

The title compound was obtained by the same method as in Example 21 except that isoindoline was used instead of 1,2,3,4-tetrahydroisoquinoline.

$^1$H NMR (400 MHz, CDCl$_3$): δ 7.68 (2H, d), 7.47 (2H, d), 7.38 (2H, m), 7.30 (4H, m), 6.87 (2H, d), 5.06 (2H, s), 4.90 (2H, s), 4.32 (4H, m), 4.05 (1H, t), 2.81 (2H, m), 1.83 (3H, s).

<Example 28> Preparation of (S)-3-(4-(4-((4-phenyl-5,6-dihydropyridin-1(2H)-yl)methyl)benzyloxy) phenyl)hex-4-ynoic acid

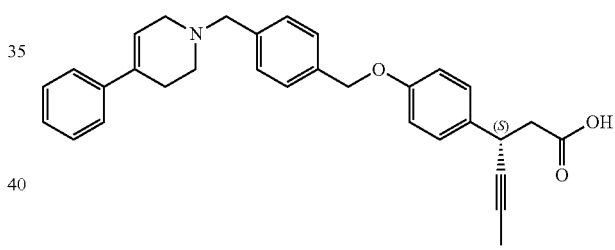

The title compound was obtained by the same method as in Example 21 except that 4-phenyl-1,2,3,6-tetrahydropyridine hydrochloride was used instead of 1,2,3,4-tetrahydroisoquinoline.

$^1$H NMR (400 MHz, CDCl$_3$): δ 7.47 (2H, d), 7.36 (9H, m), 6.88 (2H, d), 5.99 (1H, s), 4.99 (2H, s), 4.18 (1H, m), 4.06 (2H, m), 3.53 (2H, s), 3.22 (2H, s), 2.82 (4H, m), 1.82 (3H, s).

<Example 29> Preparation of (S)-3-(4-(4-((4-(4-(methoxymethoxy)phenyl)piperazin-1-yl)methyl)benzyloxy)phenyl)hex-4-ynoic acid

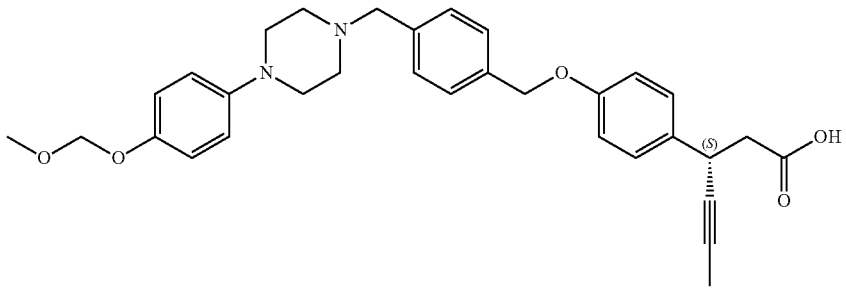

The title compound was obtained by the same method as in Example 21 except that 1-(4-(methoxymethoxy)phenyl)piperazine was used instead of 1,2,3,4-tetrahydroisoquinoline.

$^1$H NMR (400 MHz, CDCl$_3$): δ 7.57 (2H, d), 7.46 (2H, d), 7.26 (2H, d), 6.97 (2H, d), 6.87 (2H, d), 6.80 (2H, d), 5.13 (2H, s), 5.01 (2H, s), 4.13 (2H, s), 4.02 (1H, t), 3.51 (11H, m), 2.72 (2H, m), 1.79 (3H, s).

<Example 30> Preparation of (S)-3-(4-(4-((4-(5-isopropyl-1,2,4-oxadiazol-3-yl)piperidin-1-yl)methyl)benzyloxy)phenyl)hex-4-ynoic acid

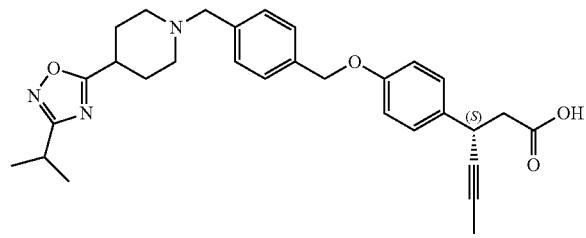

The title compound was obtained by the same method as in Example 21 except that 3-isopropyl-5-(piperidin-4-yl)-1,2,4-oxadiazole was used instead of 1,2,3,4-tetrahydroisoquinoline.

$^1$H NMR (400 MHz, CDCl$_3$): δ 7.63 (2H, d), 7.46 (2H, d), 7.30 (2H, d), 6.86 (2H, d), 5.05 (2H, d), 4.13 (2H, m), 4.03 (1H, t), 3.61 (1H, s), 3.43 (2H, s), 3.10 (1H, m), 2.92 (4H, m), 2.73 (2H, m), 2.30 (2H, m), 1.83 (3H, s), 1.32 (6H, d).

<Example 31> Preparation of (S)-3-(4-(4-((4-(5-isopropyl-1,2,4-oxadiazol-3-yl)piperazin-1-yl)methyl)benzyloxy)phenyl)hex-4-ynoic acid

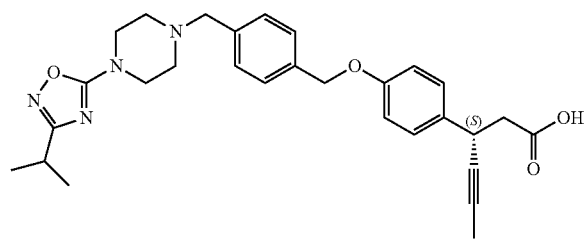

The title compound was obtained by the same method as in Example 21 except that 3-isopropyl-5-(piperazin-1-yl)-1,2,4-oxadiazole was used instead of 1,2,3,4-tetrahydroisoquinoline.

$^1$H NMR (400 MHz, CDCl$_3$): δ 7.61 (2H, d), 7.49 (2H, d), 7.30 (2H, d), 6.87 (2H, d), 5.05 (2H, s), 4.15 (4H, m), 4.02 (1H, t), 3.49 (3H, m), 2.81 (3H, m), 1.83 (3H, s), 1.24 (6H, d).

<Example 32> Preparation of (S)-3-(4-(4-((4-(4-(methylsulfonyl)phenyl)-5,6-dihydropyridin-1(2H)-yl)methyl)benzyloxy)phenyl)hex-4-ynoic acid

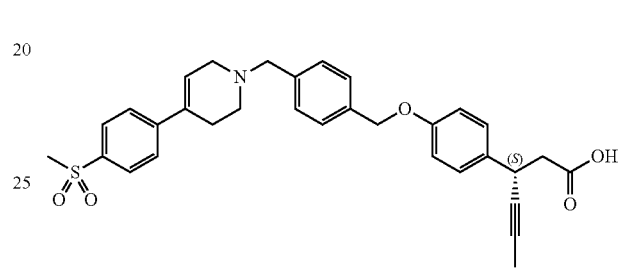

The title compound was obtained by the same method as in Example 21 except that 4-(4-(methylsulfonyl)phenyl)-1,2,3,6-tetrahydropyridine hydrochloride prepared in Preparative Example 9 was used instead of 1,2,3,4-tetrahydroisoquinoline.

$^1$H NMR (400 MHz, DMSO): δ 7.95 (2H, d), 7.75 (2H, d), 7.63 (2H, d), 7.44 (2H, d), 7.30 (2H, d), 6.98 (2H, d), 6.37 (1H, s), 5.14 (2H, s), 4.45 (2H, t), 6.97 (1H, s), 6.82 (4H, m), 3.27 (4H, s), 2.84 (2H, s), 2.59 (2H, d), 1.77 (3H, s).

<Example 32> Preparation of (S)-3-(4-(4-((4-(4-(3-(methylsulfonyl)propoxy)phenyl)-5,6-dihydropyridin-1(2H)-yl)methyl)benzyloxy)phenyl)hex-4-ynoic acid

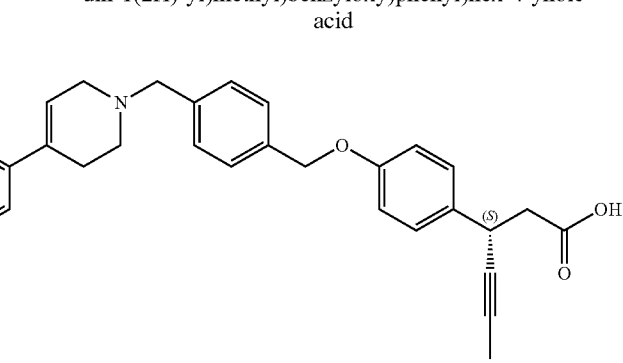

The title compound was obtained by the same method as in Example 21 except that 4-(4-(3-(methylsulfonyl)propoxy)phenyl)-1,2,3,6-tetrahydropyridine hydrochloride prepared in Preparative Example 11 was used instead of 1,2,3,4-tetrahydroisoquinoline.

¹H NMR (400 MHz, CDCl₃): δ 7.66 (2H, d), 7.49 (2H, d), 7.32 (2H, d), 7.15 (2H, d), 6.90 (2H, d), 6.82 (2H, d), 5.06 (2H, s), 4.18 (2H, s), 4.09 (3H, m), 3.58 (2H, s), 3.26 (2H, m), 2.97 (3H, s), 2.81 (5H, m), 2.62 (3H, s), 2.32 (2H, m), 1.96 (2H, d), 1.83 (3H, s).

<Example 34> Preparation of (3S)-3-(4-(4-(1-(3,4-dihydroisoquinolin-2(1H)-yl)ethyl)benzyloxy)phenyl)hex-4-ynoic acid

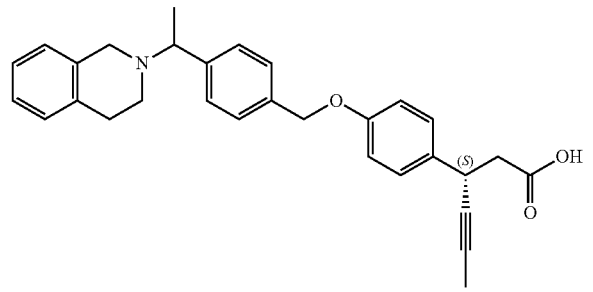

The title compound was obtained by the same method as in Example 21 except that (3S)-ethyl 3-(4-(4-(1-bromoethyl)benzyloxy)phenyl)hex-4-ynoate prepared in Preparative Example 12 was used instead of (S)-ethyl 3-(4-(4-((methylsulfonyloxy)methyl)benzyloxy)phenyl)hex-4-ynomate.

¹H NMR (400 MHz, CDCl₃): δ 12.98 (1H, s), 7.61 (6H, m), 7.30 (4H, m), 6.92 (2H, t), 5.08 (2H, s), 4.29 (2H, s), 4.06 (1H, s), 3.81 (1H, s), 3.51 (2H, s), 3.21 (2H, m), 2.75 (2H, m), 1.95 (2H, d), 1.84 (3H, s).

<Example 35> Preparation of (S)-3-(4-(4-((4-(4-hydroxyphenyl)piperazin-1-yl)methyl)benzyloxy)phenyl)hex-4-ynoic acid

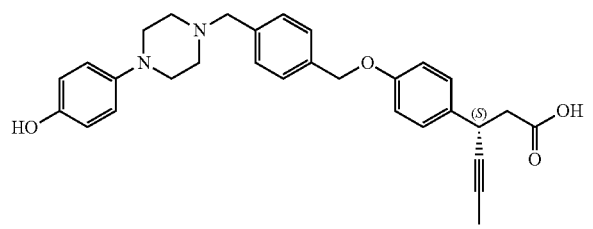

The title compound was obtained by the same method as in Example 21 except that 4-(1,2,3,6-tetrahydropyridin-4-yl)phenol hydrochloride prepared in Preparative Example 10 was used instead of 1,2,3,4-tetrahydroisoquinoline.

¹H NMR (400 MHz, CDCl₃): δ 8.80 (1H, s), 7.41 (2H, d), 735 (2H, d), 7.28 (2H, d), 6.94 (2H, d), 6.74 (2H, d), 6.63 (2H, d), 5.06 (2H, s), 3.94 (1H, t), 3.62 (3H, s), 2.95 (4H, s), 2.61 (2H, d), 1.77 (3H, s).

<Example 36> Preparation of (S)-3-(4-(4-((4-(4-(3-(methylsulfonyl)propoxy) phenyl)piperazin-1-yl)methyl)benzyloxy)phenyl)hex-4-ynoic acid

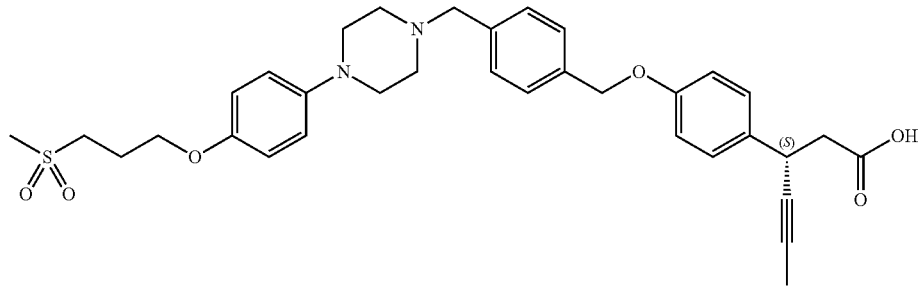

The title compound was obtained by the same method as in Example 21 except that 1-(4-(3-(methylsulfonyl)propoxy)phenyl)piperazine hydrochloride was used instead of 1,2,3,4-tetrahydroisoquinoline.

¹H NMR (400 MHz, CDCl₃): δ 12.32 (1H, s), 7.42 (4H, m), 7.29 (2H, d), 6.96 (2H, d), 6.83 (4H, q), 5.06 (2H, s), 4.02 (2H, t), 3.92 (1H, t), 3.52 (2H, s), 3.25 (2H, t), 3.01 (7H, m), 2.61 (2H, d), 2.09 (2H, m), 1.77 (3H, d).

<Example 37> Preparation of sodium (S)-3-(4-(4-(isoindolin-2-ylmethyl) benzyloxy)phenyl)hex-4-ynoate

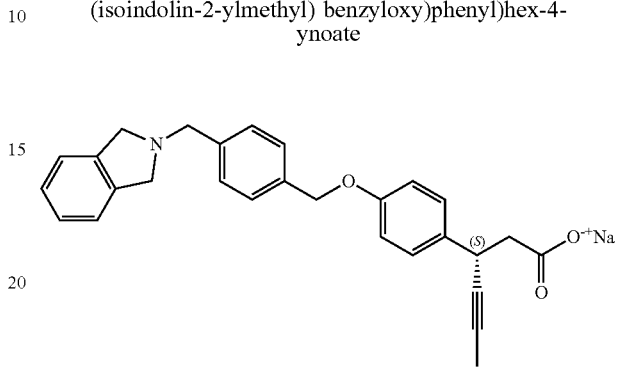

Under a nitrogen atmosphere, 0.4 g of (S)-3-(4-(4-(isoindolin-2-ylmethyl)benzyloxy)phenyl)hex-4-ynoic acid prepared in Example 27 and ethanol were loaded in a 500-mL flask and stirred to dissolve, and then 0.3 mL of a 3 N sodium hydroxide aqueous solution was added dropwise. Thereafter, the mixture was stirred at room temperature, and upon completion of the reaction, the reaction solution was concentrated under reduced pressure, followed by addition of isopropylalcohol, and the produced solid was filtered to give the target compound.

¹H NMR (400 MHz, CDCl₃): δ 7.09 (2H, d), 7.03 (2H, d), 6.97 (2H, d), 6.85 (2H, m), 6.75 (2H, m), 6.57 (2H, d), 4.54 (2H, s), 3.81 (1H, t), 3.36 (4H, s), 3.31 (2H, s), 2.33 (2H, d), 1.54 (3H, d).

<Example 38> Preparation of L-lysine (S)-3-(4-(4-(isoindolin-2-ylmethyl) benzyloxy)phenyl)hex-4-ynoate

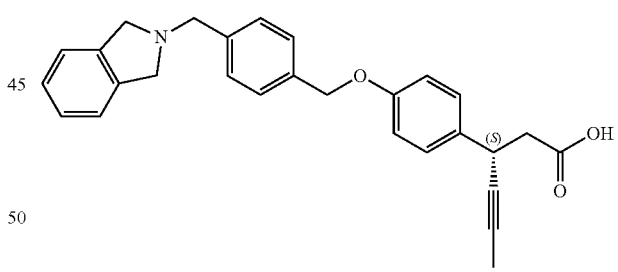

+

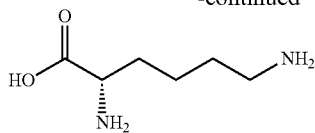

Under a nitrogen atmosphere, 0.4 g of (S)-3-(4-(4-(isoindolin-2-ylmethyl)benzyloxy)phenyl)hex-4-ynoic acid prepared in Example 27 and ethanol were loaded in a flask and stirred to dissolve, and then 0.12 g of L-lysine was added. Thereafter, the reaction temperature was raised to 50° C., and the mixture was stirred for 30 minutes at 50° C., and again cooled to room temperature, followed by stirring for 30 minutes. Upon completion of the reaction, the produced solid was filtered to give the title compound.

$^1$H NMR (400 MHz, D$_2$O): δ 7.03 (6H, s), 6.83 (2H, s), 6.74 (2H, s), 6.54 (2H, s), 4.53 (2H, s), 3.77 (1H, s), 3.54 (5H, m), 2.88 (2H, t), 2.28 (2H, s), 1.74 (2H, m), 1.62 (3H, m), 1.42 (3H, s), 1.35 (3H, m).

<Example 39> Preparation of (S)-3-(4-(4-((4-(4-fluorophenyl)-5,6-dihydropyridine-1(2H)-yl)methyl)benzyloxy)phenyl)hex-4-ynoic acid

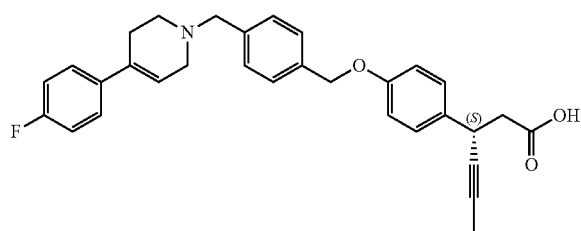

The title compound was obtained by the same method as in Example 21 except that 4-(4-fluorophenyl)-1,2,3,6-tetrahydropyridine hydrochloride was used instead of 1,2,3,4-tetrahydroisoquinoline.

$^1$H NMR (400 MHz, CDCl$_3$): δ 7.69 (2H, d), 7.48 (2H, d), 7.32 (4H, m), 7.04 (2H, t), 6.86 (2H, d), 5.90 (1H, s), 5.03 (2H, s), 4.30 (2H, s), 4.02 (1H, t), 3.71 (2H, s), 3.54 (2H, s), 3.31 (2H, s), 2.73 (2H, m), 1.81 (3H, d).

<Example 40> Preparation of (S)-3-(4-(4-((4-(4-methoxyphenyl)piperazin-1-yl)methyl)benzyloxy)phenyl)hex-4-ynoic acid

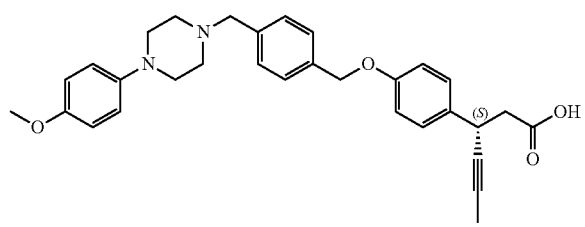

The title compound was obtained by the same method as in Example 21 except that 4-(4-methoxyphenyl)-1,2,3,6-tetrahydropyridine was used instead of 1,2,3,4-tetrahydroisoquinoline.

$^1$H NMR (400 MHz, CDCl$_3$): δ 7.64 (2H, d), 7.48 (2H, d), 7.31 (2H, d), 6.94 (2H, s), 6.86 (4H, t), 5.04 (2H, s), 4.21 (2H, s), 4.03 (1H, t), 3.78 (3H, s), 3.60 (2H, s), 3.47 (2H, s), 3.05 (2H, s), 2.73 (2H, m), 1.82 (3H, s).

<Example 41> Preparation of sodium (S)-3-(4-(4-((3,4-dihydroquinolin-1(2H)-yl)methyl)benzyloxy)phenyl)hex-4-ynoate

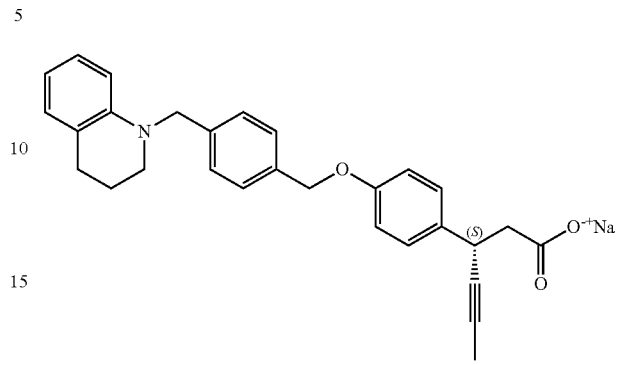

Step 1: Preparation of (S)-3-(4-(4-((3,4-dihydroisoquinolin-1(1H)-yl)methyl)benzyloxy)phenyl)hex-4-ynoic acid The title compound was obtained by the same method as in Example 21 except that 1,2,3,4-tetrahydroquinoline was used instead of 1,2,3,4-tetrahydroisoquinoline.

$^1$H NMR (400 MHz, CDCl$_3$): δ 7.02 (2H, d), 6.76 (2H, d), 6.69 (2H, d), 6.43 (4H, m), 6.21 (1H, s), 6.02 (1H, s), 4.24 (2H, s), 3.84 (3H, s), 2.68 (2H, s), 2.37 (2H, d), 2.14 (2H, s), 1.47 (3H, s), 1.35 (2H, s).

Step 2: Preparation of sodium (S)-3-(4-(4-((3,4-dihydroquinolin-1(1H)-yl)methyl)benzyloxy)phenyl)hex-4-ynoate The title compound was obtained by the same method as in Example 37 except that (S)-3-(4-(4-((3,4-dihydroquinolin-1(2H)-yl)methyl)benzyloxy)phenyl)hex-4-ynoic acid prepared in step 1 was used instead of (S)-3-(4-(4-(isoindolin-2-yl methyl)benzyloxy)phenyl)hex-4-ynoic acid.

$^1$H NMR (400 MHz, D$_2$O): δ 7.01 (2H, d), 6.74 (2H, d), 6.68 (2H, d), 6.42 (4H, m), 6.15 (1H, s), 6.02 (1H, s), 4.25 (2H, s), 3.79 (3H, s), 2.62 (2H, s), 2.34 (2H, d), 2.12 (2H, s), 1.45 (3H, s), 1.32 (2H, s).

<Example 42> Preparation of potassium (S)-3-(4-(4-((3,4-dihydroquinolin-1(2H)-yl)methyl)benzyloxy)phenyl)hex-4-ynoate

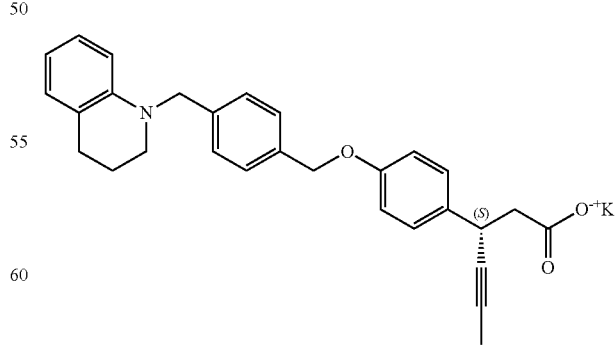

The title compound was obtained by the same method as in Example 25 except that (S)-3-(4-(4-((3,4-dihydroquinolin-1(2H)-yl)methyl)benzyloxy)phenyl)hex-4-ynoic acid prepared in step 1 in Example 41 was used instead of (S)-3-(4-(4-((4-(4-fluorophenyl)piperazin-1-yl)methyl)benzyloxy)phenyl)hex-4-ynoic acid ¹H NMR (400 MHz, D₂O): δ 6.97 (2H, d), 6.71 (2H, d), 6.63 (2H, d), 6.45 (2H, s), 6.38 (2H, d), 6.13 (1H, s), 5.98 (1H, s), 4.20 (2H, s), 3.71 (3H, m), 2.58 (2H, s), 2.32 (2H, s), 2.15 (2H, s), 1.43 (3H, s), 1.29 (2H, s).

<Example 43> Preparation of (S)-3-(4-(4-((4-(benzo[d]thiazol-2-yl)piperazin-1-yl)methyl)benzyloxy)phenyl)hex-4-ynoic acid

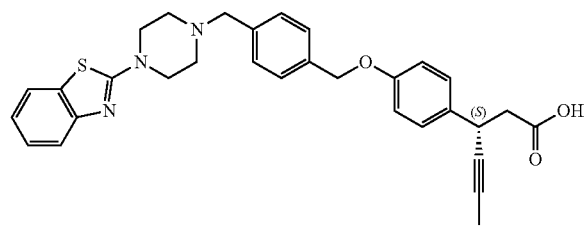

The title compound was obtained by the same method as in Example 21 except that 2-(piperazin-1-yl)benzo[d]thiazole hydrochloride prepared in Preparative Example 13 was used instead of 1,2,3,4-tetrahydroisoquinoline.

¹H NMR (400 MHz, DMSO): δ 10.87 (1H, s), 7.85 (1H, d), 7.55 (5H, m), 7.31 (3H, m), 7.14 (2H, t), 6.96 (2H, d), 5.13 (2H, s), 4.40 (2H, s), 4.17 (2H, d), 3.95 (1H, t), 3.57 (3H, t), 3.22 (3H, s), 2.57 (2H, d), 1.78 (3H, d).

<Example 44> Preparation of (S)-3-(4-(4-((4-(5-propylpyrimidin-2-yl) piperazin-1-yl)methyl)benzyloxy)phenyl)hex-4-ynoic acid TN OOH

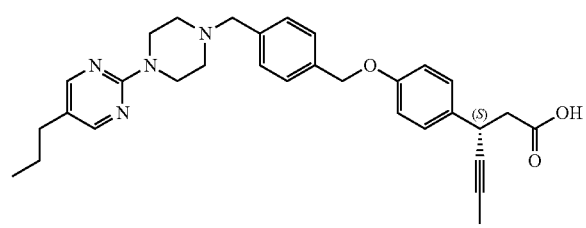

The title compound was obtained by the same method as in Example 21 except that 2-(piperazin-1-yl)-5-propylpyrimidine hydrochloride prepared in Preparative Example 14 was used instead of 1,2,3,4-tetrahydroisoquinoline.

¹H NMR (400 MHz, CDCl₃): δ 8.20 (2H, s), 7.62 (2H, d), 7.47 (2H, d), 7.30 (2H, d), 6.85 (2H, d), 5.08 (2H, s), 4.80 (2H, d), 4.17 (2H, s), 4.03 (1H, t), 3.84 (1H, t), 3.43 (2H, s), 2.74 (4H, m), 2.43 (2H, t), 1.83 (3H, d), 1.59 (2H, q), 0.94 (3H, t).

<Example 45> Preparation of (S)-3-(4-(4-((4-(5-cyanopyridin-2-yl)piperazin-1-yl)methyl)benzyloxy)phenyl)hex-4-ynoic acid

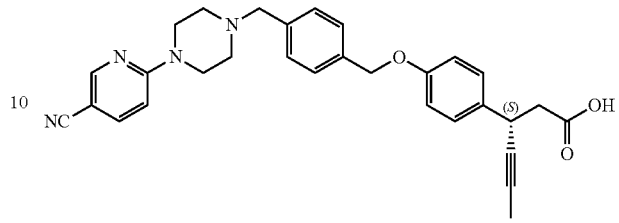

The title compound was obtained by the same method as in Example 21 except that 6-(piperazin-1-yl)nicotinonitrile hydrochloride prepared in Preparative Example 15 was used instead of 1,2,3,4-tetrahydroisoquinoline.

¹H NMR (400 MHz, DMSO): δ 11.20 (1H, s), 8.56 (1H, s), 7.99 (1H, d), 7.63 (1H, d), 7.55 (1H, d), 7.27 (2H, d), 7.04 (1H, d), 6.95 (2H, d), 5.12 (2H, s), 4.57 (2H, d), 4.35 (2H, s), 3.95 (1H, t), 3.39 (5H, m), 2.90 (2H, m), 2.59 (2H, d), 1.77 (3H, d).

<Example 46> Preparation of (3S)-3-(4-(4-((3-phenylpyrrolidin-1-yl)methyl)benzyloxy)phenyl)hex-4-ynoic acid

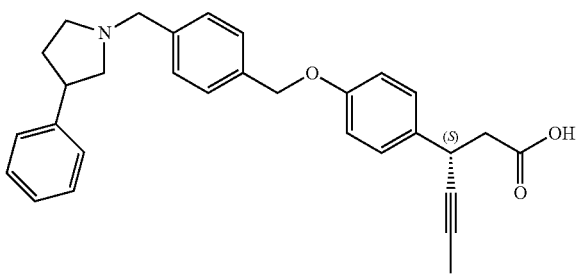

The title compound was obtained by the same method as in Example 21 except that 3-phenylpyrrolidine was used instead of 1,2,3,4-tetrahydroisoquinoline.

¹H NMR (400 MHz, CDCl₃): δ 12.64 (1H, s), 7.66 (2H, s), 7.46 (2H, d), 7.32 (7H, m), 6.86 (2H, d), 5.02 (2H, s), 4.28 (2H, m), 4.04 (1H, t), 3.87 (2H, s), 3.73 (1H, s), 3.18 (1H, s), 2.89 (1H, m), 2.84 (3H, m), 2.61 (1H, s), 2.41 (1H, s), 2.19 (1H, s), 1.81 (3H, d).

<Example 47> Preparation of sodium (S)-3-(4-(3-(4-(4-methoxyphenyl) piperazin-1-yl)benzyloxy)phenyl)hex-4-ynoate

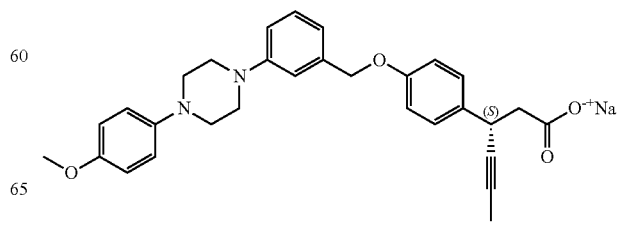

The title compound was obtained by the same method as in Example 37 except that (S)-3-(4-(4-((4-(4-methoxyphenyl)piperazin-1-yl)methyl)benzyloxy) phenyl)hex-4-ynoic acid prepared in Example 40 was used instead of (S)-3-(4-(4-(isoindolin-2-ylmethyl)benzyloxy)phenyl)hex-4-ynoic acid.

$^1$H NMR (400 MHz, MEOC): δ 7.33 (2H, d), 7.26 (1H, d), 7.11 (1H, s), 6.96 (8H, m), 5.04 (2H, s), 4.04 (1H, t), 3.76 (3H, s), 3.32 (4H, m), 3.21 (4H, m), 2.52 (2H, m), 1.80 (3H, s).

<Example 48> Preparation of (S)-3-(4-(4-(2-(6-methoxy-3,4-dihydroisoquinolin-2(1H)-yl)ethyl)benzyloxy)phenyl)hex-4-ynoic acid

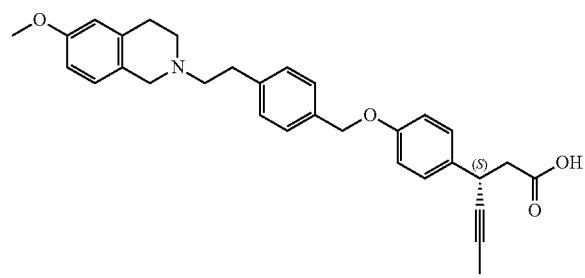

Step 1: Preparation of ethyl (S)-3-(4-(4-(2-(6-methoxy-3,4-dihydroisoquinolin-2(1H)-yl)ethyl)benzyloxy)phenyl)hex-4-ynoate Under a nitrogen atmosphere, 0.5 g of 6-methoxy-1,2,3,4-tetrahydroisoquinoline was added to 20 mL of DMF in a flask and stirred to dissolve, and then 1.1 g of cesium carbonate was added at room temperature. After 30 minutes, 1.0 g of (S)-ethyl 3-(4-(4-(2-(methylsulfonyloxy)ethyl)benzyloxy)phenyl)hex-4-ynoate prepared in Preparative Example 16 was added dropwise, followed by stirring at room temperature for 12 hours. Upon completion of the reaction, distilled water was slowly added dropwise, extracted with ethyl acetate, washed with brine, dried over anhydrous magnesium sulfate, and then concentrated. Thereafter, the reaction product was separated by silica column chromatography to give the title compound.

$^1$H NMR (400 MHz, CDCl$_3$): δ 7.35 (2H, d), 7.30 (2H, d), 7.23 (2H, d), 7.00 (1H, d), 6.85 (2H, d), 6.80 (1H, d), 6.70 (1H, d), 5.00 (2H, s), 4.30 (2H, m), 4.13 (2H, m) 4.03 (1H, t), 3.80 (3H, s), 3.58 (6H, m), 3.30 (2H, s), 2.78 (2H, m), 1.86 (3H, d), 1.28 (3H, m).

Step 2: Preparation of (S)-3-(4-(4-(2-(6-methoxy-3,4-dihydroisoquinolin-2(1H)-yl)ethyl)benzyloxy)phenyl)hex-4-ynoic acid Under a nitrogen atmosphere, 0.5 g of ethyl (S)-3-(4-(4-(2-(6-methoxy-3,4-dihydroisoquinolin-2(1H)-yl)ethyl)benzyloxy)phenyl)hex-4-ynoate prepared in step 1 was added to THF, methanol, and distilled water in a flask and stirred to dissolve, and then, 0.5 g of lithium hydroxide was slowly added at room temperature, followed by stirring for 1 hour or longer. Upon completion of the reaction, the mixture was acidified with a 1 M hydrochloric acid aqueous solution to a pH of 2-3, extracted with ethyl acetate, and dried under reduced pressure to give the title compound.

$^1$H NMR (400 MHz, CDCl$_3$): δ 7.35 (2H, d), 7.30 (2H, d), 7.23 (2H, d), 7.00 (1H, d), 6.85 (2H, d), 6.80 (1H, d), 6.70 (1H, d), 5.00 (2H, s), 4.30 (2H, m), 4.03 (1H, t), 3.80 (3H, s), 3.58 (6H, m), 3.30 (2H, s), 2.78 (2H, m), 1.86 (3H, d).

<Example 49> Preparation of (S)-3-(4-(4-(2-(isoindolin-2-yl)ethyl) benzyloxy)phenyl)hex-4-ynoic acid

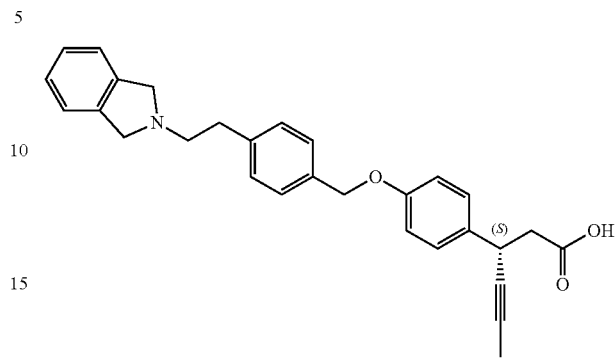

The title compound was obtained by the same method as in Example 48 except that isoindoline was used instead of 6-methoxy-1,2,3,4-tetrahydroisoquinoline.

$^1$H NMR (400 MHz, CDCl$_3$): δ 13.57 (1H, s), 7.38 (3H, m), 7.29 (7H, m), 6.90 (2H, d), 5.03 (4H, m), 4.28 (2H, s), 4.08 (1H, t), 3.48 (2H, m), 3.34 (2H, m), 2.80 (2H, m), 1.83 (3H, d).

<Example 50> Preparation of (S)-3-(4-(4-(2-(3,4-dihydroisoquinolin-2(1H)-yl)ethyl)benzyloxy)phenyl)hex-4-ynoic acid

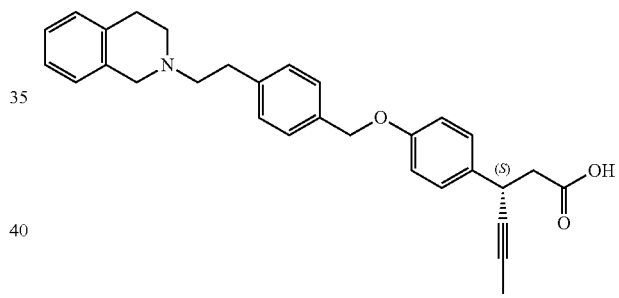

The title compound was obtained by the same method as in Example 48 except that 1,2,3,4-tetrahydroisoquinoline was used instead of 6-methoxy-1,2,3,4-tetrahydroisoquinoline.

$^1$H NMR (400 MHz, DMSO): δ 7.44 (2H, d), 7.38 (2H, d), 7.27 (5H, m), 7.22 (1H, d), 6.94 (2H, d), 5.07 (2H, s), 4.64 (1H, d), 4.38 (1H, s), 3.95 (1H, t), 3.77 (1H, s), 3.39 (2H, s), 3.16 (4H, m), 2.26 (2H, d), 1.77 (3H, d), 1.84 (3H, d), 1.29 (3H, t).

<Example 51> Preparation of sodium (S)-3-(4-(4-((6-methoxy-3,4-dihydroisoquinolin-2(1H)-yl)methyl)benzyloxy)phenyl)hex-4-ynoate

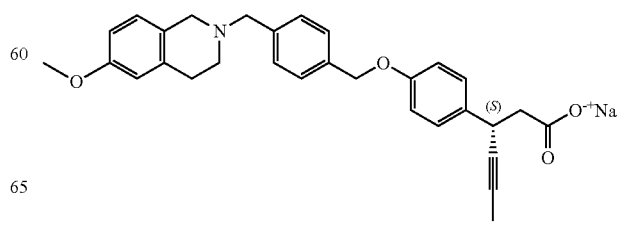

The title compound was obtained by the same method as in Example 37 except that (S)-3-(4-(4-((6-methoxy-3,4-dihydroisoquinolin-2(1H)-yl)methyl)benzyloxy) phenyl)hex-4-ynoic acid prepared in Example 25 was used instead of (S)-3-(4-(4-(isoindolin-2-ylmethyl)benzyloxy)phenyl)hex-4-ynoic acid.

$^1$H NMR (400 MHz, D$_{32}$O): δ 7.10 (2H, d), 7.02 (2H, d), 6.95 (2H, d), 6.55 (2H, d), 6.40 (1H, d), 6.34 (2H, s), 4.53 (2H, s), 3.83 (1H, t), 3.39 (3H, s), 3.17 (2H, s), 3.05 (2H, s), 2.37 (4H, m), 2.20 (2H, s), 1.57 (3H, s).

<Comparative Example 1> Preparation of [(3S)-6-({(2',6'-dimethyl-4'-[3-(methanesulfonyl)propoxy]-[1,1'-biphenyl]-3-yl)}methoxy)-2,3-dihydro-1-benzofuran-3-yl]acetic Acid

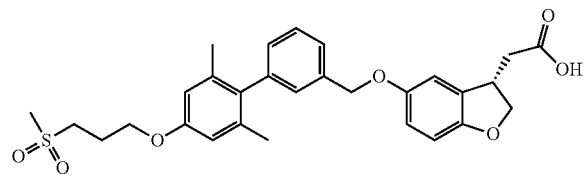 [SMILES: Cc1cc(OCCCS(C)(=O)=O)cc(C)c1-c1cccc(COc2ccc3c(c2)[C@H](CC(=O)O)CO3)c1]

[(3S)-6-({(2',6'-dimethyl-4'-[3-(methanesulfonyl)propoxy]-[1,1'-biphenyl]-3-yl)}methoxy)-2,3-dihydro-1-benzofuran-3-yl]acetic acid was prepared by a method known in WO 2008/001931.

<Comparative Example 2> Preparation of (3S)-3-(4-{[4-(1'H-spiro[indene-1,4'-piperidin]-1'-ylmethyl)benzyl]oxy}phenyl)hex-4-ylnoic acid

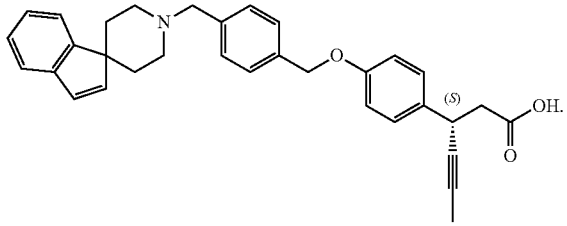

(3S)-3-(4-{[4-(1'H-spiro[indene-1,4'-piperidin]-1'-ylmethyl)benzyl]oxy}phenyl)hex-4-ylnoic acid was prepared by a method known in WO 2011/046851.

<Comparative Example 3> Preparation of 4-(3-phenoxybenzylamino) phenylpropynoic acid

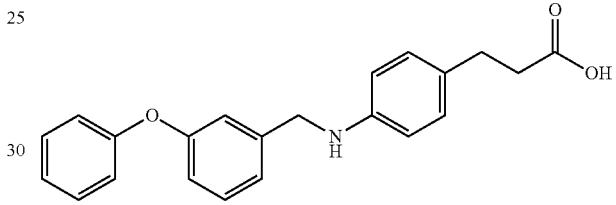

4-(3-phenoxybenzylamino)phenylpropynoic acid was prepared by a known method.

Table 1 summarizes the chemical structures of the compounds prepared in Examples 1-51.

TABLE 1

| Example | Formula |
| --- | --- |
| 1 | 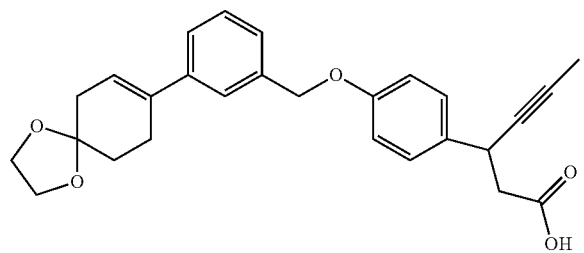 [SMILES: CC#CC(CC(=O)O)c1ccc(OCc2cccc(C3=CCC4(CC3)OCCO4)c2)cc1] |
| 2 | 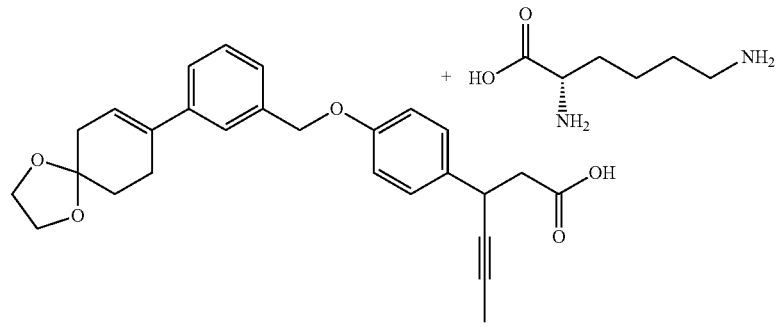 [SMILES: CC#CC(CC(=O)O)c1ccc(OCc2cccc(C3=CCC4(CC3)OCCO4)c2)cc1 ; NCCCC[C@H](N)C(=O)O] |

TABLE 1-continued

| Example | Formula |
|---------|---------|
| 3 | |
| 4 | |
| 5 | |
| 6 | |
| 7 | |

TABLE 1-continued
| Example | Formula |
|---|---|
| 8 | 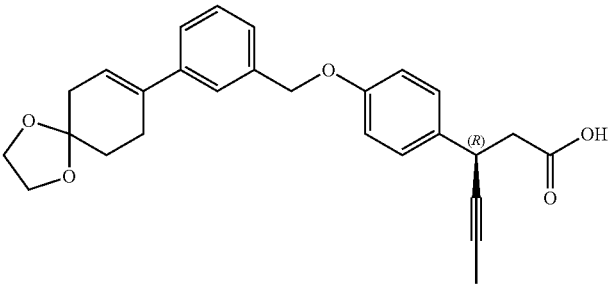 |
| 9 | 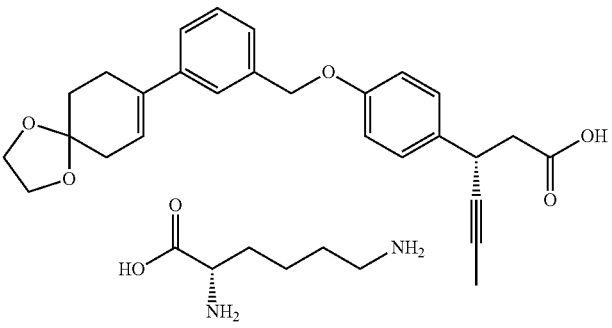 [SMILES: CC#C[C@@H](CC(=O)O)c1ccc(OCc2cccc(C3=CCC4(CC3)OCCO4)c2)cc1 ; NCCCC[C@H](N)C(=O)O] |
| 10 | 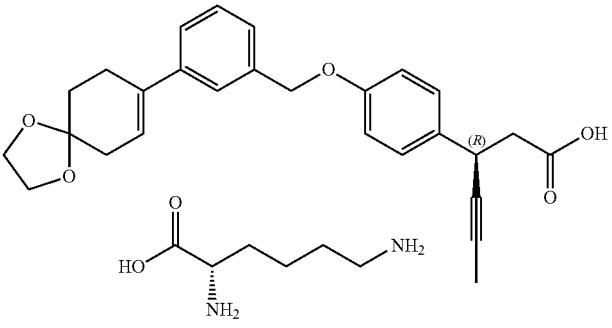 |
| 11 | 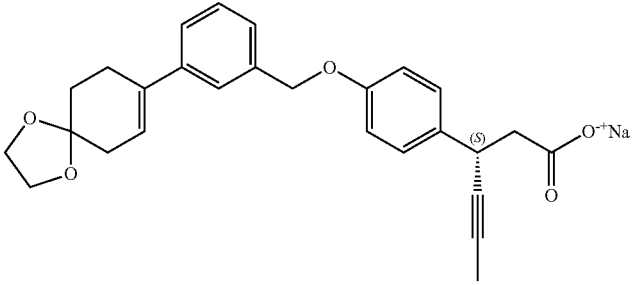 |
| 12 | 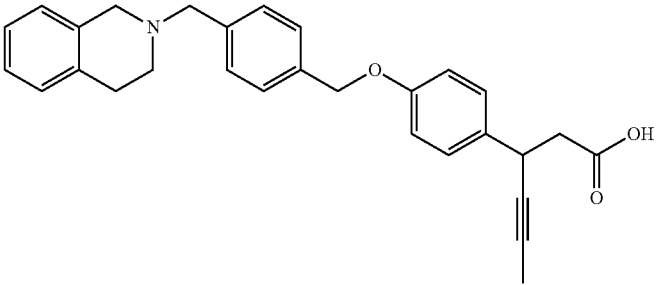 [SMILES: CC#CC(CC(=O)O)c1ccc(OCc2ccc(CN3CCc4ccccc4C3)cc2)cc1] |

TABLE 1-continued

| Example | Formula |
| --- | --- |
| 13 | |
| 14 | |
| 15 | |
| 16 | |
| 17 | |

TABLE 1-continued
| Example | Formula |
|---|---|
| 18 |  |
| 19 | 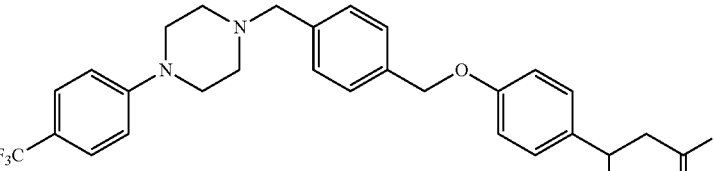 |
| 20 | 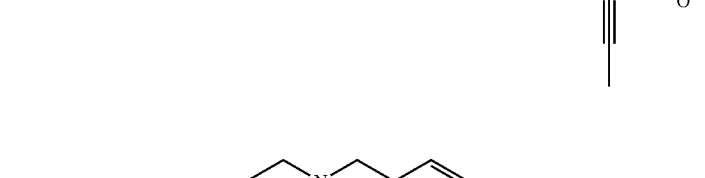 |
| 21 | 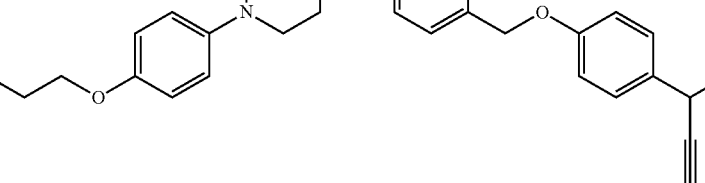 |
| 22 | 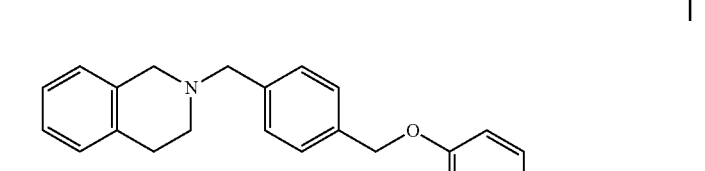 |

TABLE 1-continued
| Example | Formula |
|---------|---------|
| 23 | 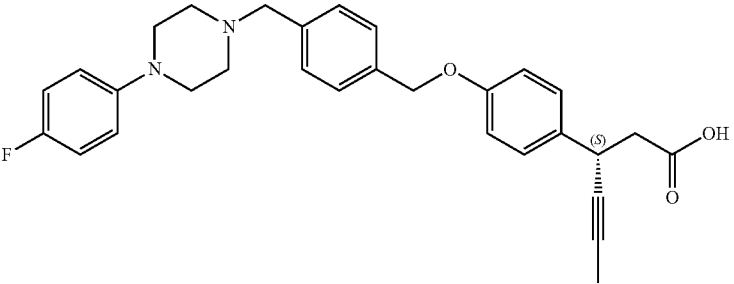 |
| 24 | 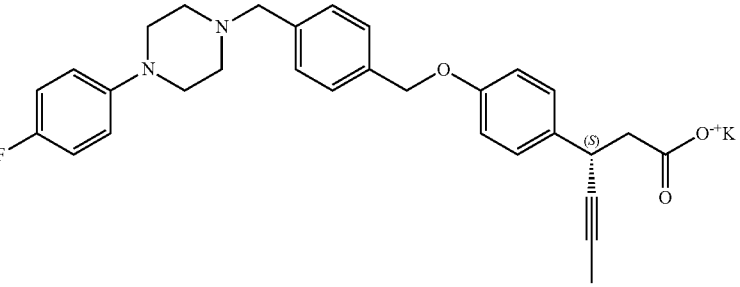 |
| 25 | 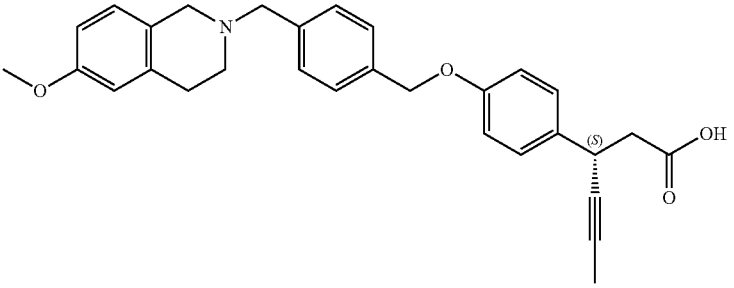 |
| 26 | 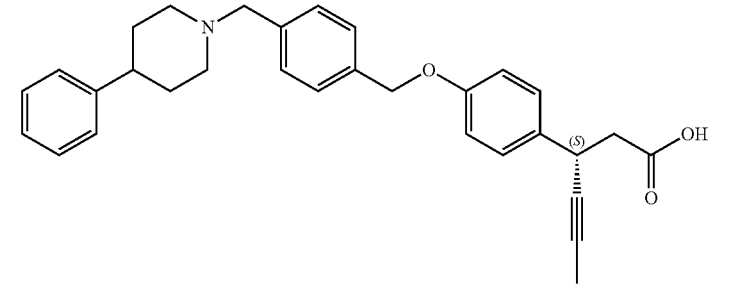 |
| 27 | 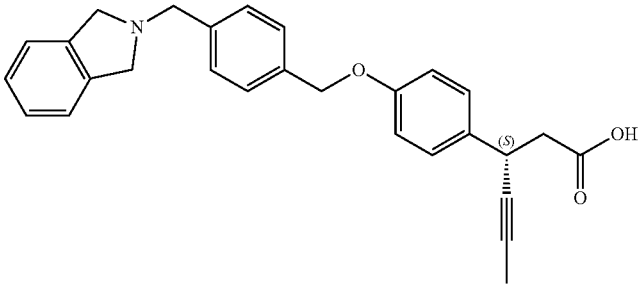 |

TABLE 1-continued

| Example | Formula |
|---|---|
| 28 | (structure: 4-phenyl-1,2,3,6-tetrahydropyridine-N-CH2-phenyl-CH2-O-phenyl-(S)-CH(CH2COOH)-C≡C-CH3) |
| 29 | (structure: 4-methoxymethoxyphenyl-piperazine-N-CH2-phenyl-CH2-O-phenyl-(S)-CH(CH2COOH)-C≡C-CH3) |
| 30 | (structure: 3-isopropyl-1,2,4-oxadiazol-5-yl-piperidine-N-CH2-phenyl-CH2-O-phenyl-(S)-CH(CH2COOH)-C≡C-CH3) |
| 31 | (structure: 3-isopropyl-1,2,4-oxadiazol-5-yl-piperazine-N-CH2-phenyl-CH2-O-phenyl-(S)-CH(CH2COOH)-C≡C-CH3) |
| 32 | (structure: 4-(methylsulfonyl)phenyl-1,2,3,6-tetrahydropyridine-N-CH2-phenyl-CH2-O-phenyl-(S)-CH(CH2COOH)-C≡C-CH3) |

TABLE 1-continued

| Example | Formula |
|---------|---------|
| 33 | |
| 34 | |
| 35 | |
| 36 | |
| 37 | |

TABLE 1-continued
| Example | Formula |
|---|---|
| 38 | 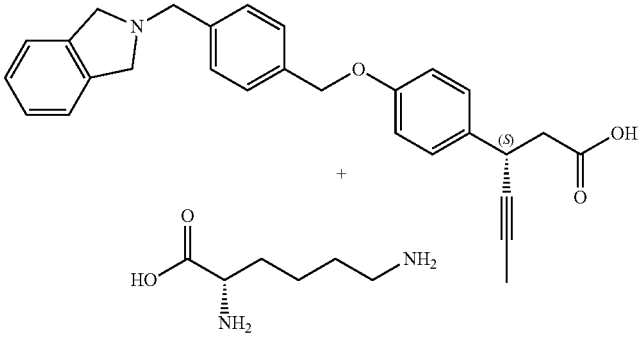 |
| 39 | 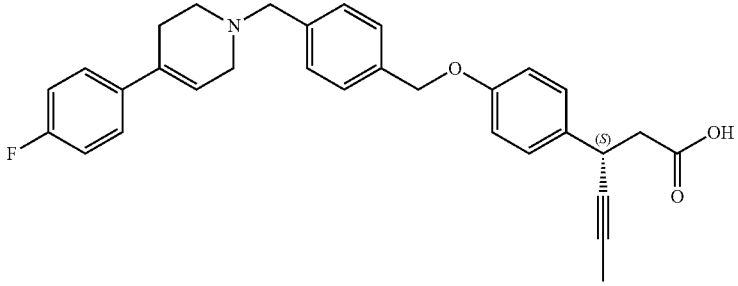 |
| 40 | 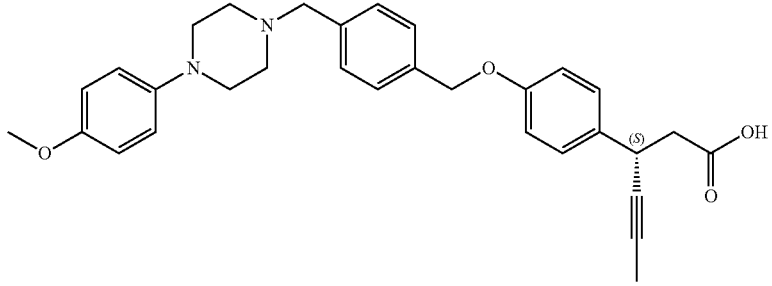 |
| 41 | 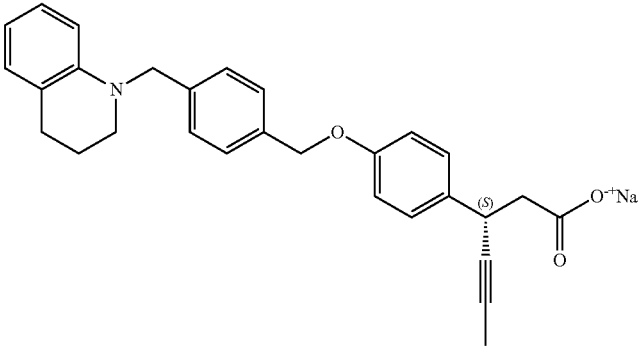 |

TABLE 1-continued
| Example | Formula |
|---|---|
| 42 | 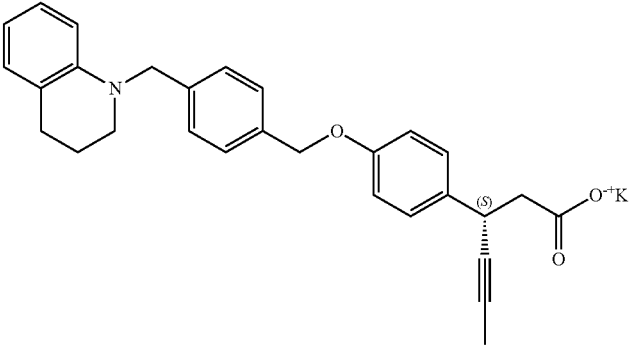 |
| 43 | 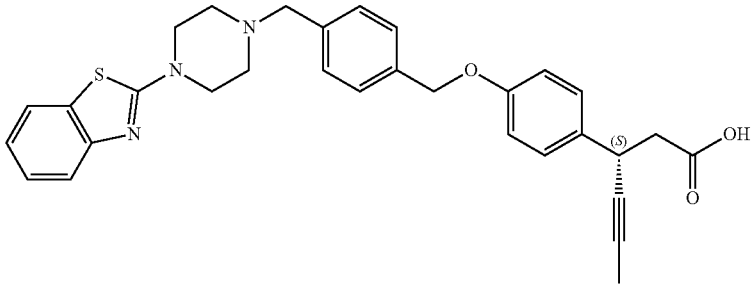 |
| 44 | 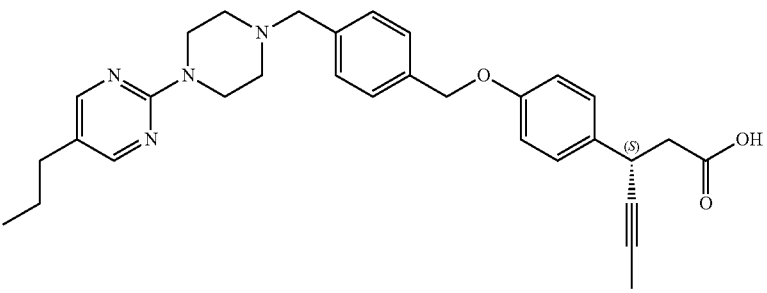 |
| 45 | 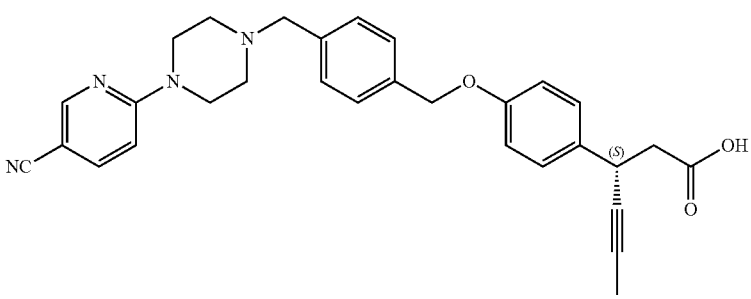 |
| 46 | 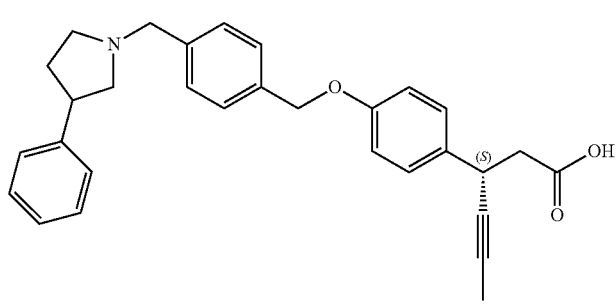 |

TABLE 1-continued
| Example | Formula |
|---|---|
| 47 | 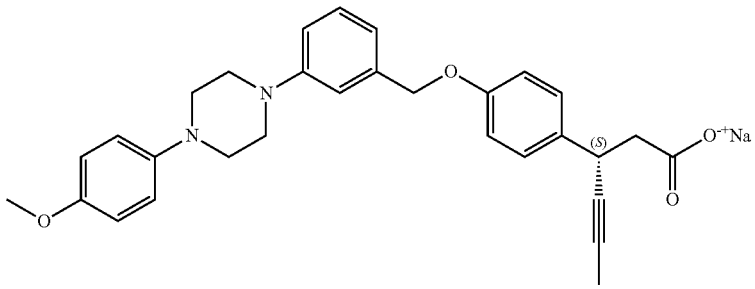 |
| 48 | 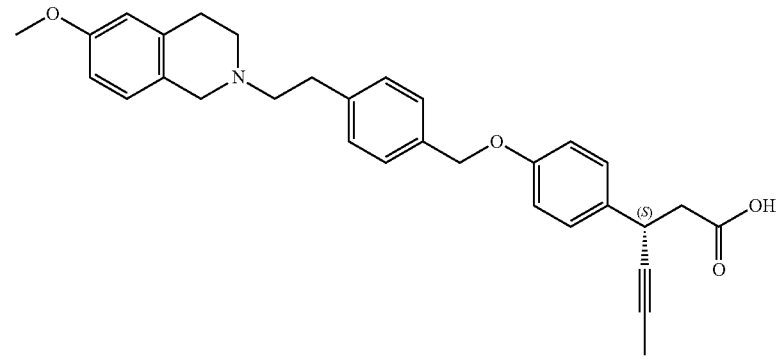 |
| 49 | 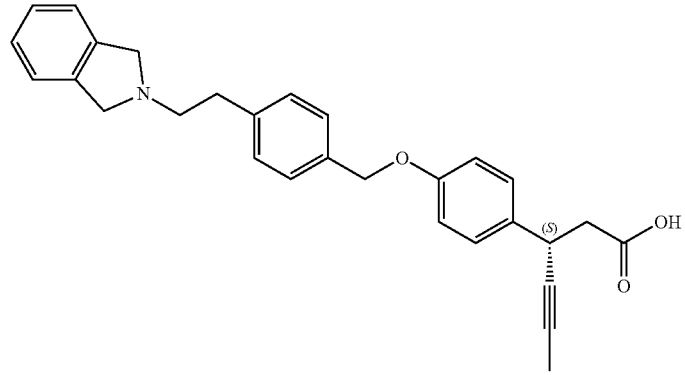 |
| 50 | 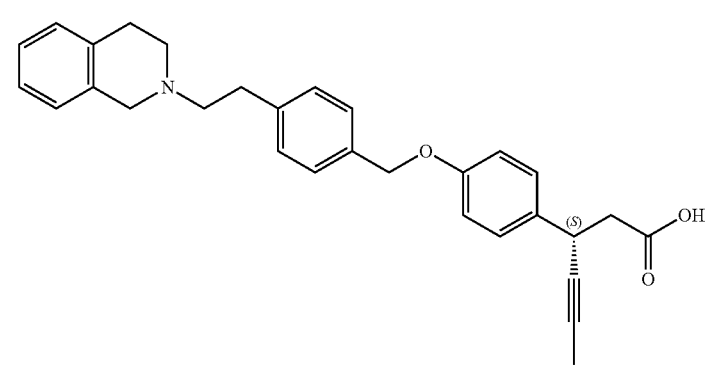 |

TABLE 1-continued

| Example | Formula |
|---|---|
| 51 | 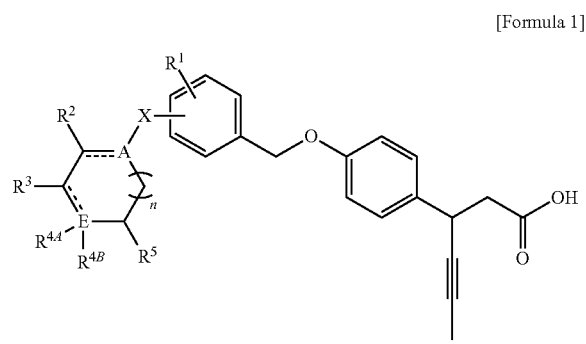 |

In accordance with another aspect of the present invention, there is provided a method for the prevention or treatment of metabolic diseases, the method including administering, to a subject, a pharmaceutically effective amount of a composition containing: (a), as a first active ingredient, a compound represented by formula 1, an optical isomer, hydrate, or solvate thereof, or a pharmaceutically acceptable salt thereof; and (b), as a second active ingredient, at least one compound selected from the group consisting of dipeptidyl peptidase-IV (DPP-IV) inhibitor-based, sulfonylurea-based, thiazolidinedione (TZD)-based, biguanide-based, and sodium/glucose cotransporter 2 (SGLT2) inhibitor-based compounds, as a second active ingredient:

[Formula 1]

Here, Formula 1 is as described in the detailed description of the composition for the prevention or treatment of metabolic diseases.

The mixed composition of the active ingredient and the second active ingredient is not particularly limited to the mixing weight ratio since no side effects or reduced efficacy are caused by the mixing weight ratio, and considering pathological conditions of patients, the known characteristics of the second active ingredient, and the like, the first active ingredient and the second active ingredient may be mixed at appropriate amounts and administered in combination. In an embodiment, the mixing weight ratio is 0.03:1 to 100:1. In another embodiment, the mixing weight ratio is 0.03:1 to 30:1, and in still another embodiment, the mixing weight ratio is 0.03:1 to 10:1.

<Experimental Example 1> Evaluation of activation of GPR40 protein by 3-(4-(benzyloxy)phenyl)hex-4-ynoic acid derivative In order to evaluate the activation of GPR40 by a novel 3-(4-(benzyloxy)phenyl)hex-4-ynoic acid derivative of the present invention, the following experiment was carried out.

The activation of GPR40 protein by a novel 3-(4-(benzyloxy)phenyl)hex-4-ynoic acid derivative of the present invention was evaluated through the change in intracellular calcium concentration due to the activity of GPR40 protein. First, HEK-293 cells were transfected with human GPR40 DNA (Origene, RC218370) by using Fugene HD (Promega, E2311). The transfected HEK-293 cells were seeded in a 96-well black, clear bottom plate (Costar, 3603) and cultured. After 24 hours, the cell culture medium was removed, and replaced with Dulbecco's Modified Eagle Medium (DMEM, 50 µl) supplemented with 1% fetal bovine serum (FBS). For the measurement of calcium concentration, 50 µL of Fluo-4 reagent (Invitrogen, F10471) was added to each well and cultured in a 37° C. incubator for 2 hours. During the culture, the compounds of the examples and the compounds of Comparative Examples 1 and 2 were diluted with 1× Hank's buffered salt solution (HBSS) supplemented with 20 mM 4-(2-hydroxyethyl)-1-piperazineethanesulfonic acid (HEPES) buffer to prepare samples to be treated on cells. Two hours after the initiation of the culture, the prepared samples were automatically injected into the cells using Flexstation 3 (Molecular Devices), and then, the change in intracellular calcium concentration was measured using SoftMax®Pro software for 120 seconds. Here, for a non-treated group, dimethylsulfoxide (DMSO) was injected into the cells to measure the change in calcium concentration. The GPR40 protein activity was calculated from the measured calcium concentration result values using equation 1 below, and the GPR40 activity (EC50 value) by the samples was obtained. The results are shown FIG. 2.

GPR 40 activity=(intracellular calcium concentration increased by the sample)/(intracellular calcium concentration of the non-treated group)×100 [Equation 1]

TABLE 2

| Example | $EC_{50}$ (µM) |
|---|---|
| 1 | C |
| 2 | C |
| 3 | C |
| 4 | C |
| 5 | B |
| 6 | B |
| 7 | A |
| 8 | C |
| 9 | A |
| 10 | C |
| 11 | A |
| 12 | A |
| 13 | C |
| 14 | A |

TABLE 2-continued

| Example | EC$_{50}$ (μM) |
|---|---|
| 15 | C |
| 16 | C |
| 17 | C |
| 18 | C |
| 19 | C |
| 20 | C |
| 21 | B |
| 22 | C |
| 23 | B |
| 24 | B |
| 25 | C |
| 26 | C |
| 27 | A |
| 28 | A |
| 29 | B |
| 30 | C |
| 31 | C |
| 32 | C |
| 33 | C |
| 34 | C |
| 35 | C |
| 36 | C |
| 37 | A |
| 38 | A |
| 39 | B |
| 40 | B |
| 41 | C |
| 42 | C |
| 43 | C |
| 44 | C |
| 45 | C |
| 46 | C |
| 47 | B |
| 48 | C |
| 49 | C |
| 50 | C |
| 51 | C |
| Comparative Example 1 | B |
| Comparative Example 2 | C |

In table 2, A: under 0.20 μM; B: 0.20-0.30 μM; and C: over 0.30 μM.

As shown in Table 2, the compounds of the examples of the present invention had excellent effects in activating the GPR 40 protein at low concentrations. Particularly, the compounds of Examples 7, 9, 11, 12, 14, 27, 28, 37, and 38 activated the GPR40 protein by 50% at very low concentrations, such as 0.20 μM or lower, indicating that the ability thereof to increase the intracellular Ca$^{2+}$ concentration was very excellent compared with that of the compound of Comparative Example 1 (B, 0.28 μM).

Therefore, a novel 3-(4-(benzyloxy)phenyl)hex-4-ynoic acid derivative of the present invention induces excellent GPR40 protein activity and, especially, shows similar or improved GPR40 protein activity compared with a conventional antidiabetic drug (Comparative Example 1), which has been known to activate GPR40 protein to promote the insulin secretion, and thus, a pharmaceutical composition containing the compound of the present invention as an active ingredient can be advantageously used as a pharmaceutical composition for the prevention or treatment of metabolic diseases, such as obesity, type I diabetes, type I diabetes, impaired glucose tolerance, insulin resistance syndrome, hyperglycemia, hyperlipidemia, hypertriglyceridemia, hypercholesterolemia, dyslipidemia, and syndrome X.

<Experimental Example 2> Analysis of calcium flux

In order to evaluate the calcium flux according to the activation of GPR40 by a novel 3-(4-(benzyloxy)phenyl) hex-4-ynoic acid derivative of the present invention, the experiment was conducted by Millipore, the GPCR assay specialized agency.

The compounds of the examples of the invention dissolved in DMSO (dimethyl sulfoxide), PBS (phosphate buffered saline), and DW (distilled water) were diluted three-times with EMD Millipore's GPCR profiler assay buffer. Likewise, the non-treated group (vehicle) and the positive control groups (Comparative Examples 1 and 3) were used to verify the accuracy of the analysis. Each well was prepared using EMD Millipore's GPCR profiler assay buffer. The EMD Millipore's GPCR profiler assay buffer was a Hanks balanced salt solution (HBSS) containing 20 mM HEPES (4-(2-hydroxyethyl)-1-piperazineethanesulfonic acid) and 2.5 mM probenecid (4-(dipropylsulfamoyl) benzoic acid) and adjusted to pH 7.4.

The compound of the example was duplicated at each concentration. The positive control groups (Comparative Examples 1 and 3) for each G protein-coupled receptor (GPCR) were prepared in the same manner as the non-treated group (vehicle). The positive control groups (Comparative Examples 1 and 3) for each G PCR were included in Emax as a concentration exhibiting the maximal activity. Agonist assay was performed by using FLIPR$^{TETRA}$, and fluorescence and luminescence baselines were measured. The compounds of the examples, the non-treated group, and the positive control groups (Comparative Examples 1 and 3) were added to the assay plates. In order to measure the activity of the compound of the example, GPCR activity assay was performed for 180 seconds.

The fluorescence values minus the baseline were compared with Emax values of the positive controls (Comparative Examples 1 and 3) and the non-treated group, and then calculated as a percent (%). The obtained data indicate the inhibition (%) resulted from the comparison of EC$_{50}$ with the non-treated group, and the quality of each plate was evaluated by the statistical data representing the activity % from repeated data values. When the assay data were not satisfactory, an additional experiment was performed.

All the concentration-dependent graphs were made by using GraphPad Prism. The graph was modified by the Sigmoidal dose response, and the minimum value was fixed as 0, and the maximum value was fixed as 100 for the prediction of better effect values.

The results are shown in FIG. 1 and Table 3.

TABLE 3

| Compound | Expected EC$_{50}$ |
|---|---|
| Example 9 | Lower than the measurable concentration (1 nM) |
| Comparative Example 1 | 14 nM |
| Comparative Example 3 | 27 nM |

FIG. 1 is a graph illustrating the activation pattern of GPR40 protein measured according to the concentrations of the compounds of Example 9, Comparative Example 1, and Comparative Example 3.

As shown in FIG. 1, it could be seen that the concentration required to reach 50% of GPR40 activity was very low (lower than the measurable concentration of 1 nM) in the compound of the example compared with the compounds of Comparative Examples 1 and 3. Especially, as shown in Table 3, the compound of the example of the present invention activated GPR40 at a much lower concentration than the compounds of Comparative Example 1 (14 nM) and Comparative Example 3 (27 nM).

Therefore, a novel 3-(4-(benzyloxy)phenyl)hex-4-ynoic acid derivative of the present invention induces excellent GPR40 protein activity and especially, shows significantly excellent GPR40 protein activity compared with conventional antidiabetic drugs (Comparative Examples 1 and 3), which have been known to activate GPR40 protein to promote the insulin secretion, and thus, the pharmaceutical composition containing the novel compound as an active ingredient can be advantageously used as a pharmaceutical composition for the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 3> Analysis of CYP inhibition

In order to evaluate the interaction between a novel 3-(4-(benzyloxy)phenyl)hex-4-ynoic acid derivative of the present invention and a drug, the following experiment was carried out.

CYP enzymes are involved in the drug metabolism, and depending on the inhibitory effects on these enzymes, the dose of a drug and the toxicity due to the co-administration concentration for co-administration with another drug can be predicted. Therefore, the inventors measured the inhibitory effects of the compounds of the examples of the invention on CYP3A4, CYP2C9, CYP1A2, CYP2D6, and CYP2C19 existing in the human body. Here, the Invitrogen kit (P2862) was used as the CYP2D6 inhibition kit, and the BD GENTEST kit (459100, 459300, 459400, 459500) was used as the CYP1A2, CYP2C9, CYP2C19, and CYP3A4 inhibition kits. As for the Invitrogen kit, a test sample was diluted in distilled water at 2.5× of the final experimental concentration.

P450 BACULOSOMES® reagent and a reproducer (100×) provided in the Invitrogen kit were diluted in Vivid® CYP450 reaction buffer (2×) at the concentration that matched the target CYP450. The prepared 2.5× sample (80 μL) and the diluted P450 BACULOSOMES® reagent mixture (100 μL) were mixed in the U-bottom 96-well plate, followed by pre-culture for 20 minutes. Vivid® CYP450 substrate and NADP+ (100×) were diluted in Vivid® CYP450 reaction buffer (2×) at the concentration that matched the target CYP450 and the kind of substrate. Upon completion of the pre-culture, a substrate-nicotinamide adenine dinucleotide phosphate (NADP) mixture (20 μL) was added thereto, followed by reaction for 1 hour. Upon completion of the reaction, the reactant was transferred onto the white plate, and then fluorescence was measured with a microplate reader (CYP 2D6 excitation wavelength: 400 nm, absorption wavelength: 502 nm).

As for the BD GENTEST kit, a test sample was diluted in acetonitrile at 50× of the final experimental concentration. A NADPH-coenzyme mixture was prepared by diluting coenzyme, G6PDH, and a regulatory protein provided in the kit with distilled water to a concentration instructed by the kit. The prepared 50× sample (4 μL) and the NADPH-coenzyme mixture (96 μL) were mixed in the U-bottom 96-well plate, followed by pre-culture for 10 minutes in a 37° C. incubator. The enzyme/substrate mixture was prepared by diluting a buffer (0.5 M potassium phosphate, pH 7.4) and each CYP450 enzyme/substrate mixture with distilled water to a concentration instructed according to the kind of CYP450. Upon completion of the pre-culture, 100 μL of the enzyme/substrate mixture was added to the plate, followed by reaction in a 37° C. incubator for 15 minutes (CYP 1A2), 30 minutes (CYP 3A4 and CYP 2C19) or one and half hours (CYP 2C9). Upon completion of the reaction, the reactant was transferred onto the white plate, and then fluorescence was measured with a microplate reader (excitation wavelength: 410 nm, absorption wavelength: 460 nm for CYP 1A2 and CYP 2C19; and excitation wavelength: 409 nm, absorption wavelength: 530 nm for CYP 2C9 and CYP 3A4). The values measured above were converted into % as the inhibition of the sample compared with the non-treated group. The results are shown in Table 4.

TABLE 4

| Example (10 μM) | CYP Inhibition (%) | | | | |
|---|---|---|---|---|---|
| | 1A2 | 2C9 | 2C19 | 2D6 | 3A4 |
| 1 | 0 | 42.8 | 18.3 | 1.9 | 12.7 |
| 3 | 0 | 21.1 | 19.4 | 6.0 | 33.1 |
| 4 | 0 | 41.5 | 45.4 | 19.3 | 35.0 |
| 7 | 4.3 | 47.1 | 3.7 | 13.9 | 15.5 |
| 9 | 4.3 | 47.1 | 3.7 | 13.9 | 15.5 |
| 21 | 4.0 | 75.9 | 46.5 | 16.1 | 27.3 |
| 26 | 0.7 | 31.5 | 13.2 | 2.3 | 14.1 |
| 29 | 0.7 | 26.7 | 9.7 | 18.2 | 0 |
| 36 | 16.6 | 0 | 10.8 | 1.8 | 11.5 |
| 38 | 2.2 | 34.4 | 13.2 | 15.6 | 18.1 |
| 40 | 9.7 | 18.4 | 19.5 | 17.9 | 0 |
| Comparative Example 1 | 0.8 | 81.2 | 12.4 | 4.3 | 10.0 |
| Comparative Example 2 | 0 | 43.9 | 34.5 | 63.2 | 42.0 |

As shown in Table 4, the compounds of the examples of the present invention showed low activity on the CYP450 inhibition, suggesting that the risk of side effects due to the drug interaction is low. More specifically, the compounds of almost all the examples of the present invention showed enzyme inhibitions of about 50% or less on CYP 1A2, CYP 2C9, CYP 2C19, CYP 2D6, and CYP 3A4 enzymes. In particular, the compounds of the examples showed relatively very low enzyme inhibitory activity on CYP 2C9 enzyme, compared with the compound of Comparative Example 1 (81.2%), which is used as a conventional anti-diabetic drug that can promote the insulin secretion by activating GPR40 protein. In addition, the compounds of the examples of the present invention showed relatively very low enzyme inhibitory activity on CYP 2D6 enzyme, compared with the compound of Comparative Example 2 (63.2%).

Since a novel 3-(4-(benzyloxy)phenyl)hex-4-ynoic acid derivative of the present invention has significantly low CYP enzyme inhibitory activity, a pharmaceutical composition containing the novel compound as an active ingredient can be co-administered together with other drugs, and thus can be advantageously used in the treatment of complications including metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 4> Oral Glucose Tolerance Test (OGTT) 1

In order to evaluate the in vivo blood glucose lowering effect of a novel 3-(4-(benzyloxy)phenyl)hex-4-ynoic acid derivative of the present invention, the following experiment was carried out.

Male Sprague Dawley rats aged 8-10 weeks old were acclimated for at least 7 days, and then only healthy animals were used for the oral glucose tolerance test (OGTT test). After fasting for 16-18 hours, five rats per group were randomly grouped and orally administered with the compounds prepared in Examples 2, 3, 4, 6, 9, 12, 14, 16, 25, 29, 36, 37, 41, 43, and 44 at a dose of 10 mg/kg each. Here, as for a non-treated group (vehicle), a solution (PEG 400/Tween 80/0.25% CMC, 5%/5%/90%, v/v/v) containing 5% polyethyleneglycol/5% tween 80/0.25% carboxymethylcelluluse (CMC) was orally administered at the same dose. Glucose (4 g/kg) was orally administered at a dose of 5 ml/kg 30 minutes after each sample was administered. Then, the blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and the blood glucose was measured through tail vein puncture. The reduction (%) of blood glucose AUC was measured and the results are shown in Table 5 below.

TABLE 5

| Example | % AUC |
| --- | --- |
| 2 | 17.2 |
| 3 | 12.5 |
| 4 | 16.2 |
| 6 | 15.2 |
| 9 | 24.7 |
| 12 | 31.0 |
| 14 | 27.7 |
| 16 | 21.1 |
| 25 | 24.6 |
| 29 | 27.1 |
| 36 | 22.6 |
| 37 | 28.5 |
| 41 | 23.7 |
| 43 | 21.2 |
| 44 | 22.8 |
| Comparative Example 1 | 16.2 |

As shown in Table 5, the compounds of the examples of the present invention had a blood sugar lowering effect of, on average, 21.9% compared with the non-treated group, suggesting that the compounds of the examples have excellent in vivo advantageous effects. More specifically, the compound of Comparative Example 1, known as a conventional GPR40 protein activator, was verified to have a blood glucose lowering effect of 16.2%, but the compounds of the examples of the present invention showed more excellent blood glucose lowering effects compared with the compound of Comparative Example 1. Especially, the compounds of Examples 9, 12, 14, 29, and 37 showed blood glucose lowering effects of 24.7%, 31.0%, 27.7%, 27.1%, and 28.5%, respectively, and thus exhibited more excellent efficacy compared with the compound of Comparative Example 1.

Therefore, a novel 3-(4-(benzyloxy)phenyl)hex-4-ynoic acid derivatives of the present invention has an excellent effect of activating GPR40 protein, and thus has an excellent insulin secretion promoting effect, leading to a significantly excellent blood glucose lowering effect, and thus, a pharmaceutical composition containing the novel compound as an active ingredient can be advantageously used as a pharmaceutical composition for the treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 5> Oral Glucose Tolerance Test (OGTT) 2

In order to evaluate the in vivo blood glucose lowering effect of a novel 3-(4-(benzyloxy)phenyl)hex-4-ynoic acid derivative of the present invention, the following experiment was carried out.

Male Goto-Kakizaki (GK) rats aged 22-23 weeks, as non-obese type II diabetic models, were acclimated for at least 7 days, and then only healthy animals were used for the oral glucose tolerance test (OGTT test). After fasting for 16-18 hours, five rats per group were randomly grouped and orally administered with the compounds prepared in Examples 5, 9, 14, 28, 37, and 47 at a dose of 0.3-10 mg/kg each. Here, as for a non-treated group (vehicle), a solution (PEG 400/Tween 80/0.25% CMC, 5%/5%/90%, v/v/v) containing 5% polyethyleneglycol/5% tween 80/0.25% carboxymethylcelluluse (CMC) was orally administered at the same dose. Glucose (4 g/kg) was orally administered at a dose of 5 ml/kg 60 minutes after each sample was administered. Then, the blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and the blood glucose was measured through tail vein puncture. The reduction (%) of blood glucose AUC was measured and the results are shown in Table 6 below.

TABLE 6

| Examples | Dose (mg/kg) | % AUC |
| --- | --- | --- |
| Example 5 | 0.3 | C |
|  | 1 | C |
|  | 3 | C |
|  | 10 | B |
| Example 9 | 0.3 | C |
|  | 1 | C |
|  | 3 | A |
|  | 10 | A |
| Example 14 | 0.3 | C |
|  | 1 | C |
|  | 3 | B |
|  | 10 | B |
| Example 28 | 0.3 | C |
|  | 1 | C |
|  | 3 | C |
|  | 10 | B |
| Example 37 | 0.3 | C |
|  | 1 | B |
|  | 3 | B |
|  | 10 | A |
| Example 47 | 0.3 | C |
|  | 1 | C |
|  | 3 | B |
|  | 10 | B |
| Comparative Example 1 | 10 | B |

In table 6, A: over 35.0%; B: 25.0-35.0%; and C: under 25.0%.

As shown in Table 6, the compounds of the examples of the present invention showed a blood glucose lowering effect of, on average, at least 30.0% compared with the non-treated group at the same dose of the compound of Comparative Example 1 (10 mg/kg). More specifically, the compound of Comparative Example 1 showed a blood glucose lowering effect of 25.3% (B) at a dose of 10 mg/kg, while the compounds of Examples 5, 9, 14, 28, 37, and 47 showed similar blood glucose lowering effects at a dose of 3 mg/kg compared with the compound of Comparative Example 1. In particular, the compounds of Examples 9 and 37 showed blood glucose lowering effects of 35.0% or more at a dose of 10 mg/kg, indicating more excellent efficacy compared with the compound of Comparative Example 1.

Therefore, a novel 3-(4-(benzyloxy)phenyl)hex-4-ynoic acid derivative of the present invention has an excellent effect of activating GPR40 protein, and thus has an excellent insulin secretion promoting effect, leading to a significantly excellent blood glucose lowering effect, and thus, a pharmaceutical composition containing the novel compound as an active ingredient can be advantageously used as a pharmaceutical composition for the treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 6> Oral Glucose Tolerance Test (OGTT) 3

In order to evaluate the in vivo blood glucose lowering effect of a novel 3-(4-(benzyloxy)phenyl)hex-4-ynoic acid derivative of the present invention, the following experiment was carried out.

Male Otsuka Long-Evans Tokushima fatty (OLETF) rats aged 29-30 weeks, as obese type II diabetic models, were acclimated for at least 7 days, and then only healthy animals were used for the oral glucose tolerance test (OGTT test). After fasting for 16-18 hours, five rats per group were randomly grouped and orally administered with the compounds prepared in Examples 5, 9, 14, 28, 37, and 47 at a dose of 1-10 mg/kg each. Here, as for a non-treated group (vehicle), a solution (PEG 400/Tween 80/0.25% CMC, 5%/5%/90%, v/v/v) containing 5% polyethyleneglycol/5% tween 80/0.25% carboxymethylcelluluse (CMC) was orally administered at the same dose. Glucose (4 g/kg) was orally administered at a dose of 5 ml/kg 60 minutes after each sample was administered. Then, the blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and the blood glucose was measured through tail vein puncture. The reduction (%) of blood glucose AUC was measured and the results are shown in Table 7 below.

TABLE 7

| Examples | Dose (mg/kg) | % AUC |
| --- | --- | --- |
| Example 5 | 1 | B |
|  | 3 | B |
|  | 10 | A |
| Example 9 | 1 | B |
|  | 3 | A |
|  | 10 | A |
| Example 14 | 1 | C |
|  | 3 | B |
|  | 10 | B |
| Example 28 | 1 | B |
|  | 3 | B |
|  | 10 | B |
| Example 37 | 1 | A |
|  | 3 | A |
|  | 10 | A |
| Example 47 | 1 | C |
|  | 3 | C |
|  | 10 | B |
| Comparative Example 1 | 10 | B |

In table 7,
A: over 35.0%;
B: 25.0-35.0%; and
C: under 25.0.

As shown in Table 7, the compounds of the examples of the present invention showed a blood glucose lowering effect of, on average 35.0% or more, compared with the non-treated group at the same dose of the compound of Comparative Example 1 (10 mg/kg). More specifically, the compound of Comparative Example 1 showed a blood glucose lowering effect of 31.6% (B) at a dose of 10 mg/kg, while the compounds of Examples 9 and 37 showed more excellent blood glucose lowering effects at a dose of 1 mg/kg compared with the compound of Comparative Example 1. In particular, the compounds of Examples 9 and 37 showed blood glucose lowering effects of 35.0% or more at a dose of 10 mg/kg, indicating more excellent efficacy compared with the compound of Comparative Example 1.

Therefore, a novel 3-(4-(benzyloxy)phenyl)hex-4-ynoic acid derivatives of the present invention has an excellent effect of activating GPR40 protein, and thus has an excellent insulin secretion promoting effect, leading to a significantly excellent blood glucose lowering effect, and thus, a pharmaceutical composition containing the novel compound as an active ingredient can be advantageously used as a pharmaceutical composition for the treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 7> Measurement of Blood Glucagon-Like Peptide-1 (GLP-1) Concentration Increase after Oral Administration In order to evaluate the blood GLP-1 concentration increase rate after the administration of a novel 3-(4-(benzyloxy)phenyl)hex-4-ynoic acid derivative of the present invention, the following experiment was carried out.

Male Sprague Dawley (SD) rats aged 10-12 weeks were acclimated for at least 7 days, and then only healthy animals were used for the following experiment. After fasting for 16-18 hours, five rats per group were randomly grouped and orally administered with the compound prepared in Example 9 at a dose of 10-100 mg/kg each (administration solvent volume: 5 mL/kg). Here, as for a non-treated group (vehicle), a solution (PEG 400/Tween 80/0.25% CMC, 5%/5%/90%, v/v/v) containing 5% polyethyleneglycol/5% tween 80/0.25% carboxymethylcelluluse (CMC) was orally administered at the same dose. After 20 minutes, about 0.5 ml of whole blood was collected by direct blood collection through cardiac injection, and the collected blood was immediately transferred to a sample tube treated with the dipeptidyl peptidase IV (DPPIV) inhibitor and ethylenediaminetetraacetic acid (EDTA), and placed in a container containing ice. The collected blood was centrifuged at 3600 rpm for 10 minutes to separate the plasma, and the separated plasma was measured for the plasma GLP-1 concentration through the GLP-1 ELISA kit (Millipore, USA). The results are shown FIG. 2.

FIG. 2 is a graph illustrating the blood GLP-1 concentration when Sprague Dawley (SD) rats were orally administered with the compounds of Example 9 and Comparative Example 1.

As shown in FIG. 2, compared with the glucose treated group (Veh.), the compound of Comparative Example 1 did not show an effect of increasing the concentration of GLP-1 hormone, which promotes the insulin secretion, after administration, but the compound of Example 9 increased the blood GLP-1 concentration at the dose administered to the SD rats.

Therefore, a novel 3-(4-(benzyloxy)phenyl)hex-4-ynoic acid derivative of the present invention has an excellent effect of promoting the secretion of GLP-1 hormone, compared with the compound of Comparative Example 1, and especially, showed very excellent efficacy in the diabetic animal models. In addition, the novel compounds of the present invention can be expected to prevent the dysfunction of beta cells and weight gain by promoting the secretion of GLP-1, and can be advantageously used as a pharmaceutical composition for the treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

Meanwhile, the compounds represented by formula 1 of the present invention can be formulated in various forms according to the purpose of use. The following are examples of some formulations containing a compound represented by formula 1 of the present invention as an active ingredient, but the present invention is not limited thereto.

<Experimental Example 8> Oral Glucose Tolerance Test (OGTT) by Co-Administration with Dipeptidyl Peptidase IV (DPPIV) Inhibitor In order to evaluate the in vivo blood glucose lowering effect at the co-administration with a novel 3-(4-(benzyloxy)phenyl)hex-4-ynoic acid derivative of the present invention and a dipeptidyl peptidase IV (DPPIV) inhibitor, the following experiment was carried out.

8-1. Mouse Model Experiment

After fasting for 16-18 hours, male diet-induced obesity (DIO) mice aged 29 to 30 weeks were randomly grouped into five animals per each group, and then orally administered with the compound prepared in Example 9 at a dose of 30-100 mg/kg (volume of administration solvent: 5 ml/kg). Here, as for a non-treated group, 5% carboxymethyl cellulose (CMC) was orally administered at the same dose. In addition, 10 mg/kg of sitagliptin, which is a drug well known as a dipeptidyl peptidase IV (DPPIV) inhibitor, was administered alone. Furthermore, 10 mg/kg of sitagliptin and 30-100 mg/kg of the compound prepared in Example 9 were co-administered. Each test sample and 0.5% carboxymethyl cellulase (CMC) were orally administered at 5 ml/kg.

After 60 minutes, glucose (4 g/kg) was orally administered at a dose of 5 ml/kg. The blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and the blood glucose was measured through tail vein puncture. The results are shown in FIG. 3 and Table 3 below as a reduction (%) of blood glucose AUC.

TABLE 8

| Compound | Reduction (%) of blood glucose AUC |
|---|---|
| Sitagliptin (10 mg/kg) | 17.7 |
| Example 9 (30 mg/kg) | 10.1 |
| Example 9 (100 mg/kg) | 15.4 |
| Sitagliptin (10 mg/kg) + Example 9 (30 mg/kg) | 20.2 |
| Sitagliptin (10 mg/kg) + Example 9 (100 mg/kg) | 26.2 |

Figure 3:
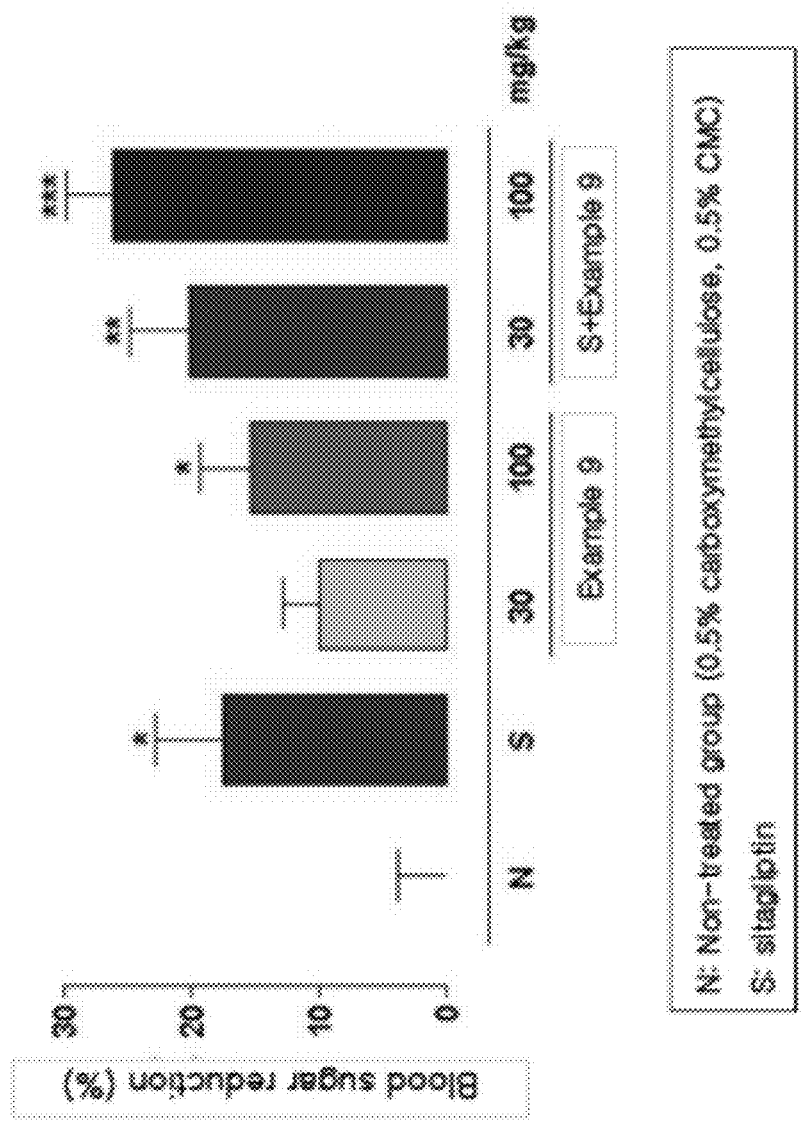
FIG. 3 is a graph illustrating the blood glucose reduction (%) shown when diet-induced obesity (DIO) mice were administered with the compound of Example 9 or sitagliptin alone or co-administered with the compound of Example 9 and sitagliptin.

As shown in FIG. 3 and table 8 above, the blood glucose lowering effect was more excellent when sitagliptin (10 mg/kg) and the compound (30 mg/kg or 100 mg/kg) prepared in Example 9 were co-administered rather than when sitagliptin (10 mg/kg) was used alone.

8-2. Sprague Dawley (SD) Rat Model Experiment

Male Sprague Dawley (SD) rats aged 8-10 weeks were acclimated for at least 7 days, and then only healthy animals were used for the OGTT experiment. After fasting for 16-18 hours, six rats per group were randomly grouped and administered with vehicle (0.5%, carboxymethyl cellulose (CMC)) or the compound of Example 9 (3 mg/kg) or linagliptin (1, 3, or 10 mg/kg), or co-administered with the compound of Example 9 (3 mg/kg) plus linagliptin (1, 3, or 10 mg/kg). Vehicle and the compound of Example 9 were orally administered at 10 ml/kg. After 30 minutes of administration of the vehicle or the compound of Example 9, glucose (4 g/kg) was orally administered at a dose of 5 ml/kg. The blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and the blood glucose was measured through tail vein puncture. The results are shown as a reduction (%) of blood glucose AUC. The reduction (%) of AUC was shown in Table 9 below and FIG. 7.

The experimental results were expressed as mean and standard error (Mean±SE), and the differences between the control and the experimental groups were tested by one-way ANOVA (a Dunnett method) of "GraphPad Prism 4" software (Graphpad co., La Jolla, Calif., USA). Here, p<0.05 was considered statistically significant.

In the co-administration of various doses of linagliptin and the compound of Example 9, the reduction (%) of AUC was observed to increase to values close to the threshold value that can be observed in the experimental environment, and each test group showed an area under curve (AUC) reduction effect of about 5.8-24.4% compared with the vehicle. These results indicate that the co-administration of the compound of Example 9 and a dipeptidyl peptidase IV-based drug can maximize the efficacy of the dipeptidyl peptidase IV-based drug while reducing the dose of the dipeptidyl peptidase IV-based drug.

TABLE 9

| Compound | Reduction (%) of blood glucose AUC |
|---|---|
| Example 9 (3 mg/kg) | 14.8 |
| Linagliptin (1 mg/kg) | 5.8 |
| Linagliptin (3 mg/kg) | 7.9 |
| Linagliptin (10 mg/kg) | 11.8 |
| Example 9 (3 mg/kg) + Linagliptin (1 mg/kg) | 24.1 |
| Example 9 (3 mg/kg) + Linagliptin (3 mg/kg) | 24.3 |
| Example 9 (3 mg/kg) + Linagliptin (10 mg/kg) | 24.4 |

Therefore, the co-administration of a novel 3-(4-(benzyloxy)phenyl)hex-4-ynoic acid derivative of the present invention and a dipeptidyl peptidase IV (DPPIV)-based drugs shows an excellent blood glucose lowering effect compared with the administration of the drug alone, and thus, a pharmaceutical composition containing the derivative of the present invention and another active ingredient can be advantageously used in the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 9> Oral Glucose Tolerance Test (OGTT) by Co-Administration with Sulfonylurea-Based Drug In order to evaluate the in vivo blood glucose lowering effect by co-administration of a novel 3-(4-(benzyloxy)phenyl)hex-4-ynoic acid derivative of the present invention and a sulfonylurea-based drug, the following experiment was carried out.

After fasting for 16-18 hours, male diet-induced obesity (DIO) mice aged 29 to 30 weeks were randomly grouped into five animals per each group, and then orally administered with the compound prepared in Example 9 at a dose of 10-100 mg/kg (volume of administration solvent: 10 ml/kg). Here, as for a non-treated group, 5% carboxymethyl cellulose (CMC) was orally administered at the same dose. In addition, 10 mg/kg of glimepiride, which is well known as a sulfonylurea-based drug, was administered alone. Furthermore, 10 mg/kg of glimepiride and 10-100 mg/kg of the compound prepared in Example 9 were co-administered. The saline and test materials were orally administered at 5 ml/kg.

After 60 minutes, glucose (4 g/kg) was orally administered at a dose of 5 ml/kg. The blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and the blood glucose was measured through tail vein puncture. The results are shown in FIG. 4 and Table 10 below as a reduction (%) of blood glucose AUC.

TABLE 10

| Compound | Reduction (%) of blood glucose AUC |
|---|---|
| Glimepiride (10 mg/kg) | 44.6 |
| Example 9 (10 mg/kg) | 9.1 |
| Example 9 (30 mg/kg) | 11.4 |
| Example 9 (100 mg/kg) | 12.7 |
| Glimepiride (10 mg/kg) + Example 9 (10 mg/kg) | 49.6 |
| Glimepiride (10 mg/kg) + Example 9 (30 mg/kg) | 51.6 |
| Glimepiride (10 mg/kg) + Example 9 (100 mg/kg) | 53.9 |

Figure 4:
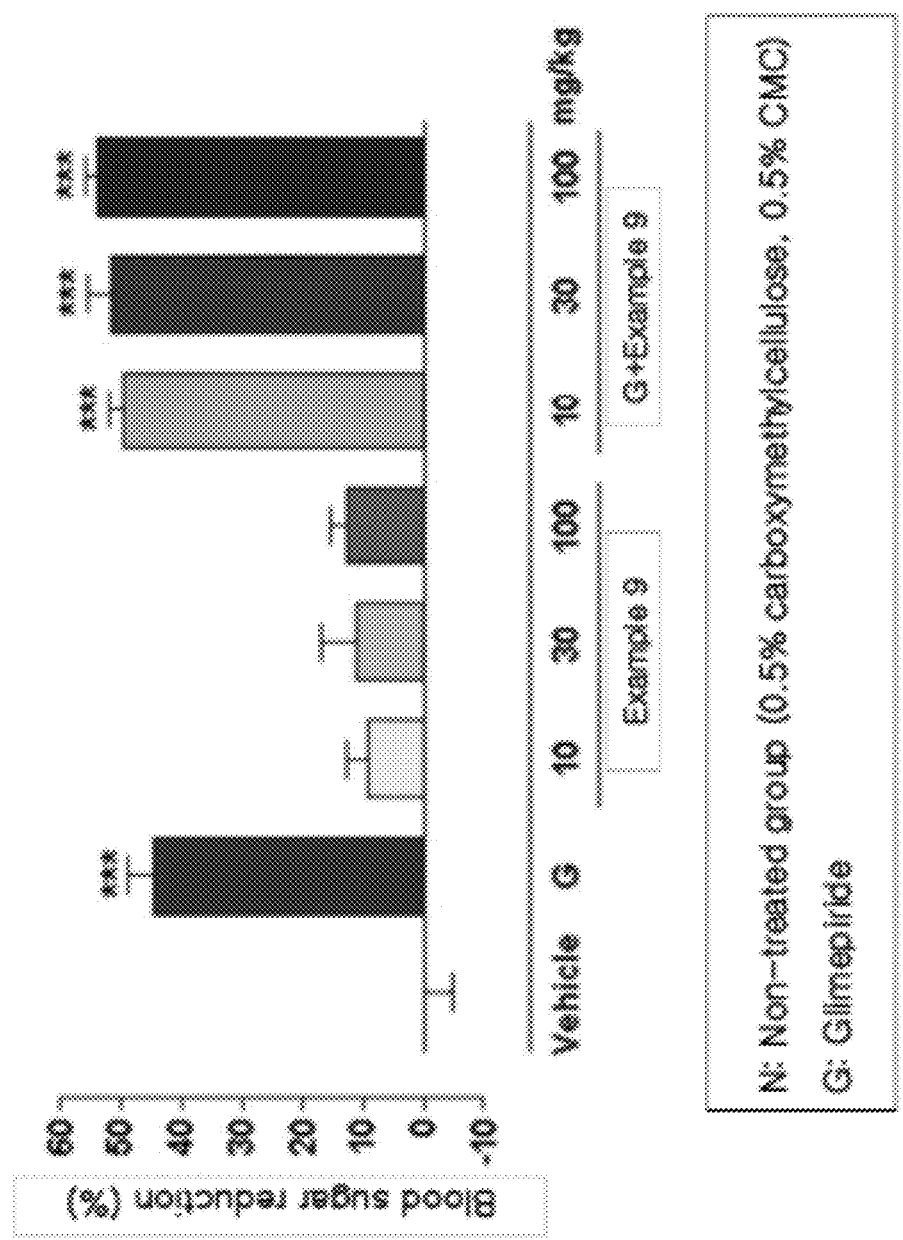
FIG. 4 is a graph illustrating the blood glucose reduction (%) shown when diet-induced obesity (DIO) mice were administered with the compound of Example 9 or glimepiride alone or co-administered with the compound of Example 9 and glimepiride.

As shown in FIG. 4 and table 10 above, the blood glucose lowering effect was more excellent when glimepiride (10 mg/kg) and the compound (30 mg/kg or 100 mg/kg) prepared in Example 9 were co-administered rather than when sitagliptin (10 mg/kg) was used alone.

Therefore, the co-administration of a novel 3-(4-(benzyloxy)phenyl)hex-4-ynoic acid derivative of the present invention and a sulfonylurea-based drug shows an excellent blood glucose lowering effect compared with the administration of the drug alone, and thus, a pharmaceutical composition according to the present invention can be advantageously used in the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 10> Oral Glucose Tolerance Test (OGTT) by Co-Administration with Thiazolidinedione (TZD)-Based Drug In order to evaluate the in vivo blood glucose lowering effect by co-administration of a novel 3-(4-(benzyloxy)phenyl)hex-4-ynoic acid derivative of the present invention and a thiazolidinedione (TZD)-based drug, the following experiment was carried out.

After fasting for 16-18 hours, male diet-induced obesity (DIO) mice aged 29 to 30 weeks were randomly grouped into five animals per each group, and then orally administered with the compound prepared in Example 9 at a dose of 10-30 mg/kg (volume of administration solvent: 10 ml/kg). Here, as for a non-treated group, 5% carboxymethyl cellulose (CMC) was orally administered at the same dose. In addition, 10 mg/kg of rosiglitazone and pioglitazone, which are well known as thiazolidinedione (TZD)-based drugs, were administered alone. Furthermore, 10 mg/kg of rosiglitazone and pioglitazone each and 10-30 mg/kg of the compound prepared in Example 9 were co-administered. The saline and test materials were orally administered at 5 ml/kg.

After 60 minutes, glucose (4 g/kg) was orally administered at a dose of 5 ml/kg. The blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and the blood glucose was measured through tail vein puncture. The results are shown in FIG. 5 and Table 11 below as a reduction (%) of blood glucose AUC.

TABLE 11

| Compound | Reduction (%) of blood glucose AUC |
|---|---|
| Rosiglitazone (5 mg/kg) | 17.1 |
| Pioglitazone (10 mg/kg) | 27.9 |
| Example 9 (10 mg/kg) | 24.9 |
| Example 9 (30 mg/kg) | 20.2 |
| Rosiglitazone (5 mg/kg) + Example 9 (10 mg/kg) | 23.5 |
| Rosiglitazone (5 mg/kg) + Example 9 (30 mg/kg) | 23.3 |
| Pioglitazone (10 mg/kg) + Example 9 (10 mg/kg) | 29.2 |
| Pioglitazone (10 mg/kg) + Example 9 (30 mg/kg) | 27.2 |

Figure 5:
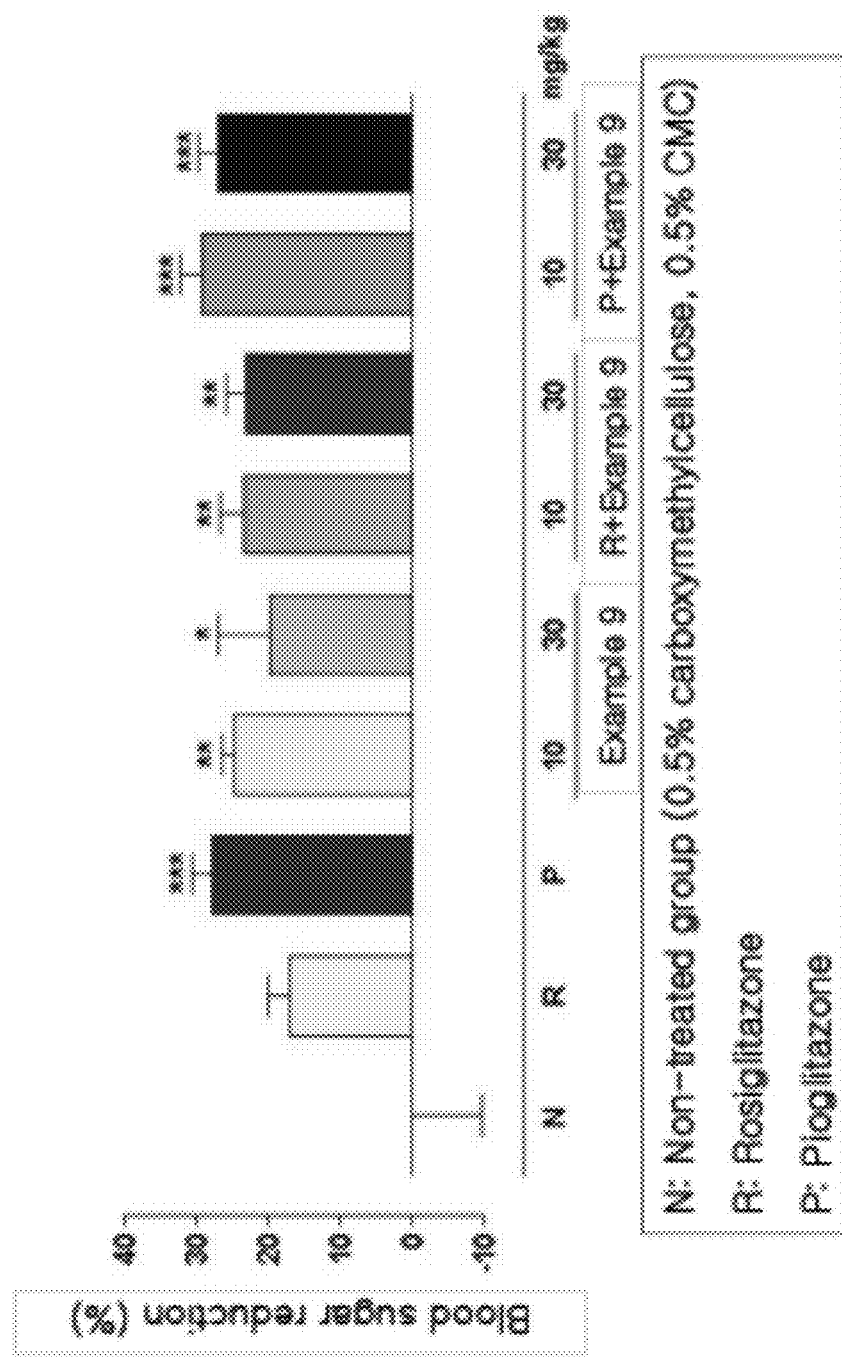
FIG. 5 is a graph illustrating the blood glucose reduction (%) shown when diet-induced obesity (DIO) mice were administered with the compound of Example 9, rosiglitazone, or pioglitazone or alone or co-administered with the compound of Example 9 and rosiglitazone or the compound of Example 9 and pioglitazone.

As shown in FIG. 5 and table 11 above, the blood glucose lowering effect was more excellent when rosiglitazone (5 mg/kg) and the compound (10 mg/kg or 30 mg/kg) prepared in Example 9 were co-administered rather than when rosiglitazone (5 mg/kg) was used alone. The blood glucose lowering effect was also more excellent when pioglitazone (10 mg/kg) and the compound (10 mg/kg) prepared in Example 9 were co-administered rather than when pioglitazone (10 mg/kg) was used alone Therefore, the co-administration of a novel 3-(4-(benzyloxy)phenyl)hex-4-ynoic acid derivative of the present invention and a thiazolidinedione (TZD)-based drug shows an excellent blood glucose lowering effect compared with the administration of the drug alone, and thus, a pharmaceutical composition containing the derivative of the present invention and another active ingredient can be advantageously used in the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 11> Oral Glucose Tolerance Test (OGTT) by Co-Administration with Biguanide-Based Drug In order to evaluate the in vivo blood glucose lowering effect by co-administration of a novel 3-(4-(benzyloxy) phenyl)hex-4-ynoic acid derivative of the present invention and a biguanide-based drug, the following experiment was carried out.

11-1. Type II Diabetic Disease Rat Model Experiment

After fasting for 16-18 hours, male Zucker diabetic fatty (ZDF) rats aged 8 weeks were randomly grouped into five animals per each group, and then orally administered with the compound prepared in Example 9 at a dose of 1-10 mg/kg (volume of administration solvent: 5 ml/kg). Here, as for a non-treated group, vehicle (5% carboxymethyl cellulose (CMC)) was orally administered at the same dose. In addition, 50 mg/kg of metformin, which is well known as a biguanide-based drug, was administered alone. Furthermore, 50 mg/kg of metformin and 1-10 mg/kg of the compound prepared in Example 9 were co-administered.

After 60 minutes, glucose (4 g/kg) was orally administered at a dose of 5 ml/kg. The blood glucose was measured by using Accu-chek active strip (Roche diagnostic Co.). The time for the measurement was set at 60 minutes before the glucose administration (−60), 0 minute, 20 minutes, 40 minutes, 60 minutes, and 120 minutes after the glucose administration, and the blood glucose was measured through tail vein puncture. The results are shown in FIG. 6 and Table 12 below as a reduction (%) of blood glucose AUC.

TABLE 12

| Compound | Reduction (%) of blood glucose AUC |
| --- | --- |
| Metformin (50 mg/kg) | 21.7 |
| Example 9 (1 mg/kg) | 34.2 |
| Example 9 (3 mg/kg) | 40.9 |
| Example 9 (10 mg/kg) | 37.8 |
| Metformin (50 mg/kg) + Example 9 (1 mg/kg) | 43.0 |
| Metformin (50 mg/kg) + Example 9 (3 mg/kg) | 48.8 |
| Metformin (50 mg/kg) + Example 9 (10 mg/kg) | 48.3 |

Figure 6:
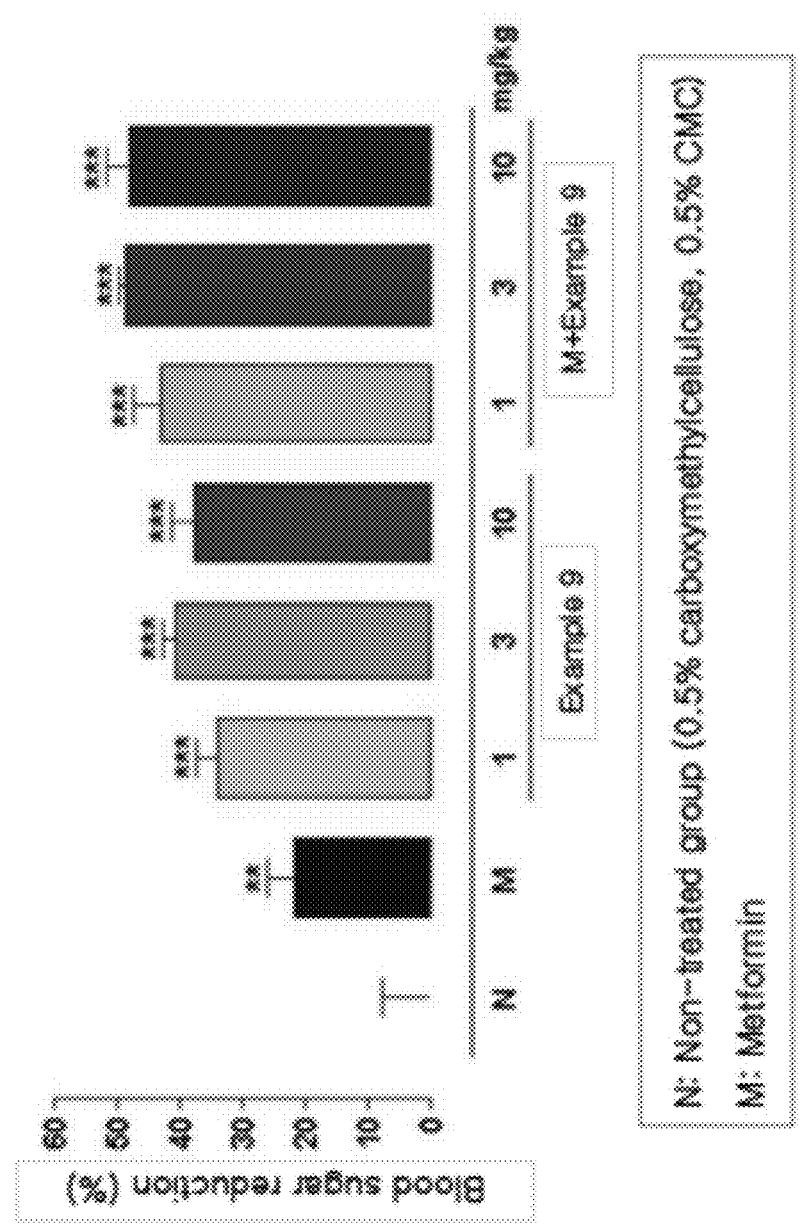
FIG. 6 is a graph illustrating the blood glucose reduction (%) shown when Zucker diabetic fatty (ZDF) rats were administered with the compound of Example 9 or metformin alone or co-administered with the compound of Example 9 and metformin.
Figure 7:
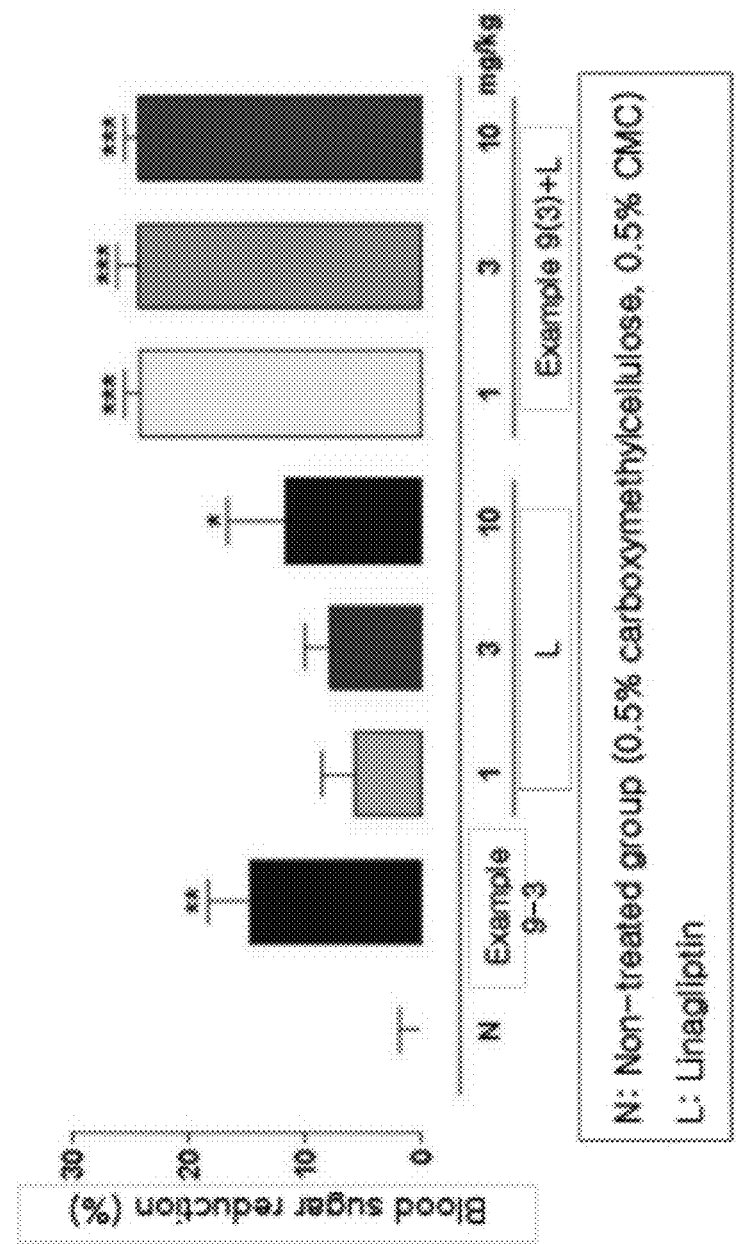
FIG. 7 is a graph illustrating the blood glucose reduction (%) shown when Sprague Dawley (SD) rats were administered with the compound of Example 9 or linagliptin alone or co-administered with the compound of Example 9 and linagliptin.

As shown in FIG. 6 and table 12 above, the blood glucose lowering effect was more excellent when metformin (50 mg/kg) and the compound (1 mg/kg, 3 mg/kg, or 10 mg/kg) prepared in Example 9 were co-administered rather than when metformin (50 mg/kg) was used alone.

11-2. SD Rat Model Experiment

Figure 8:
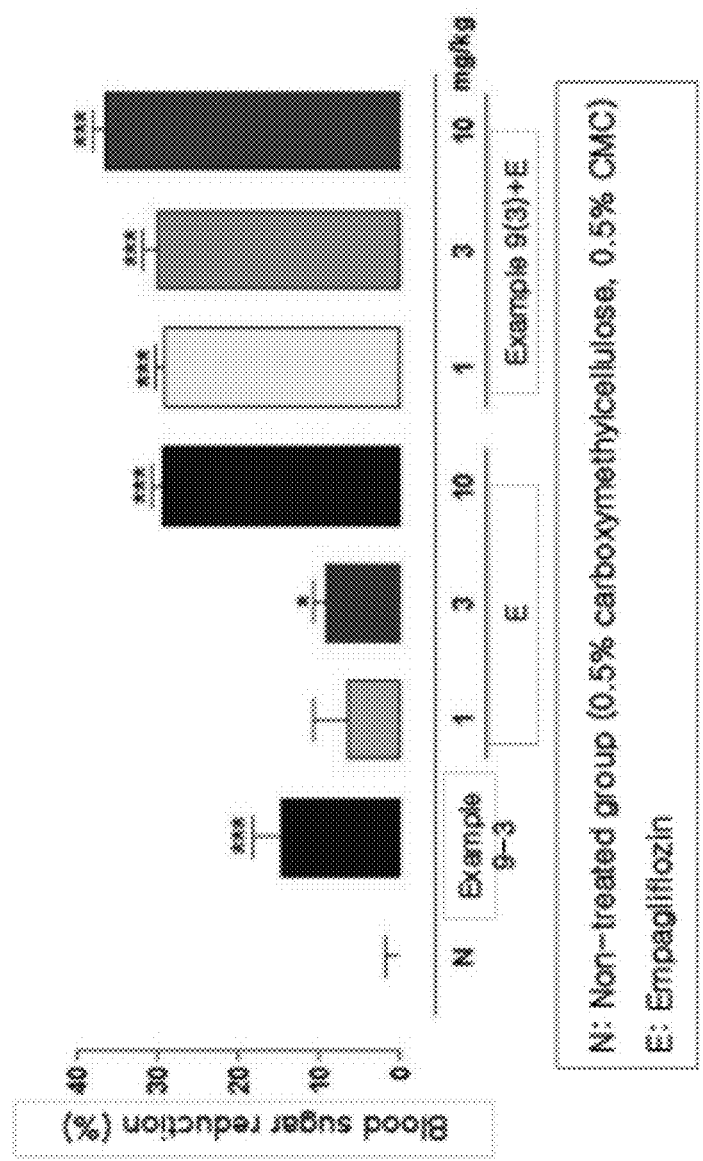
FIG. 8 is a graph illustrating the blood glucose reduction (%) shown when Sprague Dawley (SD) rats were administered with the compound of Example 9 or empagliflozin alone or co-administered with the compound of Example 9 and empagliflozin.

Male Sprague Dawley (SD) rats aged 8-10 weeks were acclimated for at least 7 days, and then only healthy animals were used for the OGTT experiment. After fasting for 16-18 hours, six rats per group were randomly grouped and administered with vehicle (0.5%, carboxymethyl cellulose (CMC)) or the compound of Example 9 (3 mg/kg) or metformin (10, 50, or 100 mg/kg), or co-administered with the compound of Example 9 (3 mg/kg) plus metformin (10, 50, or 100 mg/kg). Vehicle and the compound of Example 9 were orally administered at 10 ml/kg. After 30 minutes of administration of the vehicle or the compound of Example 9, glucose (4 g/kg) was orally administered at a dose of 5 ml/kg. The blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and the blood glucose was measured through tail vein puncture. The results are shown in FIG. 8 and Table 13 below as a reduction (%) of blood glucose AUC.

The experimental results were expressed as mean and standard error (Mean±SE), and the differences between the control and the experimental groups were tested by one-way ANOVA (a Dunnett method) of "GraphPad Prism 4" software (Graphpad co., La Jolla, Calif., USA). Here, p<0.05 was considered statistically significant.

In the co-administration of various doses of metformin and the compound of Example 9, the reduction (%) of AUC was observed to increase to values close to the threshold value that can be observed in the experimental environment, and each test group showed an area under curve (AUC) reduction effect of about 3.9-20.2% compared with the vehicle. These results indicate that the co-administration of the compound of Example 9 and a biguanide-based drug can maximize the efficacy of the biguanide-based drug while reducing the dose of the biguanide-based drug.

TABLE 13

| Compound | Reduction (%) of blood glucose AUC |
| --- | --- |
| Example 9 (3 mg/kg) | 14.5 |
| Metformin (10 mg/kg) | 3.9 |
| Metformin (50 mg/kg) | 7.3 |
| Metformin (100 mg/kg) | 10.0 |
| Example 9 (3 mg/kg) + Metformin (10 mg/kg) | 20.2 |
| Example 9 (3 mg/kg) + Metformin (50 mg/kg) | 16.5 |
| Example 9 (3 mg/kg) + Metformin (100 mg/kg) | 18.7 |

Therefore, the co-administration of a novel 3-(4-(benzyloxy)phenyl)hex-4-ynoic acid derivatives of the present invention and a biguanide-based drug shows an excellent blood glucose lowering effect compared with the administration of the drug alone, and thus, a pharmaceutical composition according to the present invention can be advantageously used in the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 12> Oral Glucose Tolerance Test (OGTT) by Co-Administration with Sodium/Glucose Cotransportor 2 (SGLT2) Inhibitor-Based Drug In order to evaluate the in vivo blood glucose lowering effect by co-administration of a novel 3-(4-(benzyloxy) phenyl)hex-4-ynoic acid derivative of the present invention and a sodium/glucose cotransportor 2 (SGLT2) inhibitor-based drug, the following experiment was carried out.

Figure 9:
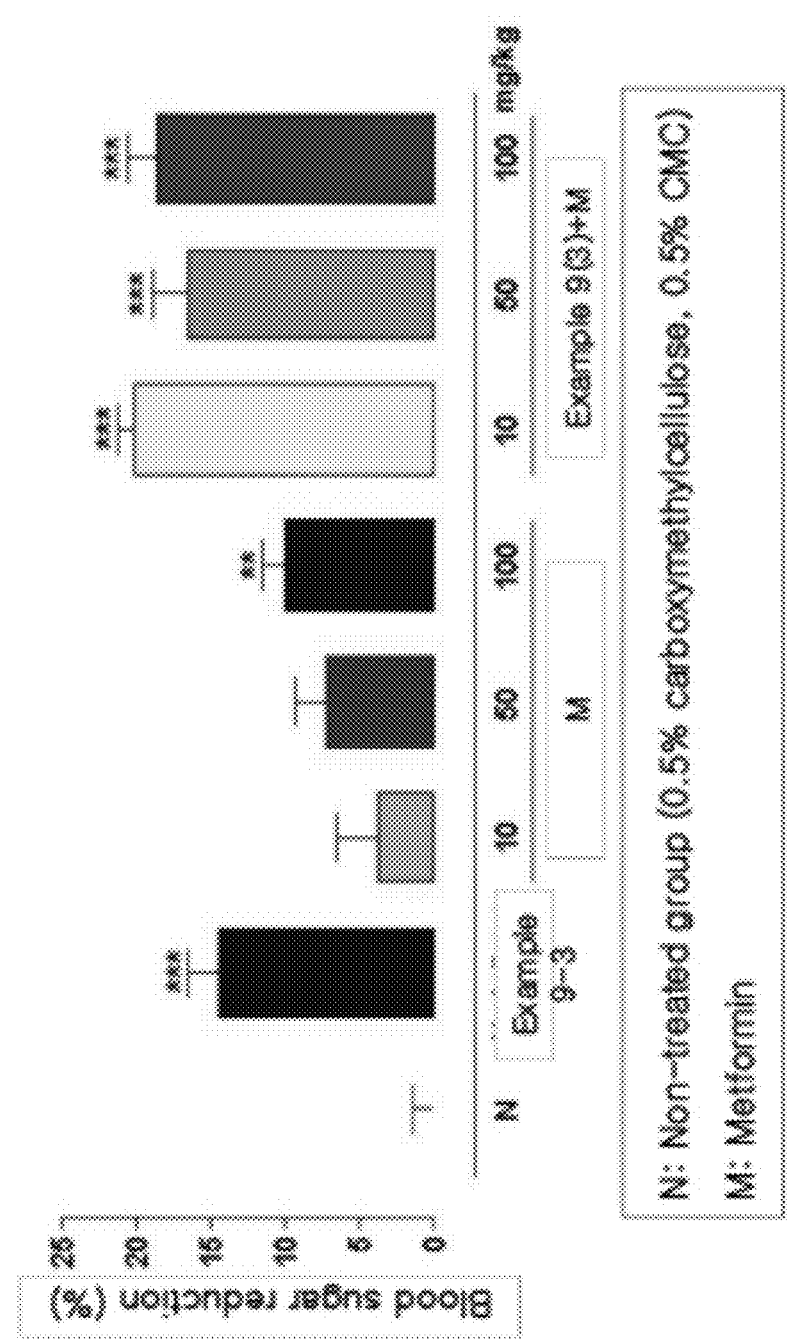
FIG. 9 is a graph illustrating the blood glucose reduction (%) shown when Sprague Dawley (SD) rats were administered with the compound of Example 9 or metformin alone or co-administered with the compound of Example 9 and metformin.
Figure 10:
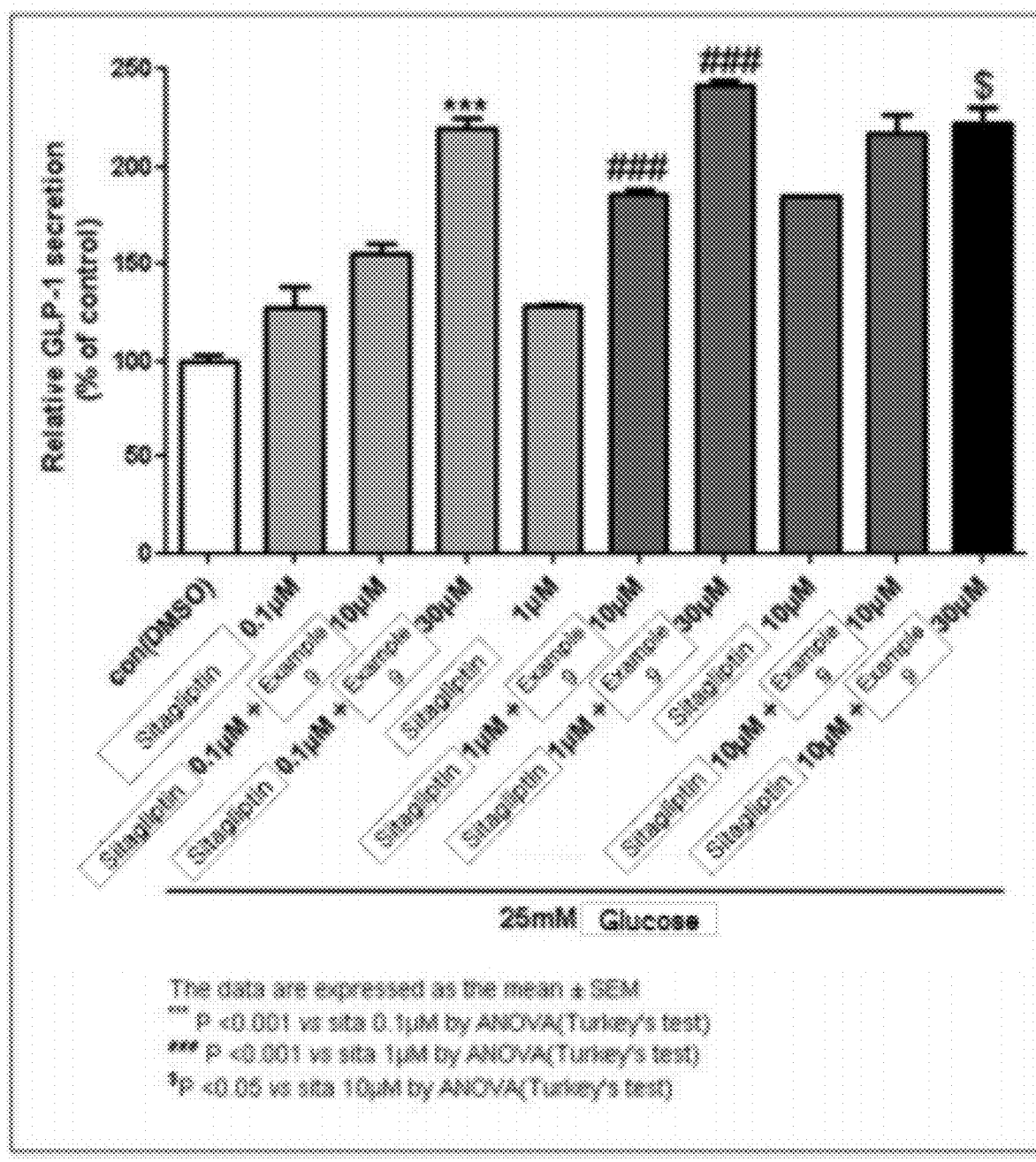
FIG. 10 illustrates the results of the in vitro GLP-1 secretion assay experiment using NCI-H716 cells.
Figure 11:
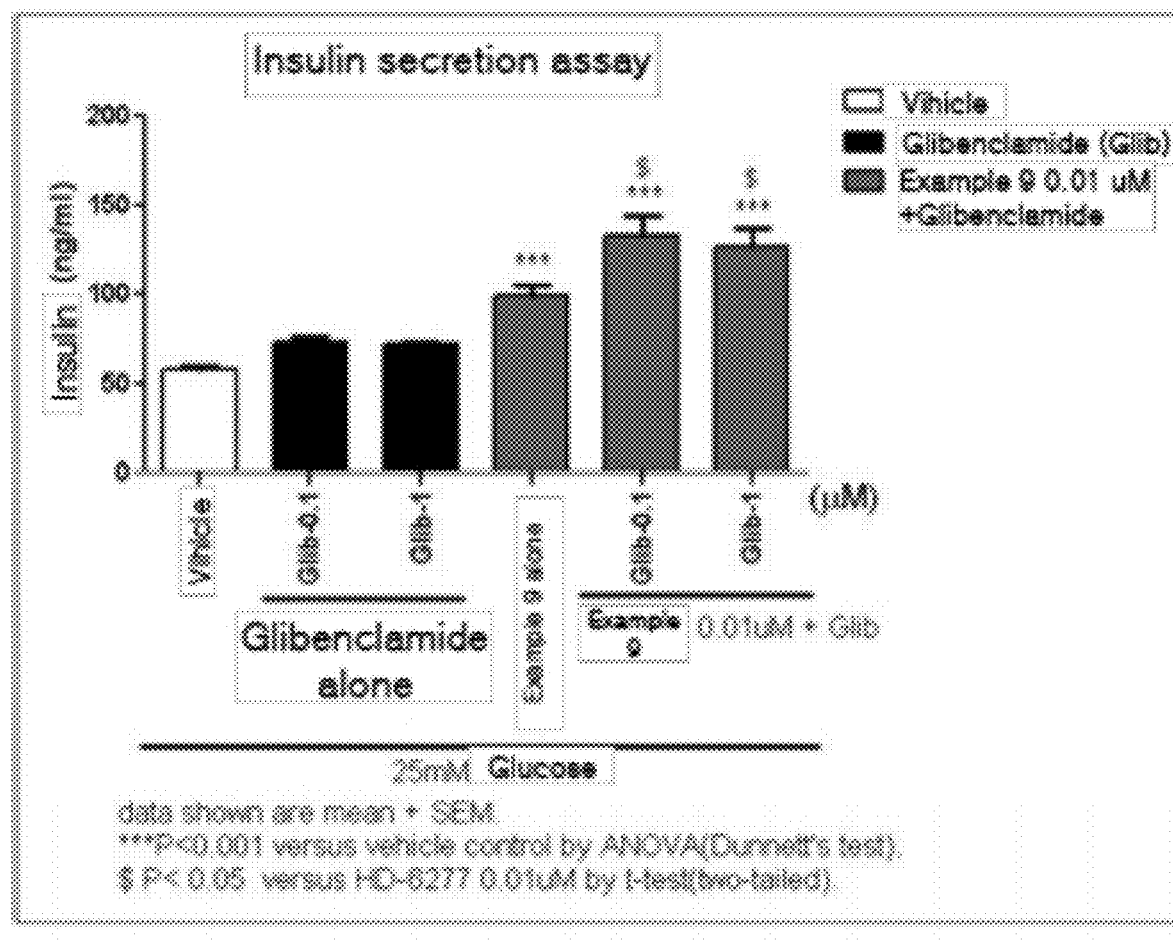
FIG. 11 illustrates the results of the in vitro insulin secretion experiment using INS-1 cells (rat insulinoma cell line).

Male Sprague Dawley (SD) rats aged 8-10 weeks were acclimated for at least 7 days, and then only healthy animals were used for the OGTT experiment. After fasting for 16-18 hours, six rats per group were randomly grouped and administered with vehicle (0.5%, carboxymethyl cellulose (CMC)) or the compound of Example 9 (3 mg/kg) or empagliflozin (1, 3, or 10 mg/kg), or co-administered with the compound of Example 9 (3 mg/kg) plus empagliflozin (1, 3, or 10 mg/kg). Vehicle and the compound of Example 9 were orally administered at 10 ml/kg. After 30 minutes of administration of the vehicle or the compound of Example 9, glucose (4 g/kg) was orally administered at a dose of 5 ml/kg. The blood glucose was measured by using Accu-chek active strip (Roche diagnostic Co.). The time for the measurement was set at 30 minutes before the glucose administration (−30), 0 minute, 20 minutes, 40 minutes, 60 minutes, and 120 minutes after the glucose administration, and the blood glucose was measured through tail vein puncture. The results are shown in FIG. 9 and Table 14 below as a reduction (%) of blood glucose AUC.

The experimental results were expressed as mean and standard error (Mean±SE), and the differences between the control and the experimental groups were tested by one-way ANOVA (a Dunnett method) of "GraphPad Prism 4" software (Graphpad co., La Jolla, Calif., USA). Here, $p<0.05$ was considered statistically significant.

In the co-administration of various doses of empagliflozin and the compound of Example 9, the reduction (%) of AUC was observed to increase to values close to the threshold value that can be observed in the experimental environment, and each test group showed an area under curve (AUC) reduction effect of about 6.5-36.6% compared with the vehicle. These results indicate that the co-administration of the compound of Example 9 and a SGLT2 inhibitor-based drug can maximize the efficacy of the SGLT2 inhibitor-based drug while reducing the dose of the SGLT2 inhibitor-based drug.

TABLE 14

| Compound | Reduction (%) of blood glucose AUC |
| --- | --- |
| Example 9 (3 mg/kg) | 14.8 |
| Empagliflozin (1 mg/kg) | 6.5 |
| Empagliflozin (3 mg/kg) | 9.2 |
| Empagliflozin (10 mg/kg) | 29.5 |
| Example 9 (3 mg/kg) + Empagliflozin (1 mg/kg) | 29.3 |
| Example 9 (3 mg/kg) + Empagliflozin (3 mg/kg) | 30.2 |
| Example 9 (3 mg/kg) + Empagliflozin (10 mg/kg) | 36.6 |

Therefore, the co-administration of a novel 3-(4-(benzyloxy)phenyl)hex-4-ynoic acid derivative of the present invention and a sodium/glucose cotransportor 2 (SGLT2) inhibitor-based drug shows an excellent blood glucose lowering effect compared with the administration of the drug alone, and thus, a pharmaceutical composition of the present invention can be advantageously used in the prevention or treatment of metabolic diseases, such as obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

<Experimental Example 13> GLP-1 Secretion Assay Experiment

NCI-H716 cells were seeded in a 12-well plate coated with Matrigel (BD) at 1×106 cells/well, and cultured in an incubator (37° C.) for 48 hours. After removing the supernatant, the cells were washed with DMEM low glucose (5.5 mM; containing 2% FBS, 2 mM L-glutamine, 100 IU/ml penicillin, and 100 ug/ml streptomycin) medium, and subjected to starvation in the same medium for 4 hours. After removing the supernatant, the medium was replaced with DMEM high glucose (25 mM) containing diluted sitagliptin (0.1, 1, or 10 μM), and then pre-treated for 30 minutes. After 30 minutes, the medium was treated with the compound of Example 9 at each dose (1, 10, or 30 μM), and then the cells were cultured at 37° C. for 2 hours. As a control group, 0.1% DMSO was used. The amount of GLP-1 secreted from NCI-H716 cells was measured through a glucagon-like peptide-1 (GLP-1) kit (Millipore) by using the supernatant of the cells after the experiment was ended (see Table 15 and FIG. 10).

TABLE 15

| Compound | Relative proportion (%) of GLP-1 secretion in each experimental group compared with control |
| --- | --- |
| Control | 100.0 ± 2.3 |
| Sitagliptin (0.1 μM) | 127.5 ± 7.3 |
| Sitagliptin (0.1 μM) + Example 9 (10 μM) | 155.7 ± 3.4 |
| Sitagliptin (0.1 μM) + Example 9 (30 μM) | 219.6 ± 3.7*** |
| Sitagliptin (1 μM) | 128.1 ± 0.6 |
| Sitagliptin (1 μM) + Example 9 (10 μM) | 185.7 ± 2.0### |
| Sitagliptin (1 μM) + Example 9 (30 μM) | 241.4 ± 2.0### |
| Sitagliptin (10 μM) | 184.9 ± 0.2 |
| Sitagliptin (10 μM) + Example 9 (10 μM) | 216.9 ± 6.7 |
| Sitagliptin (10 μM) + Example 9 (30 μM) | 221.9 ± 6.0$ |

As a result, it was observed that the GLP-1 secretion was significantly increased in the co-treatment groups with sitagliptin and the compound of Example 9, compared with the treatment groups with sitagliptin alone.

<Experimental Example 14> Insulin secretion experiment

INS-1 cells (rat insulinoma cell line) were seeded in a 24-well plate at $5 \times 10^5$ cells/well, and cultured for 48 hours. After the cells were washed with 3 mM glucose-KRB buffer (118 mM NaCl, 4.7 mM KCl, 1.2 mM $KH_2PO_4$, 1.16 mM $MgCl_2$, 10 mM HEPES, 2.5 mM $CaCl_2$, 25.5 mM $NaHCO_3$, 0.2% BSA, pH 7.4), and cultured in the same buffer for 2 hours, so that the intracellular glucose concentration could be in a low concentration state. The test compound (see Table 16) was diluted to a final concentration of 0.1-10 M in 25 mM glucose-KRB buffer, and then used to treat the cells upon completion of the culture in 3 mM glucose conditions for 1 hour, thereby inducing the insulin secretion. The amount of insulin secreted in the insulin ELISA kit (Morinaga) was measured using the supernatant of the cells after the experiment was ended (see Table 16 and FIG. 11).

TABLE 16

| Compound | Insulin (ng/ml) | SEM |
| --- | --- | --- |
| Vehicle | 58 | 2.29 |
| Glibenclamide (0.1 μM) | 73 | 2.48 |
| Glibenclamide (1 μM) | 72 | 1.51 |
| Example 9 (0.01 μM) | 99 | 6.41 |
| Example 9 (0.01 μM) + Glibenclamide (0.1 μM) | 133 | 10.98 |
| Example 9 (0.01 μM) + Glibenclamide (1 μM) | 128 | 9.14 |

As a result, it was verified that the insulin secretion was more increased in the co-administration groups with glibenclamide and the compound of Example 9, compared with the administration groups with the compound of Example 9 alone.

<Preparation Example 1> Preparation of Pharmaceutical Preparation

| 1-1. Preparation of powders | |
|---|---|
| Compound of formula 1 | 500 mg |
| Lactose | 100 mg |
| Talc | 10 mg |

Powders were prepared by mixing all the above ingredients and then packaging the mixture in an airtight bag.

| 1-2. Preparation of tablets | |
|---|---|
| Compound of formula 1 | 500 mg |
| Corn starch | 100 mg |
| Lactose | 100 mg |
| Magnesium stearate | 2 mg |

Tablets were prepared by mixing the above ingredients and then tableting the mixture according to an ordinary method for preparing a tablet preparation.

| 1-3. Preparation of capsules | |
|---|---|
| Compound of formula 1 | 500 mg |
| Corn starch | 100 mg |
| Lactose | 100 mg |
| Magnesium stearate | 2 mg |

Capsules were prepared by mixing the above ingredients and then filling the mixture in a gelatin capsule according to an ordinary method for preparing a capsule preparation.

| 1-4. Preparation of injections | |
|---|---|
| Compound of formula 1 | 500 mg |
| Sterile distilled water for injection | Suitable amount |
| pH adjuster | Suitable amount |

Injections were prepared by containing the above ingredients per ampoule (2 mL) according to an ordinary method for preparing an injection.

| 1-5. Preparation of liquid formulations | |
|---|---|
| Compound of formula 1 | 100 mg |
| Isomerized sugar | 10 g |
| Mannitol | 5 g |
| Purified water | Suitable amount |

According to an ordinary method for preparing a liquid formulation, each ingredient was dissolved in purified water, to which a lemon flavor was added, and then the above ingredients were mixed, to which purified water was added to make the total volume to 100 mL. The mixture was filled in a brown bottle and sterilized to prepare liquid formulations.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A composition comprising:
   (a) a compound of Formula (1), an optical isomer, hydrate, or solvate thereof, or a pharmaceutically acceptable salt thereof; and
   (b) at least one compound selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLT2) inhibitor-based compounds:

Formula (1)

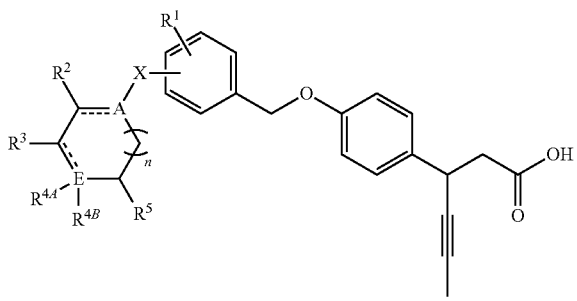

wherein is a single bond or double bond;
A and E are each independently C or N;
n is 1;
X is a single bond, or $C_{1-3}$ straight or branched alkylene;
$R^1$ is —H or

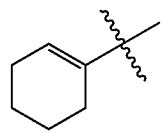 [SMILES: *C1=CCCCC1]

$R^2$ is —H, or $R^2$ and $R^3$, together with the atoms to which they are attached, form phenyl;
$R^3$ is —H, or $R^3$ and $R^2$ together with the atoms to which they are attached, form phenyl, or $R^3$ and $R^{4A}$ together with the atoms to which they are attached, form phenyl and the phenyl may be substituted with a methoxy group;
$R^{4A}$ is —H, —OH, =O,

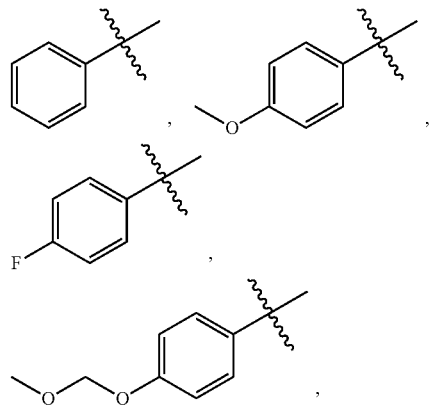

-continued

[chemical structures]

or R³ and R⁴ᴬ, together with the atoms to which they are attached, form phenyl, and the phenyl may be substituted with a methoxy group, or R⁴ᴬ and R⁴ᴮ, together with the atoms to which they are attached, form

[chemical structure]

R⁴ᴮ is absent, —H, or R⁴ᴮ, together with the atoms to which R⁴ᴮ is attached and R⁴ᴬ, form

[chemical structure]

and
R⁵ is —H.

2. The composition of claim 1, wherein the dipeptidyl peptidase IV inhibitor-based compound is selected from the group consisting of sitagliptin, vildagliptin, saxagliptin, linagliptin, teneligliptin, alogliptin, gemigliptin, dutogliptin, berberine, lupeol, red alder, and dandelion coffee.

3. The composition of claim 1, wherein the sulfonyl urea-based compound is selected from the group consisting of carbutamide, acetohexamide, chlorpropamide, tolbutamide, glipizide, gliclazide, glibenclamide, glibornuride, gliquidone, glisoxepide, glyclopyramide, and glimepiride.

4. The composition of claim 1, wherein the thiazolidinedione-based compound is selected from the group consisting of rosiglitazone, pioglitazone, troglitazone, netoglitazone, rivoglitazone, ciglitazone, and rhodanine.

5. The composition of claim 1, wherein the biguanide-based compound is selected from the group consisting of metformin, phenformin, buformin, proguanil, chlorproguanil, chlorhexidine, polyaminopropyl biguanide (PAPB), polihexanide, and alexidine.

6. The composition of claim 1, wherein the SGLT2 inhibitor-based compound is selected from the group consisting of empagliflozin, canagliflozin, and dapagliflozin.

7. The composition of claim 1, wherein the weight ratio of (a) the compound of Formula (1) and (b) the at least one compound is 0.03:1 to 100:1.

8. The composition of claim 1, wherein the composition is capable of activating G-protein receptor 40 (GPR40) enzyme.

9. A composition comprising (a) a compound, an optical isomer, hydrate, or solvate thereof, or a pharmaceutically acceptable salt thereof; and (b) at least one compound selected from the group consisting of dipeptidyl peptidase IV (DPPIV) inhibitor-based, sulfonylurea-based, thiazolidinedione (TZD)-based, biguanide-based, and sodium/glucose cotransporter 2 (SGLTT2) inhibitor-based compounds, wherein (a) the compound is selected from the group consisting of:
  3-(4-(3-(1,4-dioxaspiro[4.5]dec-7-en-8-yl)benzyloxy)phenyl)hex-4-ynoic acid;
  L-lysine 3-(4-(3-(1,4-dioxaspiro[4.5]dec-7-en-8-yl)benzyloxy)phenyl)hex-4-ynoate;
  4-(4-(3-(1,4-dioxaspiro[4.5]dec-7-en-8-yl)benzyloxy)phenyl)hex-4-ynoic acid;
  3-(4-(3-(4-oxocyclohex-1-enyl)benzyloxy)phenyl)hex-4-ynoic acid;
  3-(4-(3-(4-hydroxycyclohex-1-enyl)benzyloxy)phenyl)hex-4-ynoic acid;
  L-lysine 3-(4-(3-(4-hydroxycyclohex-1-enyl)benzyloxy)phenyl)hex-4-ynoate;
  (3S)-3-(4-(3-(1,4-dioxaspiro[4.5]dec-7-en-8-yl)benzyloxy)phenyl)hex-4-ynoic acid;
  (3R)-3-(4-(3-(1,4-dioxaspiro[4.5]dec-7-en-8-yl)benzyloxy)phenyl)hex-4-ynoic acid;
  L-lysine (3S)-3-(4-(3-(1,4-dioxaspiro[4.5]dec-7-en-8-yl)benzyloxy)phenyl)hex-4-ynoate;
  L-lysine (3R)-3-(4-(3-(1,4-dioxaspiro[4.5]dec-7-en-8-yl)benzyloxy)phenyl)hex-4-ynoate;
  sodium (3S)-3-(4-(3-(1,4-dioxaspiro[4.5]dec-7-en-8-yl)benzyloxy)phenyl)hex-4-ynoate;
  3-(4-(4-((3,4-dihydroisoquinolin-2(1H)-yl)methyl)benzyloxy)phenyl)hex-4-ynoic acid;
  3-(4-(3-cyclohexenyl-4-((3,4-dihydroisoquinolin-2(1H)-yl)methyl)benzyloxy)phenyl)hex-4-ynoic acid;
  3-(4-(4-((4-phenyl-5,6-dihydropyridin-1(2H)-yl)methyl)benzyloxy)phenyl)hex-4-ynoic acid;
  3-(4-(4-((4-phenylpiperazin-1-yl)methyl)benzyloxy)phenyl)hex-4-ynoic acid;
  3-(4-(4-((6-methoxy-3,4-dihydroisoquinolin-2(1H)-yl)methyl)benzyloxy)phenyl)hex-4-ynoic acid;
  3-(4-(4-((4-phenylpiperidin-1-yl)methyl)benzyloxy)phenyl)hex-4-ynoic acid;
  3-(4-(4-((4-(4-fluorophenyl)piperazin-1-yl)methyl)benzyloxy)phenyl)hex-4-ynoic acid;

3-(4-(4-((4-(4-(trifluoromethyl)phenyl)piperazin-1-yl)
methyl)benzyloxy)phenyl)hex-4-ynoic acid;

3-(4-(4-((4-(4-(3-(methylsulfonyl)propoxy)phenyl)piperazin-1-yl)methyl)benzyloxy)phenyl)hex-4-ynoic acid;

(S)-3-(4-(4-((3,4-dihydroisoquinolin-2(1H)-yl)methyl)benzyloxy)phenyl)hex-4-ynoic acid;

(S)-3-(4-(4-((4-(4-(trifluoromethyl)phenyl)piperazin-1-yl)methyl)benzyloxy)phenyl)hex-4-ynoic acid;

(S)-3-(4-(4-((4-(4-fluorophenyl)piperazin-1-yl)methyl)benzyloxy)phenyl)hex-4-ynoic acid;

potassium (S)-3-(4-(4-((4-(4-(trifluoromethyl)phenyl)piperazin-1-yl)methyl)benzyloxy)phenyl)hex-4-ynoate;

(S)-3-(4-(4-((6-methoxy-3,4-dihydroisoquinolin-2(1H)-yl)methyl)benzyloxy)phenyl)hex-4-ynoic acid;

(S)-3-(4-(4-((4-phenylpiperidin-1-yl)methyl)benzyloxy)phenyl)hex-4-ynoic acid;

(S)-3-(4-(4-(isoindolin-2-ylmethyl)benzyloxy)phenyl)hex-4-ynoic acid;

(S)-3-(4-(4-((4-phenyl-5,6-dihydropyridin-1(2H)-yl)methyl)benzyloxy)phenyl)hex-4-ynoic acid;

(S)-3-(4-(4-((4-(4-(methoxymethoxy)phenyl)piperazin-1-yl)methyl)benzyloxy)phenyl)hex-4-ynoic acid;

(S)-3-(4-(4-((4-(5-isopropyl-1,2,4-oxadiazol-3-yl)piperidin-1-yl)methyl)benzyloxy)phenyl)hex-4-ynoic acid;

(S)-3-(4-(4-((4-(5-isopropyl-1,2,4-oxadiazol-3-yl)piperazin-1-yl)methyl)benzyloxy)phenyl)hex-4-ynoic acid;

(S)-3-(4-(4-((4-(4-(methylsulfonyl)phenyl)-5,6-dihydropyridin-1(2H)-yl)methyl)benzyloxy)phenyl)hex-4-ynoic acid;

(S)-3-(4-(4-((4-(4-(3-(methylsulfonyl)propoxy)phenyl)-5,6-dihydropyridin-1(2H)-yl)methyl)benzyloxy)phenyl)hex-4-ynoic acid;

(3S)-3-(4-(4-(1-(3,4-dihydroisoquinolin-2(1H)-yl)ethyl)benzyloxy)phenyl)hex-4-ynoic acid;

(S)-3-(4-(4-((4-(4-hydroxyphenyl)piperazin-1-yl)methyl)benzyloxy)phenyl)hex-4-ynoic acid;

(S)-3-(4-(4-((4-(4-(3-(methylsulfonyl)propoxy)phenyl)piperazin-1-yl)methyl)benzyloxy)phenyl)hex-4-ynoic acid;

sodium (S)-3-(4-(4-(isoindolin-2-ylmethyl)benzyloxy)phenyl)hex-4-ynoate;

L-lysine (S)-3-(4-(4-(isoindolin-2-ylmethyl)benzyloxy)phenyl)hex-4-ynoate;

(S)-3-(4-(4-((4-(4-fluorophenyl)-5,6-dihydropyridin-1(2H)-yl)methyl)benzyloxy)phenyl)hex-4-ynoic acid;

(S)-3-(4-(4-((4-(4-methoxyphenyl)piperazin-1-yl)methyl)benzyloxy)phenyl)hex-4-ynoic acid;

sodium (S)-3-(4-(4-((3,4-dihydroquinolin-1(2H)-yl)methyl)benzyloxy)phenyl)hex-4-ynoate;

potassium (S)-3-(4-(4-((3,4-dihydroquinolin-1(2H)-yl)methyl)benzyloxy)phenyl)hex-4-ynoate;

(S)-3-(4-(4-((4-(benzo[d]thiazol-2-yl)piperazin-1-yl)methyl)benzyloxy)phenyl)hex-4-ynoic acid;

(S)-3-(4-(4-((4-(5-propylpyrimidin-2-yl)piperazin-1-yl)methyl)benzyloxy)phenyl)hex-4-ynoic acid;

(S)-3-(4-(4-((4-(5-cyanopyridin-2-yl)piperazin-1-yl)methyl)benzyloxy)phenyl)hex-4-ynoic acid;

(3S)-3-(4-(4-((3-phenylpyrrolidin-1-yl)methyl)benzyloxy)phenyl)hex-4-ynoic acid;

sodium (S)-3-(4-(3-(4-(4-methoxyphenyl)piperazin-1-yl)benzyloxy)phenyl)hex-4-ynoate;

(S)-3-(4-(4-(2-(6-methoxy-3,4-dihydroisoquinolin-2(1H)-yl)ethyl)benzyloxy)phenyl)hex-4-ynoic acid;

(S)-3-(4-(4-(2-(isoindolin-2-yl)ethyl)benzyloxy)phenyl)hex-4-ynoic acid;

(S)-3-(4-(4-(2-(3,4-dihydroisoquinolin-2(1H)-yl)ethyl)benzyloxy)phenyl)hex-4-ynoic acid; and sodium (S)-3-(4-(4-((6-methoxy-3,4-dihydroisoquinolin-2(1H)-yl)methyl)benzyloxy)phenyl)hex-4-ynoate.

10. The composition of claim 9, wherein the dipeptidyl peptidase IV inhibitor-based compound is selected from the group consisting of sitagliptin, vildagliptin, saxagliptin, linagliptin, teneligliptin, alogliptin, gemigliptin, dutogliptin, berberine, lupeol, red alder, and dandelion coffee.

11. The composition of claim 9, wherein the sulfonyl urea-based compound is selected from the group consisting of carbutamide, acetohexamide, chlorpropamide, tolbutamide, glipizide, gliclazide, glibenclamide, glibornuride, gliquidone, glisoxepide, glyclopyramide, and glimepiride.

12. The composition of claim 9, wherein the thiazolidinedione-based compound is selected from the group consisting of rosiglitazone, pioglitazone, troglitazone, netoglitazone, rivoglitazone, ciglitazone, and rhodanine.

13. The composition of claim 9, wherein the biguanide-based compound is selected from the group consisting of metformin, phenformin, buformin, proguanil, chlorproguanil, chlorhexidine, polyaminopropyl biguanide (PAPB), polihexanide, and alexidine.

14. The composition of claim 9, wherein the SGLT2 inhibitor-based compound is selected from the group consisting of empagliflozin, canagliflozin, and dapagliflozin.

15. The composition of claim 9, wherein the weight ratio of (a) the compound and (b) the at least one compound is 0.03:1 to 100:1.

16. The composition of claim 9, wherein the composition is capable of activating G-protein receptor 40 (GPR40) enzyme.

17. A method for preventing or treating a metabolic disease, the method comprising:
administering to a subject a pharmaceutically effective amount of a composition comprising:
(a) a compound of Formula (1) of claim 1, an optical isomer, hydrate, or solvate thereof, or a pharmaceutically acceptable salt thereof; and
(b) at least one compound selected from the group consisting of dipeptidyl peptidase-IV (DPP-IV) inhibitor-based, sulfonylurea-based, thiazolidinedione (TZD)-based, biguanide-based, and sodium/glucose cotransporter 2 (SGLT2) inhibitor-based compounds.

18. The method of claim 17, wherein the mixing weight ratio of (a) the compound of Formula (1) and (b) the at least one compound is 0.03:1 to 100:1.

19. The method of claim 17, wherein the metabolic disease is selected from the group consisting of obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

20. A method for preventing or treating a metabolic disease, the method comprising:
administering to a subject a pharmaceutically effective amount of a composition comprising:
(a) a compound, an optical isomer, hydrate, or solvate thereof, or a pharmaceutically acceptable salt thereof; and
(b) at least one compound selected from the group consisting of dipeptidyl peptidase-IV (DPP-IV) inhibitor-based, sulfonylurea-based, thiazolidinedione (TZD)-based, biguanide-based, and sodium/glucose cotransporter 2 (SGLT2) inhibitor-based compounds, wherein (a) the compound is selected from the group consisting of:

3-(4-(3-(1,4-dioxaspiro[4.5]dec-7-en-8-yl)benzyloxy)
phenyl)hex-4-ynoic acid;
L-lysine 3-(4-(3-(1,4-dioxaspiro[4.5]dec-7-en-8-yl)benzyloxy)phenyl)hex-4-ynoate;
4-(4-(3-(1,4-dioxaspiro[4.5]dec-7-en-8-yl)benzyloxy)
phenyl)hex-4-ynoic acid;
3-(4-(3-(4-oxocyclohex-1-enyl)benzyloxy)phenyl)hex-4-ynoic acid;
3-(4-(3-(4-hydroxycyclohex-1-enyl)benzyloxy)phenyl)
hex-4-ynoic acid;
L-lysine 3-(4-(3-(4-hydroxycyclohex-1-enyl)benzyloxy)
phenyl)hex-4-ynoate;
(3S)-3-(4-(3-(1,4-dioxaspiro[4.5]dec-7-en-8-yl)benzyloxy)phenyl)hex-4-ynoic acid;
(3R)-3-(4-(3-(1,4-dioxaspiro[4.5]dec-7-en-8-yl)benzyloxy)phenyl)hex-4-ynoic acid;
L-lysine (3S)-3-(4-(3-(1,4-dioxaspiro[4.5]dec-7-en-8-yl)
benzyloxy)phenyl)hex-4-ynoate;
L-lysine (3R)-3-(4-(3-(1,4-dioxaspiro[4.5]dec-7-en-8-yl)
benzyloxy)phenyl)hex-4-ynoate;
sodium (3S)-3-(4-(3-(1,4-dioxaspiro[4.5]dec-7-en-8-yl)
benzyloxy)phenyl)hex-4-ynoate;
3-(4-(4-((3,4-dihydroisoquinolin-2(1H)-yl)methyl)benzyloxy)phenyl)hex-4-ynoic acid;
3-(4-(3-cyclohexenyl-4-((3,4-dihydroisoquinolin-2(1H)-yl)methyl)benzyloxy)phenyl)hex-4-ynoic acid;
3-(4-(4-((4-phenyl-5,6-dihydropyridin-1(2H)-yl)methyl)
benzyloxy)phenyl)hex-4-ynoic acid;
3-(4-(4-((4-phenylpiperazin-1-yl)methyl)benzyloxy)phenyl)hex-4-ynoic acid;
3-(4-(4-((6-methoxy-3,4-dihydroisoquinolin-2(1H)-yl)
methyl)benzyloxy)phenyl)hex-4-ynoic acid;
3-(4-(4-((4-phenylpiperidin-1-yl)methyl)benzyloxy)phenyl)hex-4-ynoic acid;
3-(4-(4-((4-(4-fluorophenyl)piperazin-1-yl)methyl)benzyloxy)phenyl)hex-4-ynoic acid;
3-(4-(4-((4-(4-(trifluoromethyl)phenyl)piperazin-1-yl)
methyl)benzyloxy)phenyl)hex-4-ynoic acid;
3-(4-(4-((4-(4-(3-(methylsulfonyl)propoxy)phenyl)piperazin-1-yl)methyl)benzyloxy)phenyl)hex-4-ynoic acid;
(S)-3-(4-(4-((3,4-dihydroisoquinolin-2(1H)-yl)methyl)
benzyloxy)phenyl)hex-4-ynoic acid;
(S)-3-(4-(4-((4-(4-(trifluoromethyl)phenyl)piperazin-1-yl)methyl)benzyloxy)phenyl)hex-4-ynoic acid;
(S)-3-(4-(4-((4-(4-fluorophenyl)piperazin-1-yl)methyl)
benzyloxy)phenyl)hex-4-ynoic acid;
potassium (S)-3-(4-(4-((4-(4-(trifluoromethyl)phenyl)
piperazin-1-yl)methyl)benzyloxy)phenyl)hex-4-ynoate;
(S)-3-(4-(4-((6-methoxy-3,4-dihydroisoquinolin-2(1H)-yl)methyl)benzyloxy)phenyl)hex-4-ynoic acid;
(S)-3-(4-(4-((4-phenylpiperidin-1-yl)methyl)benzyloxy)
phenyl)hex-4-ynoic acid;
(S)-3-(4-(4-(isoindolin-2-ylmethyl)benzyloxy)phenyl)
hex-4-ynoic acid;
(S)-3-(4-(4-((4-phenyl-5,6-dihydropyridin-1(2H)-yl)
methyl)benzyloxy)phenyl)hex-4-ynoic acid;
(S)-3-(4-(4-((4-(4-(methoxymethoxy)phenyl)piperazin-1-yl)methyl)benzyloxy)phenyl)hex-4-ynoic acid;
(S)-3-(4-(4-((4-(5-isopropyl-1,2,4-oxadiazol-3-yl)piperidin-1-yl)methyl)benzyloxy)phenyl)hex-4-ynoic acid;
(S)-3-(4-(4-((4-(5-isopropyl-1,2,4-oxadiazol-3-yl)piperazin-1-yl)methyl)benzyloxy)phenyl)hex-4-ynoic acid;
(S)-3-(4-(4-((4-(4-(methylsulfonyl)phenyl)-5,6-dihydropyridin-1(2H)-yl)methyl)benzyloxy)phenyl)hex-4-ynoic acid;
(S)-3-(4-(4-((4-(4-(3-(methylsulfonyl)propoxy)phenyl)-5,6-dihydropyridin-1(2H)-yl)methyl)benzyloxy)phenyl)hex-4-ynoic acid;
(3S)-3-(4-(4-(1-(3,4-dihydroisoquinolin-2(1H)-yl)ethyl)
benzyloxy)phenyl)hex-4-ynoic acid;
(S)-3-(4-(4-((4-(4-hydroxyphenyl)piperazin-1-yl)methyl)
benzyloxy)phenyl)hex-4-ynoic acid;
(S)-3-(4-(4-((4-(4-(3-(methylsulfonyl)propoxy)phenyl)
piperazin-1-yl)methyl)benzyloxy)phenyl)hex-4-ynoic acid;
sodium (S)-3-(4-(4-(isoindolin-2-ylmethyl)benzyloxy)
phenyl)hex-4-ynoate;
L-lysine (S)-3-(4-(4-(isoindolin-2-ylmethyl)benzyloxy)
phenyl)hex-4-ynoate;
(S)-3-(4-(4-((4-(4-fluorophenyl)-5,6-dihydropyridin-1
(2H)-yl)methyl)benzyloxy)phenyl)hex-4-ynoic acid;
(S)-3-(4-(4-((4-(4-methoxyphenyl)piperazin-1-yl)
methyl)benzyloxy)phenyl)hex-4-ynoic acid;
sodium (S)-3-(4-(4-((3,4-dihydroquinolin-1(2H)-yl)
methyl)benzyloxy)phenyl)hex-4-ynoate;
potassium (S)-3-(4-(4-((3,4-dihydroquinolin-1(2H)-yl)
methyl)benzyloxy)phenyl)hex-4-ynoate;
(S)-3-(4-(4-((4-(benzo[d]thiazol-2-yl)piperazin-1-yl)
methyl)benzyloxy)phenyl)hex-4-ynoic acid;
(S)-3-(4-(4-((4-(5-propylpyrimidin-2-yl)piperazin-1-yl)
methyl)benzyloxy)phenyl)hex-4-ynoic acid;
(S)-3-(4-(4-((4-(5-cyanopyridin-2-yl)piperazin-1-yl)
methyl)benzyloxy)phenyl)hex-4-ynoic acid;
(3S)-3-(4-(4-((3-phenylpyrrolidin-1-yl)methyl)benzyloxy)phenyl)hex-4-ynoic acid;
(S)-3-(4-(4-(2-(6-methoxy-3,4-dihydroisoquinolin-2
(1H)-yl)ethyl)benzyloxy)phenyl)hex-4-ynoic acid;
(S)-3-(4-(4-(2-(isoindolin-2-yl)ethyl)benzyloxy)phenyl)
hex-4-ynoic acid;
(S)-3-(4-(4-(2-(3,4-dihydroisoquinolin-2(1H)-yl)ethyl)
benzyloxy)phenyl)hex-4-ynoic acid; and
sodium (S)-3-(4-(4-((6-methoxy-3,4-dihydroisoquinolin-2(1H)-yl)methyl)benzyloxy)phenyl)hex-4-ynoate.

21. The method of claim 20, wherein the mixing weight ratio of (a) the compound and (b) the at least one compound is 0.03:1 to 100:1.

22. The method of claim 20, wherein the metabolic disease is selected from the group consisting of obesity, type I diabetes, type II diabetes, impaired glucose tolerance, insulin resistance syndrome, hyperglycemia, hyperlipidemia, hypertriglyceridemia, hypercholesterolemia, dyslipidemia, and syndrome X.

* * * * *